United States Patent [19]
Douglas et al.

[11] Patent Number: 6,039,688
[45] Date of Patent: Mar. 21, 2000

[54] THERAPEUTIC BEHAVIOR MODIFICATION PROGRAM, COMPLIANCE MONITORING AND FEEDBACK SYSTEM

[75] Inventors: Peter Douglas, Montecito, Calif.; Evan Dudik, Vancouver, Wash.; John Evans, Pittstown, N.J.; Alan Kritzer, Van Nuys, Calif.

[73] Assignee: Salus Media Inc., Sherman Oaks, Calif.

[21] Appl. No.: 08/962,238

[22] Filed: Oct. 31, 1997

Related U.S. Application Data

[60] Provisional application No. 60/029,862, Nov. 1, 1996, and provisional application No. 60/052,222, Jul. 11, 1997.

[51] Int. Cl.$^7$ ............................... A61B 3/00; G06F 15/00
[52] U.S. Cl. ............................... 600/300; 128/921
[58] Field of Search .................... 600/300, 301; 128/920, 921, 923, 897, 898

[56] References Cited

U.S. PATENT DOCUMENTS

| | | | |
|---|---|---|---|
| 4,712,562 | 12/1987 | Ohayon et al. | 128/672 |
| 4,731,726 | 3/1988 | Allen, III | 364/416 |
| 4,779,199 | 10/1988 | Yoneda et al. | 364/413.03 |
| 4,803,625 | 2/1989 | Fu et al. | 364/413.03 |
| 4,803,997 | 2/1989 | Bowman | 128/723 |
| 4,838,275 | 6/1989 | Lee | 128/670 |
| 4,933,873 | 6/1990 | Kaufman et al. | 364/513.5 |
| 4,951,197 | 8/1990 | Mellinger | 364/413.2 |
| 4,975,842 | 12/1990 | Darrow et al. | 364/413.02 |
| 5,012,411 | 4/1991 | Policastro et al. | 364/413.06 |
| 5,016,172 | 5/1991 | Dessertine | 364/413.02 |
| 5,018,067 | 5/1991 | Mohlenbrock et al. | 364/413.02 |
| 5,019,974 | 5/1991 | Beckers | 364/413.02 |
| 5,024,225 | 6/1991 | Fang | 128/630 |
| 5,036,852 | 8/1991 | Leishman | 128/630 |
| 5,142,484 | 8/1992 | Kaufman et al. | 222/638 |
| 5,263,491 | 11/1993 | Thornton | 128/774 |
| 5,301,105 | 4/1994 | Cummings, Jr. | 364/401 |
| 5,307,263 | 4/1994 | Brown | 364/413.09 |

(List continued on next page.)

*Primary Examiner*—Cary E. O'Connor
*Assistant Examiner*—Eric F. Winakur
*Attorney, Agent, or Firm*—Christie, Parker & Hale, LLP

[57] ABSTRACT

A therapeutic behavior modification program, compliance monitoring and feedback system includes a server-based relational database and one or more microprocessors electronically coupled to the server. The system enables development of a therapeutic behavior modification program having a series of milestones for an individual to achieve lifestyle changes necessary to maintain his or her health or recover from ailments or medical procedures. The program may be modified by a physician or trained case advisor prior to implementation. The system monitors the individual's compliance with the program by prompting the individual to enter health-related data, correlating the individual's entered data with the milestones in the behavior modification program and generating compliance data indicative of the individual's progress toward achievement of the program milestones. The system also includes an integrated system of graphical system interfaces for motivating the individual to comply with the program. Through the interfaces, the individual can access the database to review the compliance data and obtain health information from a remote source such as selected sites on the Internet. The system also provides an electronic calendar integrated with the behavior modification program for signaling the individual to take action pursuant to the behavior modification program in which the calendar accesses the relational database and integrates requirements of the program with the individual's daily schedule, and an electronic journal for enabling the individual to enter personal health-related information into the system on a regular basis. In addition, the system includes an electronic meeting room for linking the individual to a plurality of other individuals having related behavior modification programs for facilitating group peer support sessions for compliance with the program. The system enables motivational media presentations to be made to the individuals in the electronic meeting room as part of the group support session to facilitate interactive group discussion about the presentations. The entire system is designed around a community of support motif including a graphical electronic navigator operable by the individual to control the microprocessor for accessing different parts of the system.

34 Claims, 60 Drawing Sheets

U.S. PATENT DOCUMENTS

| | | | |
|---|---|---|---|
| 5,322,069 | 6/1994 | Gallant et al. | 128/700 |
| 5,331,549 | 7/1994 | Crawford, Jr. | 364/413.02 |
| 5,339,821 | 8/1994 | Fujimoto | 128/700 |
| 5,357,427 | 10/1994 | Langen et al. | 364/413.02 |
| 5,361,755 | 11/1994 | Schraag et al. | 128/630 |
| 5,377,258 | 12/1994 | Bro | 379/93 |
| 5,390,238 | 2/1995 | Kirk et al. | 379/93 |
| 5,410,471 | 4/1995 | Alyfuku et al. | 364/413.02 |
| 5,425,699 | 6/1995 | Speigel | 600/26 |
| 5,437,278 | 8/1995 | Wilk | 128/653.1 |
| 5,441,047 | 8/1995 | David et al. | 128/670 |
| 5,442,728 | 8/1995 | Kaufman et al. | 395/2.79 |
| 5,447,164 | 9/1995 | Shaya et al. | 128/710 |
| 5,462,051 | 10/1995 | Oka et al. | 128/630 |
| 5,473,537 | 12/1995 | Glazer et al. | 364/419.2 |
| 5,524,645 | 6/1996 | Wills | 128/898 |
| 5,542,420 | 8/1996 | Goldman et al. | 128/630 |
| 5,544,649 | 8/1996 | David et al. | 128/630 |
| 5,544,661 | 8/1996 | Davis et al. | 128/700 |
| 5,553,609 | 9/1996 | Chen et al. | 128/630 |
| 5,576,952 | 11/1996 | Stutman et al. | 364/413.02 |
| 5,590,648 | 1/1997 | Mitchell et al. | 128/630 |
| 5,596,994 | 1/1997 | Bro | 128/732 |
| 5,612,869 | 3/1997 | Letzt et al. | 395/203 |
| 5,623,939 | 4/1997 | Garfield | 128/733 |
| 5,633,910 | 5/1997 | Cohen | 379/38 |
| 5,673,691 | 10/1997 | Abrams et al. | 600/300 |

Fig. 2

HeartLand Prescription Form

| Patient Name | Patient ID | Date | Physician Name | Physician ID |
|---|---|---|---|---|
|  |  |  |  |  |

1. Fill in diagnosis:

| Patient Diagnosis | Co-morbid Diagnosis |
|---|---|
|  |  |

2. Circle a diagnostic category:

| Category | Diagnosis | Level 1 (mos.) | Level 2 (mos.) | Level 3 (mos.) | Health and Wellness |
|---|---|---|---|---|---|
| I | Current year MI survivor | 3 | 3 | 6 | Contin.>12th month |
| II | Current year alt. to PTCA or CABG | 3 | 3 | 6 | Contin.>12th month |
| III | Current year diagnosed CAD | 3 | 3 | 6 | Contin.>12th month |
| IV | All diagnosed Angina | 3 | 3 | 6 | Contin.>12th month |
| V | Prior years' post MI/surgical--High Risk | 3 | 3 | 6 | Contin.>12th month |
| VI | Prior years' post MI/surgical--Low Risk | 1 | 1 | 10 | Contin.>12th month |
| VII | 2 or more Risk factors | 0 | 2 | 4 | Contin.>12th month |
| VIII | Health and Wellness | 0 | 0 | 0 | Continuous |

3. Please circle as appropriate:

Does the patient need smoking cessation?   Yes   No
Have you prescribed nicotine patch or gum?   Yes   No
Does the patient need weight reduction?   Yes   No   If yes, target weight:____

4. What are patient's current and prescribed medications?

| Medication | Standard Dosage | Comments/Changes |
|---|---|---|
| HCTZ | 25 mg |  |
| Atenolol | 50 mg |  |
| Lisinopril | 20 mg |  |
| Atorvastatin | 20 mg |  |
| Antioxidant: Vitamin E | 400 IU |  |
| Antioxidant: Vitamin C | 500 mg |  |
| Other: |  |  |
| Other: |  |  |
| Other: |  |  |
| Other: |  |  |

5. Circle or fill in desired 3-month targets:

| Daily Calories | 1200 | 1500 | 2000 | 2500 | 3000 |
|---|---|---|---|---|---|
| Sat Fat Grams | <15 | 15 | 18 | 20 | 25 |
| Pct Fat Cal | 10% | 15% | 20% | 25% | 30% |
| Exercise (Freq/wk/RPE) | 20/5x/3 | 30/5x/4 | 45/5x/5 | 50/5x/6 | 60/5x/7 |
| Max Heart Rate |  |  |  |  |  |
| Stress Reduction Needs | Low Need | Some | Definite | High | Very High |
| Lipid Level Target |  |  |  |  |  |
| Total Cholesterol | 140 | 150 | 175 | 200 | <225 |
| LDL | 60 | 70 | 80 | <100 | <125 |
| HDL | 35 | 37 | 39 | 41 | >42 |

Physician's Signature:_____     Telephone:_____

FAX THIS FORM TO SALUS MEDIA: (805) 969-3601
You will receive Fax confirmation within 24 Hours. For Assistance please call: (805) 969-2234

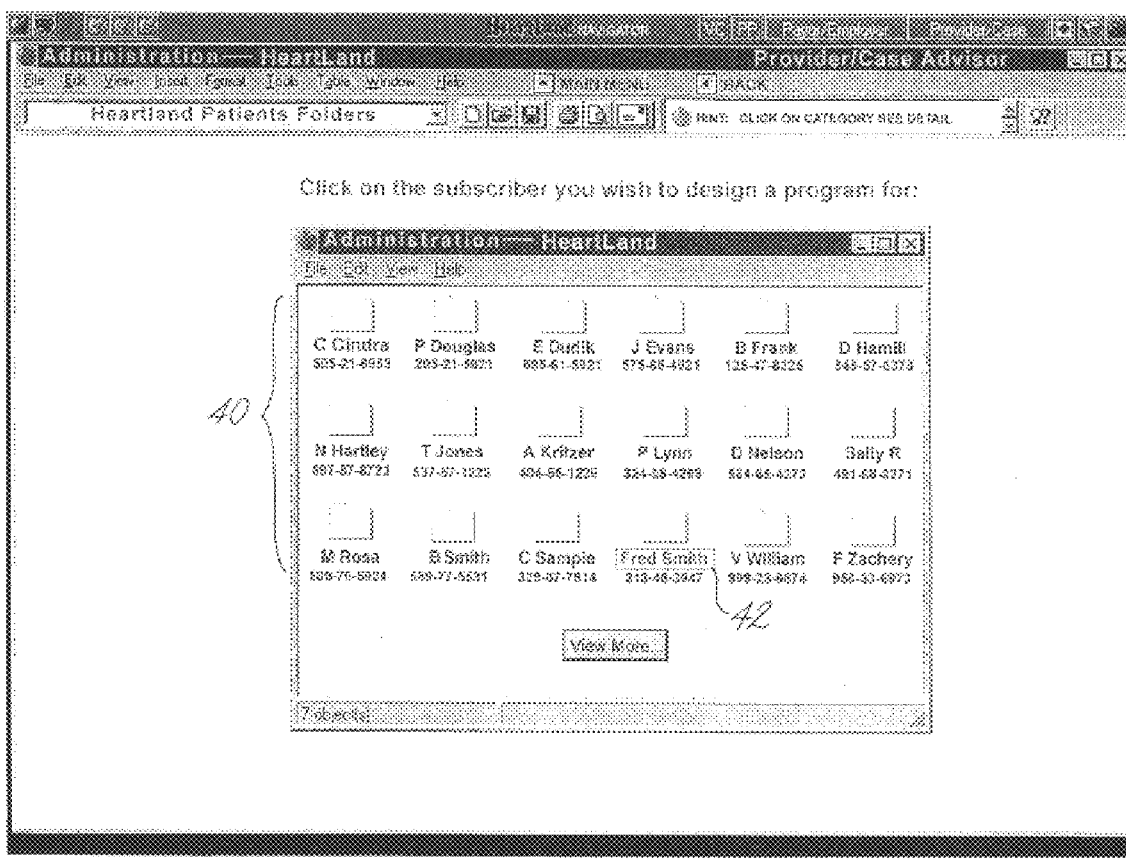

| PATIENT STATUS & GOALS DETAILS | | | Nov 2/10/98 | 1 month Goal | GOALS |
|---|---|---|---|---|---|
| Name / D.O.B. | Fred Smith | 2-5-45 | | | |
| Starting Date | 2/1/98 | | | | |
| Heartland I.D. | 23-642 | | | | |
| Height / Sex | 5'8" | Male | | | |
| Weight | 182 | | 182 | | |
| BMI | 28.28 | | 28.28 | | |
| Smoke | .5 | Packs/Day | .5 | | |
| Physical Activity | 6 / 0 / 3 | minutes / x-week / RPE | 20 / 3 / 3 | | |
| Alcohol | 2 | Average Drinks per Day | 2 | | |
| Eating Habits | 40 | %Fiber/Cmplx Carb Intake | 50 | | |
| | 40 | %Fatty Food Intake | 20 | | |
| | 40 | %Fatty Dairy Intake | 10 | | |
| Calories | 3,600 | | 3,300 | | |
| Fat Calories & % | 45% | | 1,800 | | |
| Cholesterol - LDL | 142 | | 140 mg/dl | | |
| Cholesterol - HDL | 35 | | 37 mg/dl | | |
| Cholesterol | 246 | mg/dl | 228 | | |
| Resting Pulse Rate | 68 | Beats Per Minute | 65 | | |
| Stress | 8.5 Scale of 1 to 10 (10 being high stress) | | 7.0 | | |
| Depression | Scale of 1 to 10 (10 being greatest) | | 10 | | |
| Blood Pressure | 140/100 | systolic/diastolic | 140/100 | | |
| Seatbelt Use | 30 | percent of time | 50 | | |
| Back Pain | | incidents per month | 3 | | |
| Pharmaceuticals | | | | | |
| - aspirin | 325 | mg | 325 mg/d | | |
| - hydrochlorathzd. | 12.5 | mg | 12.5 mg/d | | |
| - Lovastatin | 20 | mg | 20 mg/d | | |

| HeartLand Patient Progress Report |
|---|

Date: April 2, 1997

Dear Doctor Cavello:

This is a status report on your patient, Fred Smith, SSN: 565-76-2334, Plan No. 011-066754

Your diagnosis was: non-complicated anterior MI and co-morbid diagnosis none.

Patient entered the HeartLand program on March 12, 1997. He/she has been on the program 3 weeks.

Progress toward goals:

| Parameter | Current Status | Suggested Next Steps | Target |
|---|---|---|---|
| Blood Pressure | 146/92 | 144/90 | 140/90 |
| Weight | 172 | 170 | 170 |
| Resting Pulse | 67 | 65 | 65 |
| Exercise Program | 35 min/4x-wk/4 RPE | 45 min/4x-wk/5 RPE | 45 min/6x-wk/6 RPE |
| Total Cholesterol | 210 mg/dl | 200 mg/dl | 190 mg/dl |
| LDL Cholesterol | 125mg/dl | 115mg/dl | 100mg/dl |
| HDL Cholesterol | 39mg/dl | 42mg/dl | 45mg/dl |
| Diet: Cal/day | 3100 | 3000 | 2800 |
| Sat Fat grams/day | 20 g | 15 g | 10 g |
| Smoking Status | 0 was: .5 pack/day | 0 | 0 |
| Aspirin | 325 mg - missed 1/wk | 325 mg - missed 0/wk | 325 mg - missed 0/wk |
| HCTZ | 12.5 mg. - missed 0/wk | 1205 mg. - missed 0/wk | 12.5 mg. - missed 0/wk |
| Lovastatin | 20 mg. - missed 0/wk. | 20 mg. - missed 0/wk. | 20 mg. - missed 0/wk. |
| Other | | | |
| Other | | | |
| Other | | | |

Please initial here to indicate you have reviewed this Status Report: _____

Please initial here to indicate you agree with suggested next step targets: _____

Indicate any changes desired in Next Step Goals and Medications:

_____

_____

Physician's Signature:_____

Thank you,

Mary Quinn
HeartLand Case Advisor

FAX THIS FORM TO SALUS MEDIA: FAX NO. (805) 969-3601
You will receive Fax confirmation within 24 Hours. For Assistance please call (805) 969-2234

Creating Your Sanctuary

One of the first things you should do when you start using creative visualization is to create a sanctuary within yourself where you can go anytime you want to. Your sanctuary is your ideal place of relaxation, tranquility, and safety and you can create it exactly as you want it.

Close your eyes and relax in a comfortable position. Imagine yourself in some beautiful natural environment. It can be anyplace that appeals to you . . . in a meadow, on a mountaintop, in the forest, beside the sea. It could even be under the ocean, or on another planet. Wherever it is, it should feel comfortable, pleasant, and peaceful to you. Explore your environment, noticing the visual details, the sounds and smells, any particular feelings or impressions you get about it.

Now do anything you would like to do to make the place more homelike and comfortable. You might want to build some type of house or shelter there, perhaps just surround the whole area with a golden light of protection and safety, create and arrange things there for your convenience and enjoyment, or do a ritual to establish it as your special place.

From now on this is your own personal inner sanctuary, to which you can return anytime just by closing your eyes and desiring to be there. You will always find it healing and relaxing to be there. It is also a place of special power for you, and you may wish to go there every time you do creative visualization.

You may find that your sanctuary spontaneously changes from time to time, or that you want to make changes and additions to it. You can be very creative in your sanctuary and have a lot of fun there . . . just remember to retain the primary qualities of peacefulness, tranquility, and a feeling of absolute safety.

DETERMINING YOUR TARGET HEART RATE ZONE

1. Take your pulse on your neck or wrist.

2. Subtract your age from 220.　　　　220
　　　　　　　　　　　　　　　　　-40 Sample Age
　　　　　　　Maximum heart rate　180

3. Multiply maximum heart rate by .55　x.55
　　　　　　　Lower heart rate limit　　99

4. Multiply maximum heart rate by .85　180
　　　　　　　　　　　　　　　　　x.85
　　　　　　　Upper heart rate limit　153

5. Your target heart rate zone is definined by lower
   and upper heart rate limits.

TO SEE IF YOU ARE IN YOUR TARGET HEART RATE ZONE

Take your pulse for :10 seconds
and multiply that number by six.
This should be in your
Target Heart Rate Zone.

| Category | Description | Total Eligible | Participating | | Compliant | | Probation | | Terminated | |
|---|---|---|---|---|---|---|---|---|---|---|
| | | | No. eligible | Pct. eligible | No. | Pct. | No. | Pct. | No. | Pct. |
| Category I | Current-Year MI Survivors | 1,008 | 105 | 10.4% | 87 | 82.9% | 13 | 12.4% | 5 | 4.8% |
| Category II | Current-Year Bypass & Angioplasty | 733 | 76 | 10.4% | 59 | 77.6% | 10 | 13.2% | 7 | 9.2% |
| Category III | Current-Year Diagnosed CAD, Surgery Rec | 740 | 71 | 9.6% | 63 | 88.7% | 5 | 7.0% | 3 | 4.2% |
| Category IV | All Diagnosed Angina | 6,726 | 706 | 10.5% | 553 | 78.1% | 84 | 11.9% | 71 | 10.0% |
| Category V | Prior-Years' MI & Post-Surgical - High Risk | 2,183 | 680 | 31.1% | 595 | 85.0% | 38 | 6.8% | 57 | 8.4% |
| Category VI | Prior-Years' MI & Post-Surgical - Low Risk | 6,547 | 227 | 3.5% | 187 | 82.4% | 22 | 9.7% | 18 | 7.9% |
| Category VII | (2 or more factors) | 75,826 | 3,191 | 4.2% | 2,765 | 86.6% | 148 | 4.6% | 278 | 8.7% |
| Category VIII | Wellness Program | 125,714 | 7,920 | 6.3% | 6,267 | 79.1% | 1,359 | 17.2% | 294 | 3.7% |
| Grand Totals & Percent Averages | | | 12,976 | | 10,586 | 81.6% | 1,679 | 12.9% | 733 | 5.6% |

Fig. 50

| Category | Description | Number on Program | Heartland Group Medical Costs | Heartland Program Costs | TOTAL HEARTLAND COSTS | Control Group Medical Costs | Heartland Savings |
|---|---|---|---|---|---|---|---|
| Category I | Current-Year MI Survivors | 105 | 253,385 | 181,850 | 435,035 | 589,221 | 154,208 |
| Category II | Current-Year Bypass & Angioplasty | 76 | 140,678 | 122,360 | 263,038 | 327,153 | 64,117 |
| Category III | Current-Year Diagnosed CAD, Surgery Rec | 77 | 240,702 | 133,210 | 373,912 | 559,772 | 185,868 |
| Category IV | All Diagnosed Angina | 708 | 1,139,172 | 1,047,840 | 2,187,012 | 2,649,237 | 462,225 |
| Category V | Prior-Years' MI & Post-Surgical - High Risk | 580 | 1,840,840 | 1,006,400 | 2,847,240 | 3,815,907 | 1,158,667 |
| Category VI | Prior-Years' MI & Post-Surgical - Low Risk | 227 | 420,177 | 197,490 | 617,667 | 977,153 | 359,465 |
| Category VII | (2 or more factors) | 3,191 | 2,003,948 | 717,975 | 2,721,923 | 4,680,344 | 1,938,421 |
| Category VIII | Wellness Program | 7,920 | 2,304,720 | - | 2,304,720 | 6,359,814 | 3,855,094 |
| TOTALS | | 12,984 | 8,343,600 | 3,806,825 | 11,850,525 | 19,938,605 | 7,388,089 |

Fig. 51

THERAPEUTIC BEHAVIOR MODIFICATION PROGRAM, COMPLIANCE MONITORING AND FEEDBACK SYSTEM

CROSS REFERENCE TO RELATED APPLICATIONS

This application claims the benefit of U.S. provisional patent application numbers 60/029,862, filed Nov. 1, 1996, and 60/052,222, filed Jul. 11, 1997, the contents of both of which are hereby incorporated by reference.

FIELD OF THE INVENTION

The present invention relates generally to a computer-implemented system for promoting wellness and improving health, and more particularly to a therapeutic behavior modification program, compliance monitoring and feedback system.

BACKGROUND OF THE INVENTION

One of the most difficult and costly areas of health care, education, and rehabilitation involves the need for individuals to modify their behavior to prevent or recover from medical ailments. Heart disease, stroke, diabetes, asthma, chronic pain, depression, addiction, cancer and a wide variety of other ailments have been clinically shown to respond well to lifestyle modification, including changes to diet, exercise patterns, and stress levels. Patients who are recovering from a surgical procedure such as heart bypass surgery or are suffering from diabetes, for example, must often make lifestyle changes in order to survive.

When individuals are successful in making and adhering to positive lifestyle changes, they frequently require fewer physician visits, go to the hospital less often, and have fewer surgeries. Long term medical costs go down accordingly.

At present, many programs for helping patients make lifestyle changes involve a doctor's visit and distribution of a brochure describing the health benefits of behavior modification and lifestyle change. This method is often ineffective in modifying behavior because there is little or nothing in the way of an on-going support mechanism to assist the patient in complying with recommendations, insufficient means for motivating the patient to make recommended changes, and insufficient means for monitoring compliance with such recommendations. Participation in an on-going support program is often effective for patients who have undergone surgery and must make subsequent lifestyle changes, but currently available in-person programs involve costly medical staff and facilities. It can also be inconvenient for the patient to travel to such programs on a regular basis. Because of their cost and the potential for inconvenience, many support programs last for only a limited time, which is often insufficient for the patient to modify behavior thoroughly and effectively.

Another disadvantage of existing lifestyle modification programs is the lack of information readily available to the physician regarding the patient's compliance with the program. With the present push toward low cost yet high quality health care, a system by which a physician could readily access information on patient compliance has clear benefits.

The development of a therapeutic program that could effectively motivate patients to modify their behavior and change their lifestyles to prevent or recover from ailments, and could be delivered to them electronically at home, work, or while traveling, would be highly desirable. It would also be desirable for such a system to enable physicians and their staffs to receive frequent feedback regarding patients' compliance with their programs. It would be further desirable if such a system allowed for aggregate reviews of such information by health plan payors, such as HMOs, insurance companies, and large self-insured employers, for the purpose of enhancing the efficiency of managed health care.

SUMMARY OF THE INVENTION

The present invention therefore provides for an integrated, computer-implemented, electronically deliverable patient therapeutic behavior modification program, compliance, monitoring, and feedback system which supports the design of customized therapeutic behavior and lifestyle modification programs for subscribers; accepts the input of current health data for these patients; enables the review of these health records by a physician; enables the performance of aggregate reviews of such records by health plan payors, such as HMOs, insurance companies, and large self-insured employers; and motivates the patient to comply with the program and make the necessary lifestyle changes through an integrated system of interactive graphical interfaces.

In an exemplary scenario, a physician prescribes parameters and goals for a such a therapeutic behavior modification program to help a patient recover from an ailment or surgical procedure, and these are input into the computer-implemented system. Alternately, one of several established behavior modification programs that have been designed for patient recovery from particular ailments or procedures can be utilized. The system provides a novel interface that allows immediate patient access to the behavior modification program and helps monitor compliance with the program by prompting the patient to input data relating to his or her adherence to the program's parameters. These parameters may relate, for example, to diet, exercise, and other factors pertinent to the behavior modification program. The patient, physician, case manager or members of the physician's staff may also input information relating to blood pressure, medication, and the results of other medical tests on a computer linked to the system. Using this input, the system can recommend a plan (also referred to as a therapeutic program) and goals based on established medical protocols. The physician can modify the program to customize it for the patient. Once the patient has begun to follow the program, the system recommends modifications and updates to both physician and patient by correlating the patient's progress with previously established goals.

The system provides ongoing multimedia (audio, video, and e-mail) feedback to the patient through a novel, user-friendly interface designed around an interactive "village" or "community of support" motif that allows him or her to navigate electronically through different parts of the system. The interface provides access to pertinent medical information, an on-line journal that enables the patient to write down his or her feelings on a regular basis, an electronic calendar which integrates events mandated by the program with the patient's daily schedule, on-line interactive group support sessions with patients on similar programs, and motivational multimedia presentations. The system can make specific diet and exercise suggestions based on the patient's overall program. This data is monitored by a professional case advisor—a nurse trained in the protocols of the system's software—as well as electronically by the system's protocols themselves. The system provides specific feedback to the physician so that he or she can modify or update the program as the patient progresses; and in the aggregate to the health plan payor to assess management and cost factors. The health plan payor can also view individual records which are obtainable after receiving the proper medical release from the patient. By providing several channels of continuous feedback among the patient, physician, professional case advisor, and health plan payor through custom designed interfaces, the system helps enhance patient compliance with the behavior modification program, and can help make the overall health care system more efficient.

BRIEF DESCRIPTION OF THE DRAWINGS

These and other aspects of the present invention will become more apparent from the following Detailed Description of a presently preferred embodiment of the present invention read in conjunction with the accompanying drawings and exhibits, in which:

FIG. 2 is an exemplary prescription form for inputting a patient's baseline vital factors;

FIG. 3 is a graphical representation of a set of files for patients for whom recovery programs may be designed or modified;

FIG. 4 is a graphical representation of an exemplary patient file taken from among those represented in FIG. 3;

FIG. 5 is a graphical representation corresponding to the program Design option of FIG. 4;

FIG. 6 is a graphical representation corresponding to the Program Detail option of FIG. 5;

FIG. 7 is an exemplary patient progress report;

FIG. 11 is an expanded graphical representation of the Schedule Book;

FIG. 13 is an expanded graphical representation of the Journal;

FIG. 18 is a graphical representation of the system's Postcard option;

FIG. 30 is a graphical representation of the system's Relaxation option;

FIG. 34 is a graphical representation of a World Wide Web access option;

FIG. 35 is a graphical representation of an educational topic available through a pull down menu in FIG. 32;

FIG. 40 is a graphical representation of an exemplary patient file;

FIG. 45 is a graphical representation of the system's Behavior option;

FIG. 46 is a graphical representation of the system's Recommend option;

FIG. 47 is an expanded graphical representation of the system's Communicate option;

FIG. 50 is a graphical representation of a View Compliance Status option;

FIG. 51 is a graphical representation of a View Comparative Costs option;

Figure 60:
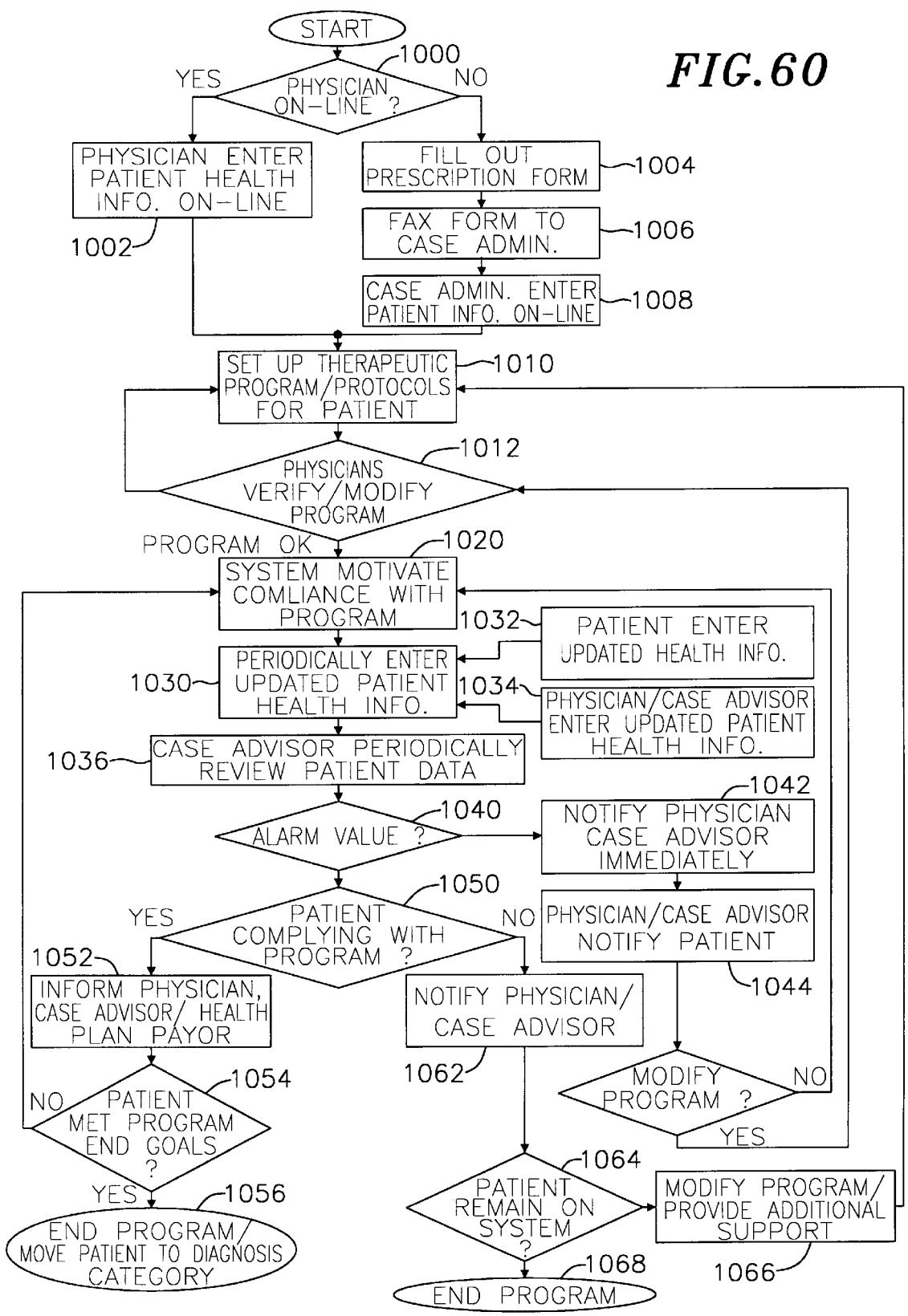
FIG. 60 is a flow diagram illustrating certain aspects of the therapeutic behavior modification program's compliance monitoring and feedback system.

To facilitate description of the present invention, reference is made in numerous instances to the flow diagram of FIG. 60. For convenience, the blocks in the flow diagram are numbered beginning at 1000.

DETAILED DESCRIPTION OF THE INVENTION

Figure 1:
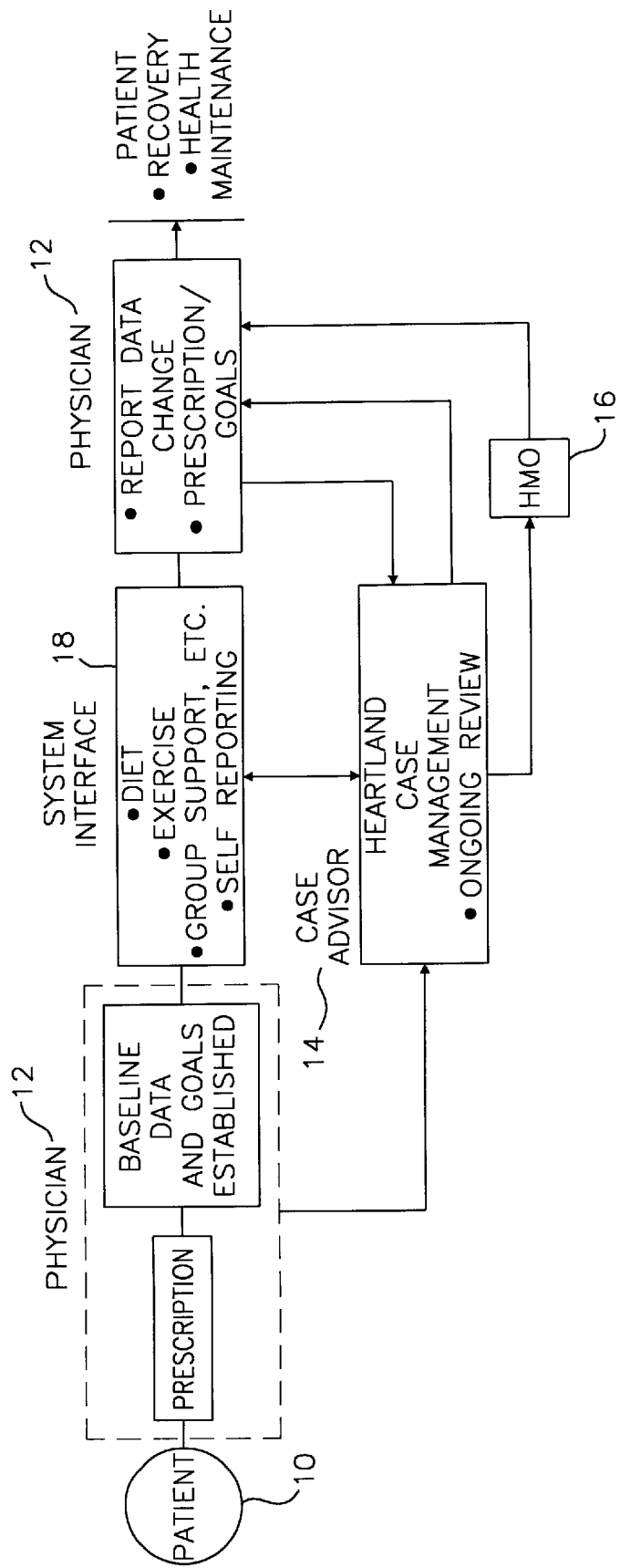
FIG. 1 is a block diagram illustrating how feedback and monitoring is used in the current embodiment of the therapeutic behavior modification program's compliance monitoring and feedback system

Referring to FIG. 1, in a presently preferred embodiment of the invention, the patient 10, physician 12, case advisor 14, and health plan payor 16 (such as an HMO, insurance company or self-insured employer), all provide input to and/or receive output from the therapeutic behavior modification program's compliance monitoring and feedback system. The case advisor may be a doctor, nurse, and/or other trained medical professional experienced in case management protocols and practices. Patients electronically interact with the system, the case advisor and their doctor through the system interface 18. The behavior modification program is customized to fit the health care and recovery needs of individual patients. The system provides at least two separate benefits: it helps the patient comply with the program through an electronically-implemented support mechanism; and further assists in monitoring such compliance.

A wide range of individuals can benefit from the system. By way of example only, these individuals include those with chronic ailments such as coronary artery disease, diabetes, chronic pain, depression, addiction, arthritis, cancer and asthma, as well as patients who are recovering from medical procedures such as angioplasty or by-pass surgery (the "clinical group").

Individuals who simply want to maintain their health and prevent or reduce the risk of such ailments (the "wellness group") can also benefit from the program. For these individuals, the program may be focused on stress management, diet, and exercise. The wellness group may further include family members of the clinical group who may need group support and/or counseling in dealing with the family member's chronic illness.

The members of the wellness group may not need all the features available to members of the clinical group. Furthermore, access to certain areas within the system may be limited and/or customized to meet the individual user's needs. However, wellness group members may choose to use the case management functions as a "virtual coach." For example, an individual may want to have a case advisor assist them in losing weight by helping the individual change his or her nutrition, exercise and stress management habits. The "virtual coach" or case advisor, can provide ongoing feedback and encouragement throughout the process. Wellness participants may also choose to join an on-line support group to help them achieve their health and wellness goals.

In an exemplary scenario, a physician diagnoses an individual with an ailment. The physician may then recommend a health care maintenance or recovery program which requires the patient to: take certain medications; participate in a support group; and control risk factors by altering his or her diet, following an exercise program, and managing stress levels.

The physician can then place the patient on the system to help him or her make these desirable or necessary lifestyle and behavior modifications. In order to subscribe the patient to the system, his or her baseline vital factors are entered. Such factors may include blood pressure readings, heart rate, height, weight, and cholesterol levels. Depending on whether the doctor is on-line (block 1000, FIG. 60), The doctor may input these vital factors into the system directly via his or her personal computer (block 1002, FIG. 60). Alternatively, the physician may fill out a prescription form and send the information to a case advisor, who then sets the patient up on the system (blocks 1004, 1006 and 1008, FIG. 60).

Referring to FIG. 2, an exemplary prescription form 22 contains identification information 23 such as the patient's name and identification. Using the form, the physician selects a diagnostic category 24 and prescribes a recovery program level 26. In the exemplary embodiment, eight separate diagnostic categories exist that correspond to the state of the patient's health. Category I, for example, includes patients who have suffered from a heart attack within the current year, while Category VIII includes patients who suffer from no particular ailment but are on the plan simply to promote wellness. Other categories may also be added as necessary.

Depending on the diagnosis, the physician may recommend that the patient cease smoking or that he or she lose a targeted amount of weight within a certain period by circling the appropriate response in field 30. The physician may also enter other information, such as the patient's medications 32. The physician then circles or fills in desired 3-month targets 34 relating to, among other things, daily calorie intake, percent daily intake of saturated fat, maximum heart rate, and cholesterol level.

Referring to FIG. 3, the case administrator sets up a new patient based on information contained in the patient prescription form or accesses the records of existing patients through patient files 40. In this example, the patient files 40 are identified by the patient's name and social security number. To create or modify the program for a particular patient, the administrator creates a new folder or selects a preexisting folder 42 corresponding to the patient in question.

Once the physician or case administrator enters the patient into the system, either the system or case advisor recommends a default set of goals based on the patient's needs and existing medical protocols that may be modified by the physician (blocks 1010 and 1012, FIG. 60). FIG. 4 illustrates an exemplary patient record after selection of the desired patient file 42 in FIG. 3. The record includes, among other things, the patient's current status and program goals. The first column 44 of the record sets forth fields for pertinent patient information including the patient's vital signs (e.g., weight, cholesterol level, blood pressure), other baseline characteristics (e.g., patient's smoking habit, physical activity, alcohol and eating habits, depression and stress levels, seat belt use), and information relating to any medications used by the patient. The second column 46 of the record sets forth the baseline values corresponding to the vital signs and patient characteristics at the beginning of his or her participation in the program. As shown in the third column 48, the record may be updated on an ongoing basis by taking data from the patient on-line and from subsequent office visits. Based on the patient's initial evaluation and/or short-term progress, the physician or case advisor can design a new program or modify an existing program for the patient by selecting the system's Design option 50.

Figure 5:
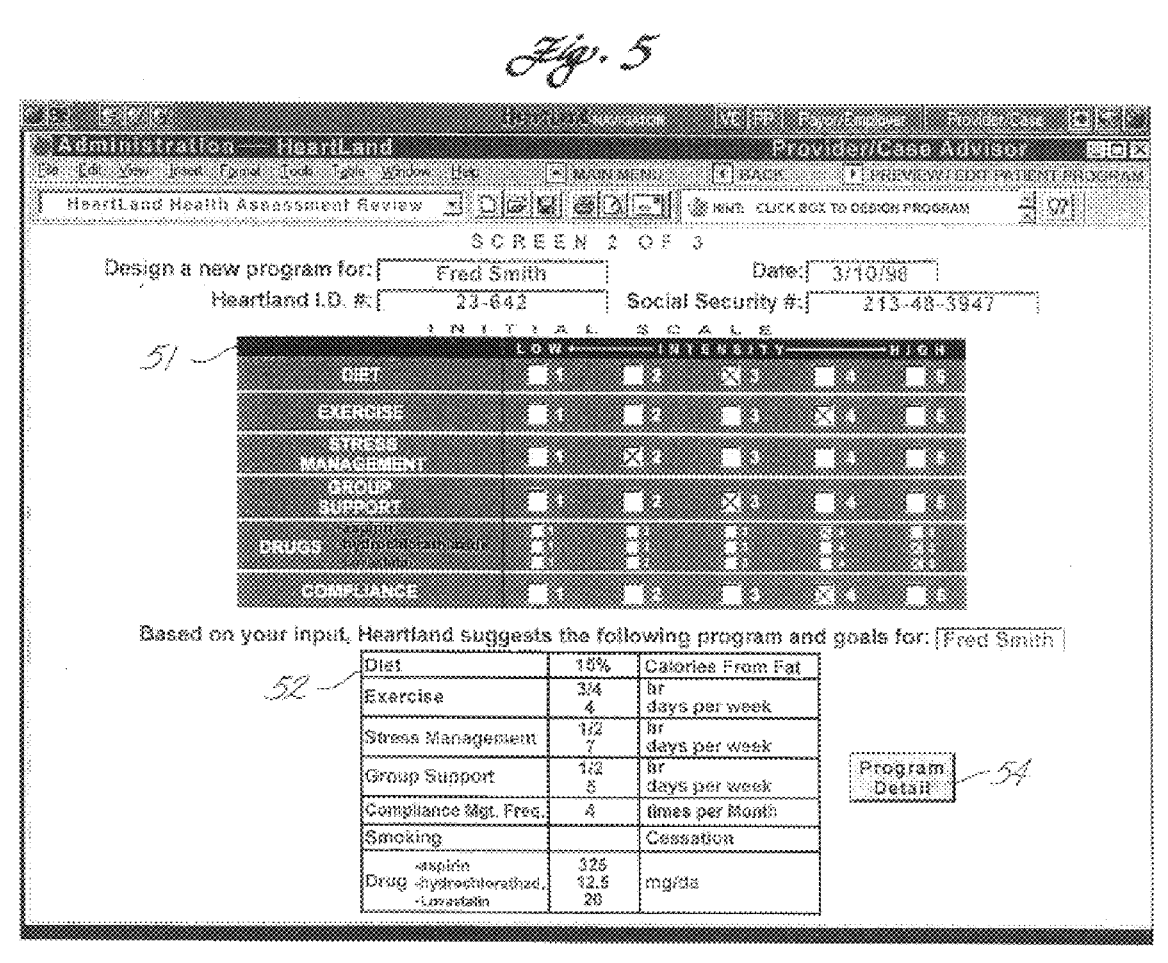

Referring to FIG. 5, upon selection of the Design option 50 in FIG. 4, the system prompts the physician or case advisor to assign intensity levels 51 corresponding to the patient's diet, exercise, stress management, need for group support, anticipated compliance, and pharmaceutical requirements. The intensity levels in this example range from a lowest level of 1 to a highest level of 5. Other measures of program intensity may also be included.

Based on the input information, the system, case advisor or physician generates a set of goals 52 or milestones for the patient. This is done by correlating patient information such as age, sex, weight and information relating to the health, life situation and diagnostic category of the patient to established medical protocols for that type of patient. Other pertinent information that may be taken into account includes the patient's medication and other health conditions. Based on the correlation, the system suggests a therapeutic program including goals relating to intake of calories from fat, exercise level, stress management counseling, and group support and compliance management frequency. The physician or case advisor may view details as to how the suggested goals may be implemented by selecting the system's Program Detail option 54.

Figure 6:
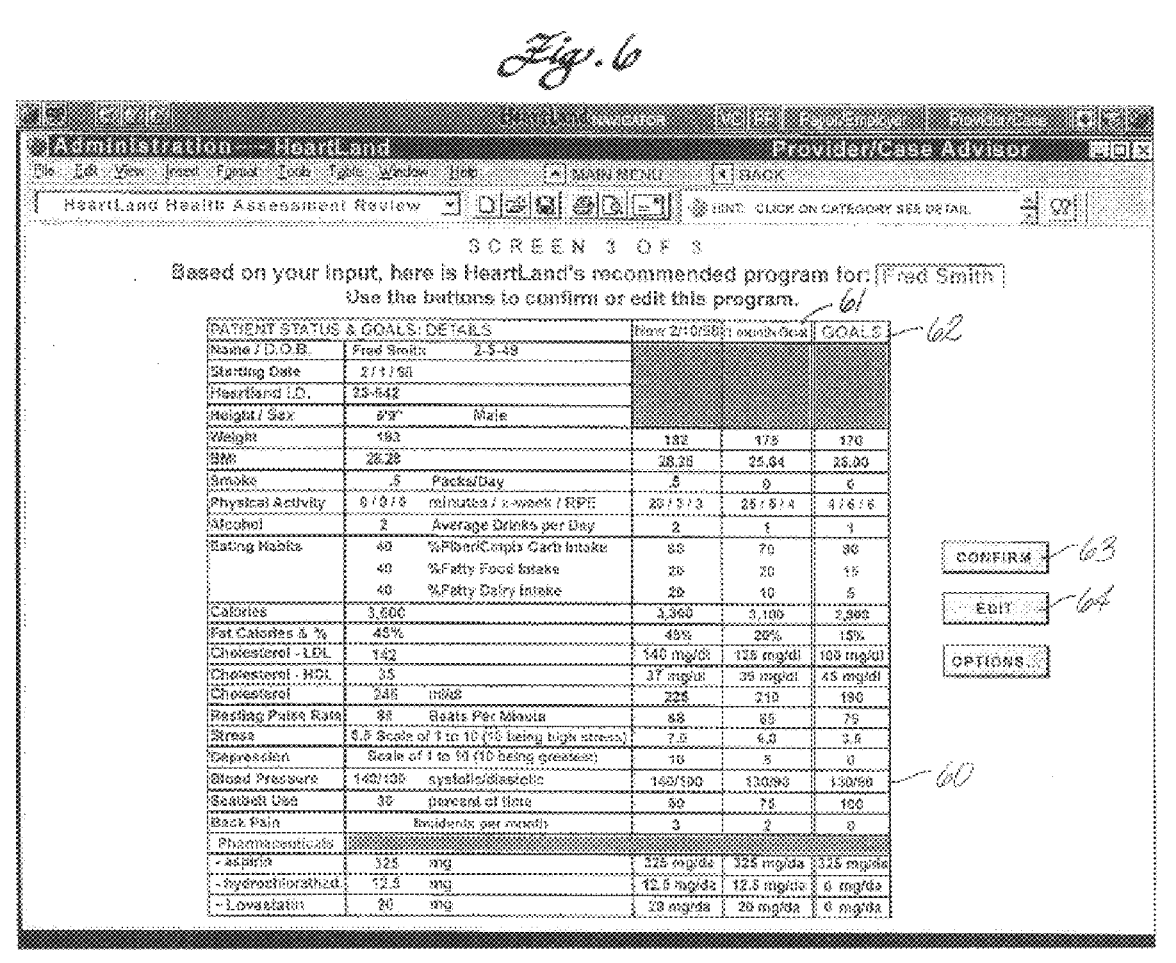

Referring to FIG. 6, upon selection of the Program Detail option 54, the patient record 60 is presented along with the recommended one month goals 61 and final goals 62. The physician or case advisor may confirm 63 or edit 64 the suggested program to modify the goals by making appropriate selections (block 1012, FIG. 60).

The content of the patient records and the generated goals vary depending on the patient's diagnostic category. For example, some of the information shown on the patient record may not be necessary for an individual belonging to the wellness group. Information regarding calories, cholesterol level, blood pressure, and seat belt use, for instance, may not pertain to a person who is on the system to get support to help deal with a family member who suffers from a chronic ailment.

Referring to FIG. 7, the system also sends an exemplary patient status report 70 to physicians who do not have direct access to the system. The status report may include information regarding a patient's current status 66, suggested next steps 67, and target goals 68. Other information may also be included in the status report as desired by the physician. The physician has the option to agree with the suggested next steps 69 or indicate changes to the program. The physician then sends the report 70 back to the case advisor for modification of the program as necessary. Communication may take place via e-mail, facsimile, or any other method of transferring data.

Once the patient is set up on the system, it assists him or her in complying with his or her behavior modification program (block 1020, FIG. 60). To use the program, the patient logs into the system network via telephone line, cable modem, cellular connection, satellite link or other communication method that allows for a connection into a network server.

Figure 8:
FIG. 8 is a graphical representation of various interface tools, organized around a village motif, available to a clinical group patient.

Referring to FIG. 8, in a presently preferred embodiment of the invention, the user interface for patients in the clinical and wellness groups is organized around a village motif. The user progresses through the system by following paths through a graphically represented town square to destinations including the village gymnasium 71, tranquility park 72, post office 74, coffee shop 76, store 78, library 80, travel agency 82, as well as the user's own "home" 84. The village motif presents the patient with an image of a community of support. The entire on-line community revolves around his or her recovery and well-being, and this helps bolster the patient's confidence and motivation. Furthermore, the village motif provides an easy-to-understand representation of the system's structure. The patient learns to navigate the system more quickly and easily because of the intuitive town layout.

Figure 37:
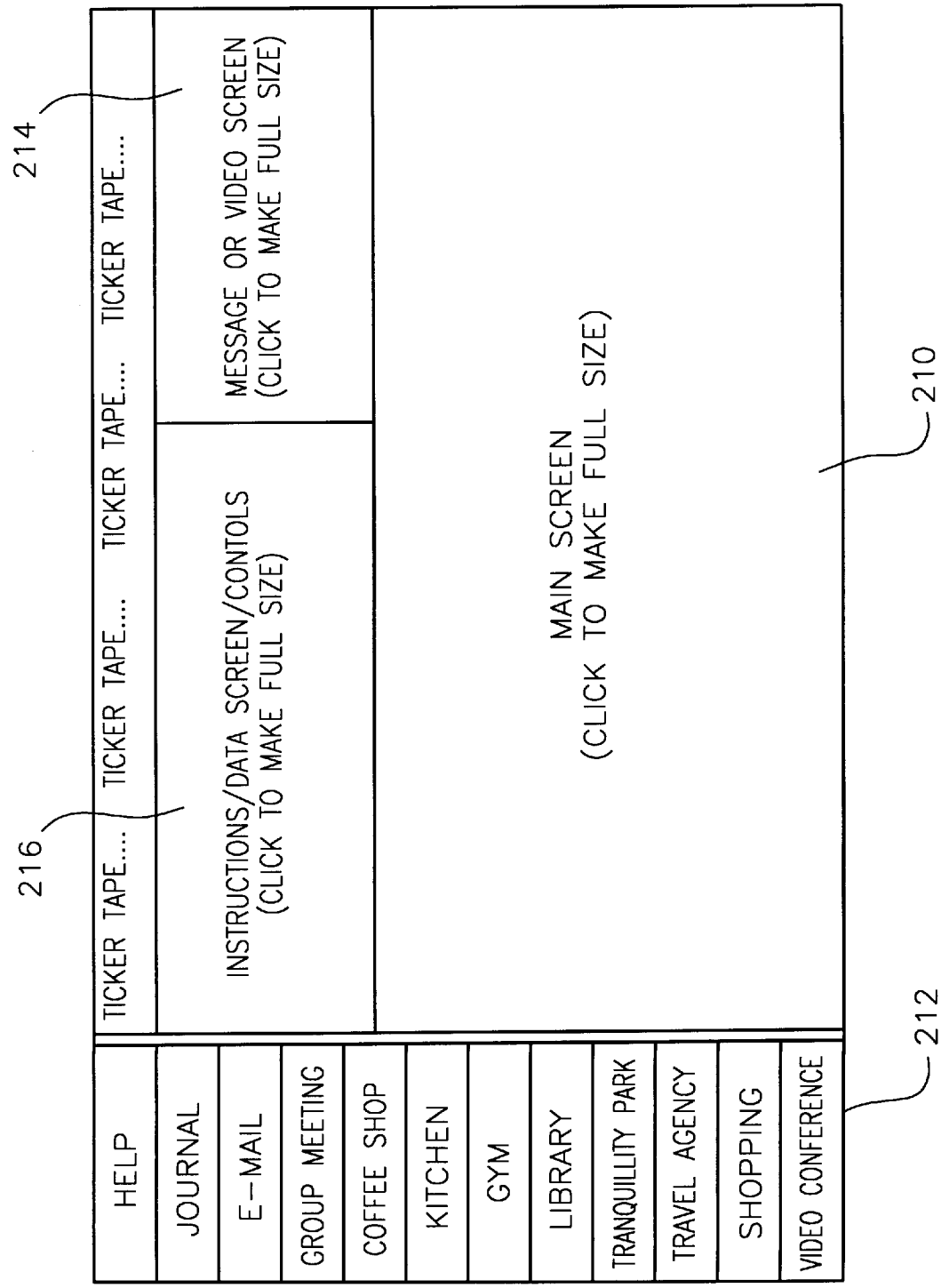
FIG. 37 is an alternative user interface screen provided by the system.

Another benefit of the village motif is its familiarity. A patient afraid of technology will be reassured through the symbolic images of home and neighbor, street and store. Finally, the patient may find navigating an electronic "neighborhood" more enjoyable than a traditional text-menu-driven system. Other user interfaces, such as the one described in conjunction with FIG. 37, are available.

Figure 9:
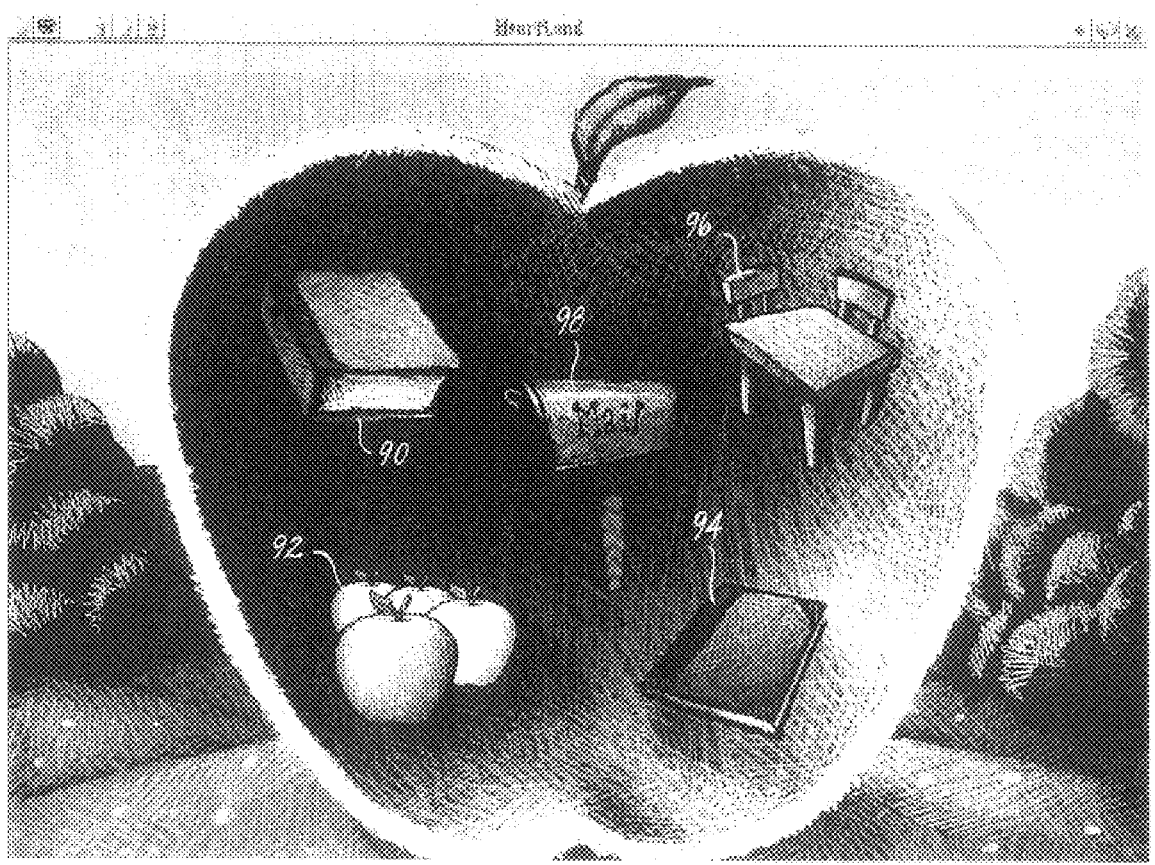
FIG. 9 is a graphical representation of the system's Inner Core option.

Referring to FIG. 9, the inner core 86 of the village provides the user with a schedule book icon 90, a journal icon 94, a meeting room icon 96, a mail icon 98, and a rewards icon 92. These give the user access to additional tools that assist with complying with his or her health program, and further help the physician or case advisor monitor such compliance.

Figure 10:
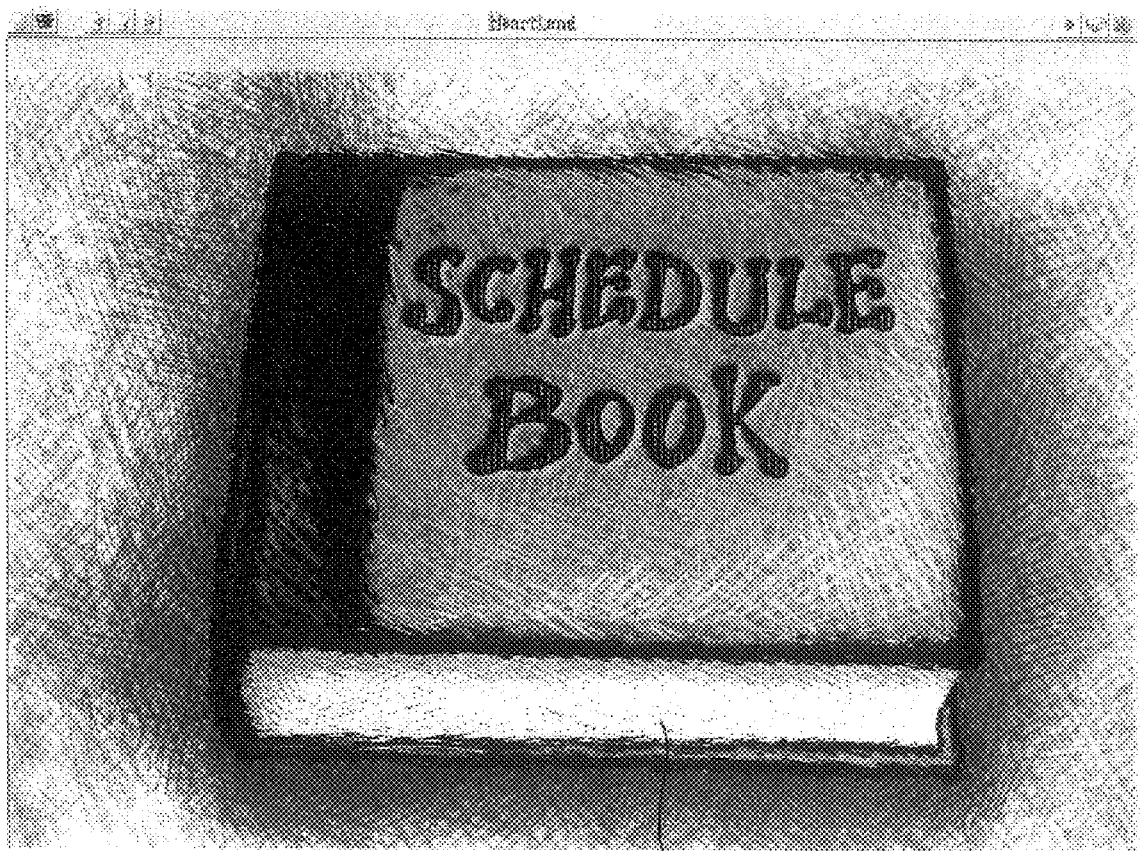
FIG. 10 is a graphical representation of the system's Schedule Book option.
Figure 11:
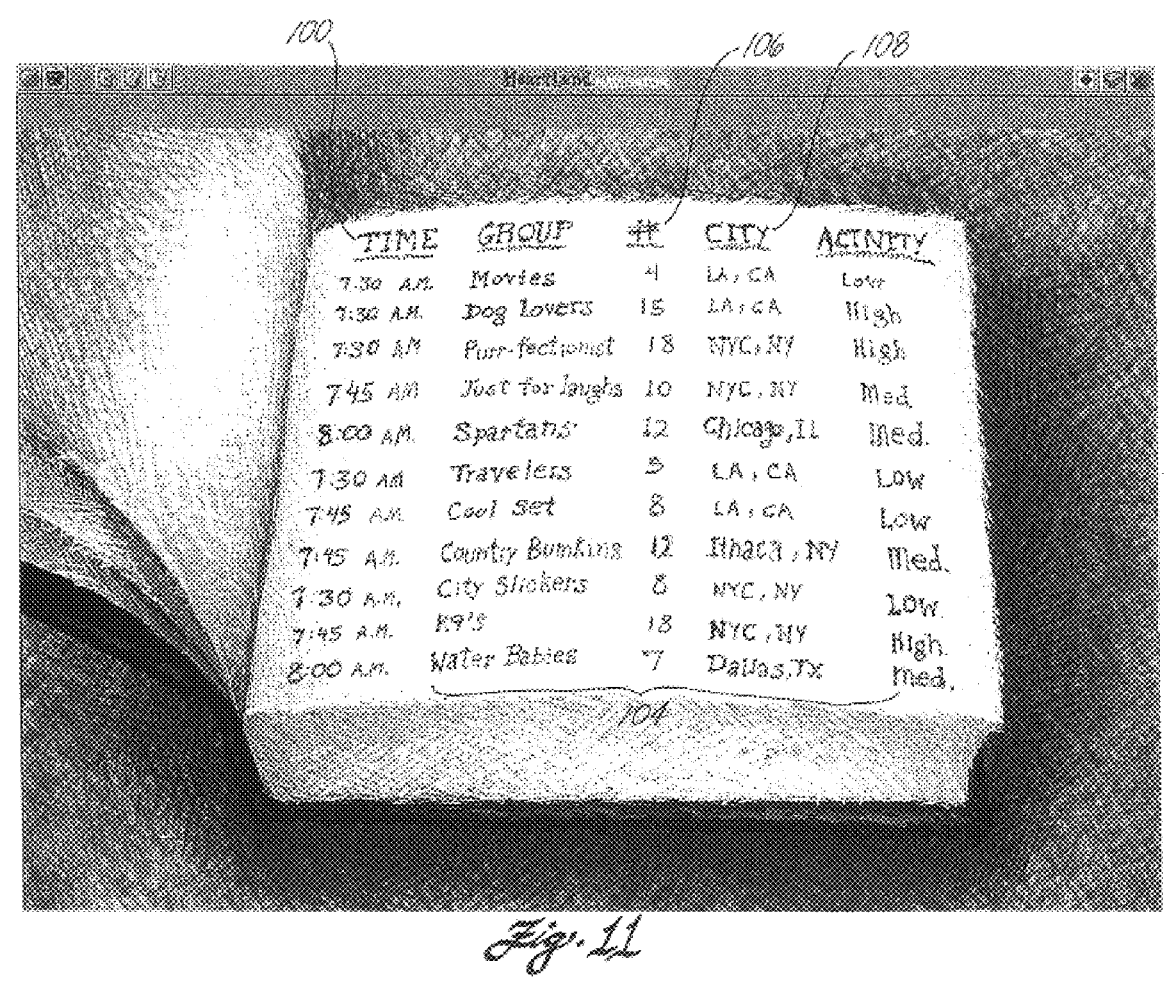

Referring to FIG. 10, upon selection the schedule book icon 90 from the interface of FIG. 9, the system displays a graphical representation of a schedule book 90A. As shown in FIG. 11, the schedule book presents the user with a list of meetings that the user can participate in via his or her computer. The list of meetings varies for each user depending on his or her specific health recovery program. The schedule book also presents general information on the meetings, including time 100, date (not shown), and meeting profile 104, with a notation of how may people have signed up for the meeting 106. The system also sets a limit on the maximum number of individuals that may sign up for a meeting.

Based on this information, a user may then sign up for the meeting that best fits his or her schedule. Other factors, such as the city in which the other members are located 108 may also influence the user's choice. A user may decide to join a group whose members are located in his or her home city if he or she wants to meet these people face-to-face someday.

The system integrates the user's schedule book 90A with the user's personal electronic daily calendar. For example, after a patient signs up for a meeting, the system downloads the day and time of the meeting to the user's calendar. The calendar may be any suitable commercial calendar or organizer program, such as Organizer™ available from Lotus Development Corp.

In an alternate embodiment, the user may make a further request via the schedule book for automated reminders to sent to him or her by e-mail.

Referring again to FIG. 9, the system also enables the user to access an integrated patient journal 94 from the village's inner core and self-report their progress and describe their feelings. Selection of a journal icon leads the user to a journal 94A like one shown in FIG. 12. Upon entering the journal 94A, the user has the option to view the personal goals that have been set for him or her by the physician or case administrator. The journal also provides a diary used to make a daily record of information pertinent to accomplishing the user's goals. The journal 94A provides an important tool that lets the patient express his or her feelings and fears in a context other than that of a support group. By journaling, the patient can identify fears concretely, and thus begin to address them. Goal setting is also often more meaningful when it is written down. Instead of merely thinking about ambiguous hopes, patients can define in written form the concrete milestones they plan to attain. These notes can also help remind the patient of matters he or she might wish to discuss in support group meetings. The system also uses certain notations in the journal to assist in generating reports to the physician or case advisor regarding the patient's progress. As part of its overall security measures, the system separates those journal entries which the patient wishes to keep private from those which are to be used in generating reports.

Figure 13:
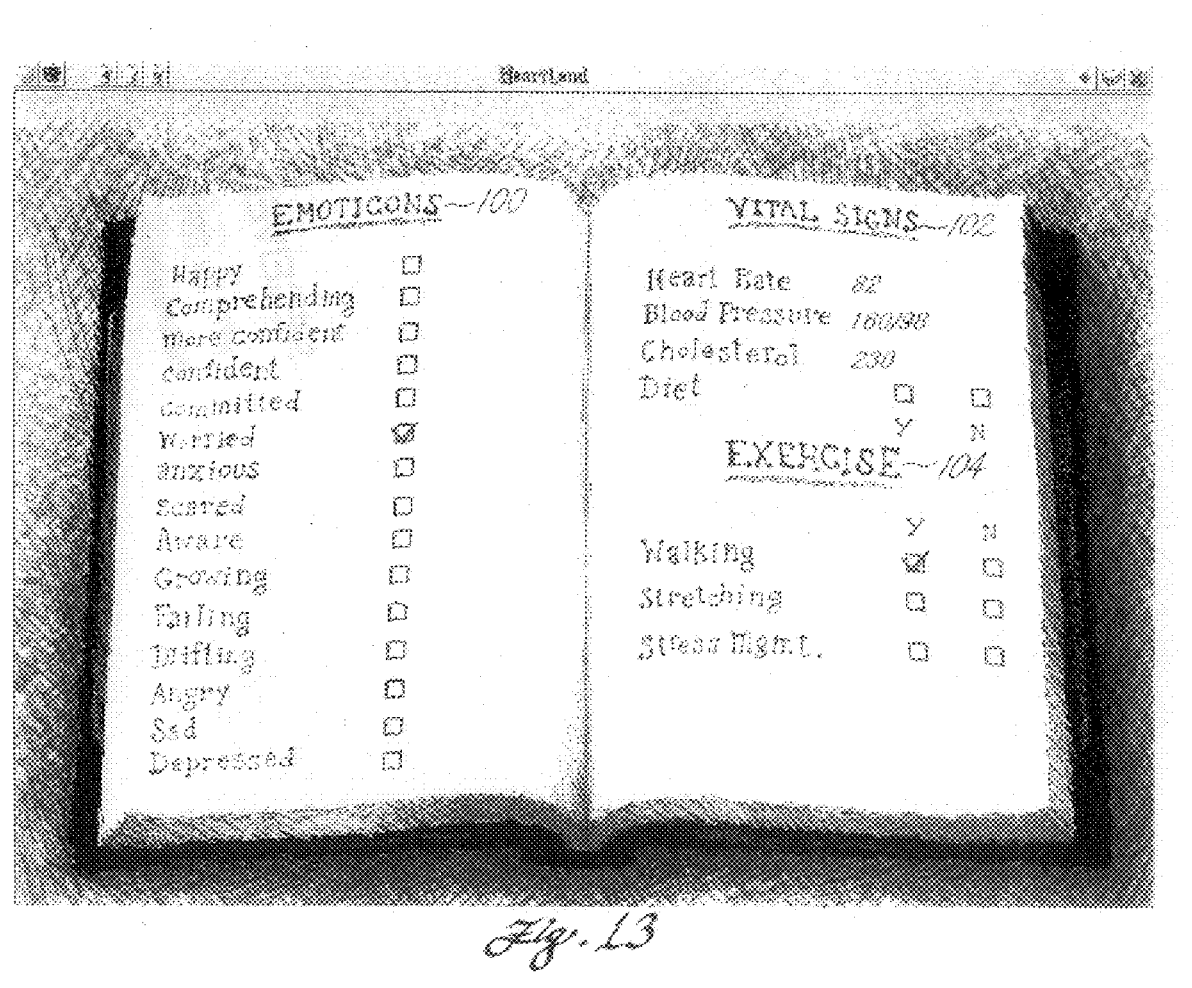

FIG. 13 exemplifies the type of information which may be contained in the journal. For instance, a heart patient belonging to a clinical group may need to monitor his or her emotions 100 as well as the exercises he or she has been doing 104 by means of the journal. Depending on the patient's program, the system might also prompt the patient to input his or her vital signs 102, such as blood pressure and heart rate, in the journal. This can be done manually or automatically. For example, devices can be hooked into the computer's serial port for automatic input of blood pressure and heart rate into the system. Depending on the particular program, patients might be required to weigh themselves on a weekly basis and/or measure their cholesterol level with a home cholesterol kit on a relatively less frequent basis. This information is stored in the system's database and is accessible to the physician and case advisor.

The kind of information required of a person in the wellness group may differ from this. For example, if a user is in the wellness group because a family member is suffering from a chronic illness, it will not be necessary for him or her to input vital signs into the journal. Rather, information as to how he or she is doing emotionally, as well as information as to how much group support he or she is getting, may be solicited.

The user may also record his or her personal comments in the journal. This information may only be viewed by the individual user, and is not available to the case advisor or physician.

The journal is also integrated with the user's daily calendar. The user may, for example, input information as to his or her exercise schedule (such as 30 minutes walking on Tuesdays, Thursdays, and Saturdays) or meditation schedule into the journal. The system then downloads this information into the user's daily calendar. Previous journal entries may also be viewed.

In addition to allowing the patient to electronically enter his or her updated health information, the journal also provides the physician or case advisor with a means of getting feedback on the patient's progress. The information recorded in the journal is electronically forwarded to the case advisor. Alternatively, the case advisor has direct access to portions of the journal stored in the system's database. The physician or case advisor can use the information provided in the journal to update the program on an on-going basis.

The system also accepts additional patient data obtained during office visits or directly from the patient via e-mail or other means of communication. The physician may also input additional data, such as that derived from laboratory tests, into the system. Accordingly, the system accepts updated patient data directly from the patient and through data entered by the physician during office visits (blocks 1030, 1032 and 1034, FIG. 60).

The system automatically correlates the patient's input with the physician's to check for accuracy. In addition, the system automatically provides the physician with reports of patient progress. Depending on the patient's plan requirements, the case advisor periodically reviews the patient-reported and physician-reported input to monitor whether the patient is complying with program parameters and meeting goals (block 1036, FIG. 60).

As part of the feedback process, the system provides an "alarm" option (block 1040, FIG. 60). The system compares actual data about the patient with the goals and parameters residing in the system's database and automatically notifies the physician or case advisor via e-mail or facsimile (or pager depending upon the severity of the problem), if a health risk is present (block 1042, FIG. 60). For instance, if a patient's current blood pressure is potentially dangerous, the system will automatically send an alarm to the physician or case advisor and require his or her immediate action.

If the difference between current data and goals does not present a threatening situation, the system will simply notify the physician or case advisor that these goals are not being met. For example, if the current data states that the patient has lost 5 pounds instead of 10, the system will notify the physician or case advisor of this fact. This information, although not life-threatening, must nonetheless be addressed by the physician or case advisor. He or she may then contact the patient in order to support and to further motivate him or her to meet the desired goals (block 1044, FIG. 60). In addition, the physician or case advisor may recommend that the program be modified to suit the patient's condition (block 1046, FIG. 60).

Regardless of whether an alarm condition exists, the system periodically correlates the updated patient health information with the program goals to determine the patient's progress and compliance with the program (block 1050). If the patient is progressing in accordance with his or her program, the system informs the physician and/or case advisor (block 1052, FIG. 60). The physician or case advisor may then provide positive reinforcement to the patient. Depending on the patient's progress, the case advisor or physician can also determine whether to modify the program by altering the goals or moving the patient into a different diagnostic category. The patient may even be removed from the system if he or she has met program end goals (blocks 1054, 1056, FIG. 60).

The system also notifies the physician or case advisor if the patient is not progressing toward program goals or is not using the system (block 1060, FIG. 60). The case advisor along with the physician then determines whether to modify the patient's therapeutic program, provide the patient with additional support, or remove the patient from the system (blocks 1064, 1066 and 1068, FIG. 60).

The system also enables direct feedback to the individual user. As one of the features of the journal, users may view their levels of compliance and achievement of goals. Patients may not recognize they are making progress until presented with reminders of how much they have improved. System generated charts and summaries, discussed below with respect to FIGS. 41 to 44, provide patients with an overview of how far they have come.

Referring again to FIG. 9, as another tool to assist patients to comply with their programs, the system offers an electronic meeting room and group support room interfaces via meeting room icon 96 through which a patient receives on-going, on-line group support. Putting a patient in contact with people with the same or similar problems through group counseling has clinically-proven therapeutic benefits. The system facilitates this process through the use of electronic and on-line technologies. On-line group counseling solves many of the logistical difficulties encountered in bringing together, on a regular basis, a large group of people with different schedules who live in different places. Instead of requiring patients to travel physically to a single location, the system enables them to attend group meetings by simply logging on to their computers. As the burden on the individual patient decreases, group attendance increases, and this enhances the overall practical, therapeutic value of group counseling and support.

On-line counseling also brings a patient into contact with a wider pool of people with similar problems than traditional counseling can. When desirable or necessary, group membership can be drawn from people in a wide variety of regions, instead of being limited to a single vicinity.

Furthermore, the relative anonymity of electronic communication benefits patients who are reserved or possibly embarrassed by their situations. These patients may be more willing to share their feelings in an on-line environment than they would be face-to-face.

Patients have access to the meeting room interface via a meeting room icon 96. Upon selection of the meeting room icon 96, patients are presented with meeting rules and regulations. They may then proceed to a pre-scheduled meeting. Only those scheduled for a meeting will be permitted to attend. The scheduling of meetings is part of the schedule book interface explained above in conjunction with FIGS. 10 and 11.

Figure 14:
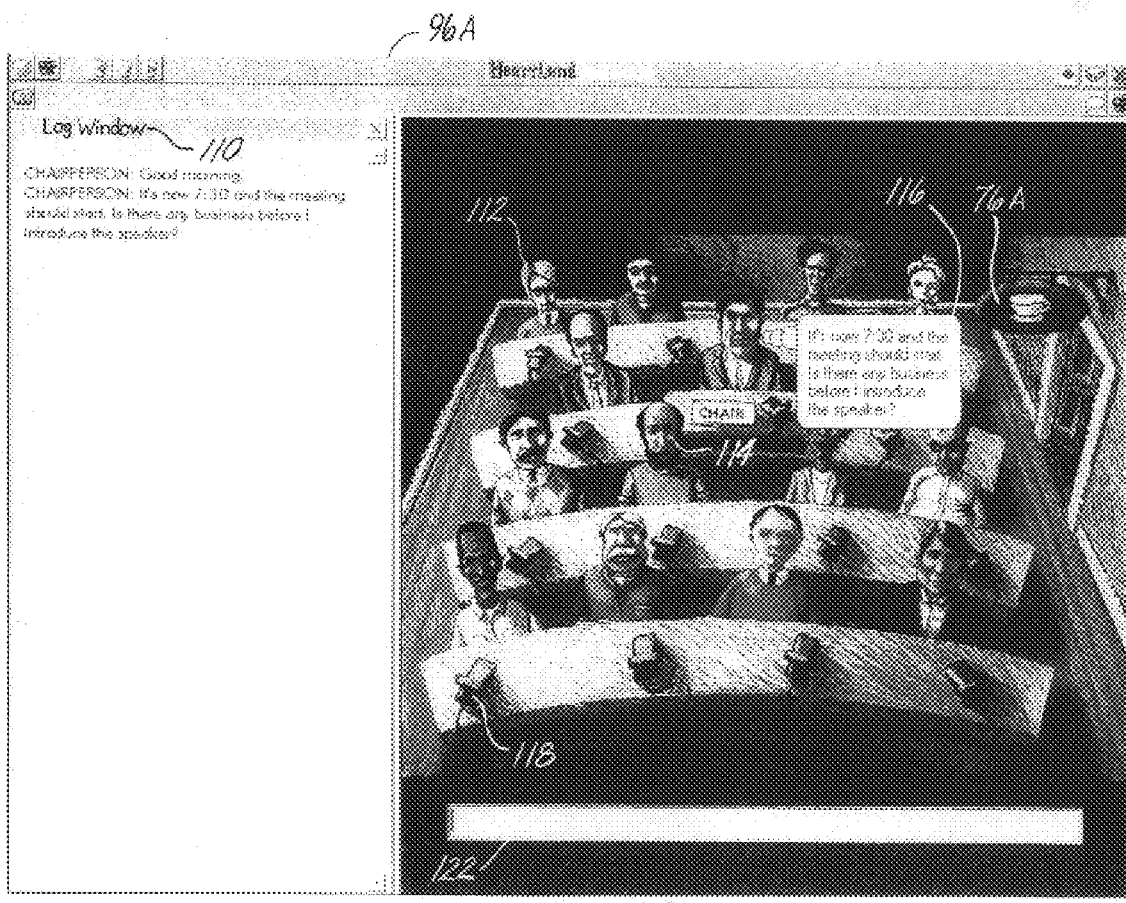
FIG. 14 is a graphical representation of the system's Meeting Room option.

Referring to FIG. 14, each participant 112 may chose to represent him or herself in one of two different ways in the meeting room. The participant 112 may have his or her photo scanned to represent him or her in the system. Alternatively, if anonymity is desired, the patient may choose to be represented by a non-photographic icon, or "avatar," accompanied by either his or her own name or a pseudonymous screen name. The patient will then be represented by that avatar in group meetings and private mentoring sessions. In some cases, patients may choose to design and construct their own avatars.

A trained, experienced leader or chairperson 114 is an important part of these group counseling sessions. It is the chairperson's responsibility to guide the discussion and encourage participation from all members. To enhance the beneficial aspects of group counseling, the system allows the chairperson 114 to access selectively certain parts of the patient's on-line journals and electronically display the selected portion in an anonymous manner to the on-line group. The chairperson can also cut somebody off electronically if he or she is saying things that are inappropriate.

In the preferred embodiment, a participant 112 "speaks" during the meeting by entering text at 122. Upon hitting the enter key, this text appears as "bubble-talk" 116 above the representation of the participant 112 who entered the corresponding text. In an alternate embodiment, instead of using a "bubble-talk" format, each participant 112 may participate at the meetings by talking into a microphone connected to his or her PC, and listening to other participants via speakers also connected to the PC.

A log window 110 keeps a running or scrolling record of the conversations during the meeting. Thus, if a participant 112 loses track of the conversation, or wants to comment on something said earlier, he or she has access to the entire conversation as reference.

During group counseling meetings, a chairperson 114 may play on-line multimedia presentations featuring other patients or well-known figures who have made positive lifestyle changes. In the presently preferred embodiment, each participant has access to the multimedia presentation, such as a video clip, via CD-ROM or DVD received by mail on a regularly updated basis. Alternatively, if the user has access to the appropriate software and hardware, and has a connection of sufficient bandwidth to the server, the multimedia presentation may be streamed to him or her over the network. In addition to CD-ROM, the system can also use DVD disk, downloads to the user's computer hard drive, or any other method or medium capable of storing or transmitting audio and video data.

When it is time to view the multimedia presentation, the chairperson selects, for instance, a particular video clip from a menu of video clips available on his or her CD-ROM or DVD. This sends a signal via the network to each participant's PC. The signal received matches a code on each participant's CD-ROM or DVD, which triggers the playing of the selected video by the PC. If the video is stored on DVD disk or on the user's computer hard drive, or some other storage medium, the video could be triggered to play from that medium as well.

The participants may not play the video prior to the meeting because only the chairperson has access to the code which releases the video. Thus, prior to a meeting, users may view a list of videos in his or her CD-ROM, DVD disk, hard drive, or other storage medium, but videos which have not been shown already at meetings will be inaccessible for viewing. Once a video is released by a chairperson and played for the first time at a meeting, the participants may access it any time thereafter.

The case administrator or advisor knows in advance who the chairperson for a meeting will be and will give him or her access to the video clip to be shown at that meeting.

The multimedia presentations shown at the meetings may feature well-known or public figures and other patients who may have dealt with the same issues that the participants are facing. For example, in a meeting for patients who have suffered heart attacks, a video clip of a celebrity who recovered from a similar problem may be shown. In the clip, the celebrity would talk about his or her own heart attack, the bypass surgery that he or she underwent, and the depression that followed. The celebrity would also describe other struggles that he or she faced, and how these struggles were overcome during the recovery process. Likewise, video clips of program participants may also be used to provide motivational examples of success stories, or to express deep-felt emotions (e.g., anger, depression, etc.) that must be dealt with by that individual and other members of the group in order to be successful in his or her recovery.

Such presentations may act as a source of motivation to the participants, giving them a sense of hope. If someone else was able to overcome the same obstacles, they can too.

The presentations may stimulate further discussion during the meeting, and allow participants to open up about the issues and struggles that they are facing during their recovery process.

Another function provided by the meeting room 96A interface is electronic telephone dialing. Each participant has a phone icon 118 in front of his or her avatar. If a participant wants to talk to any other person in the meeting, he or she may click on the phone icon and the telephone number to that person is dialed automatically. This allows the members to contact each other after meetings to talk further via regular phone lines if desired.

The conference room participants also have direct access to a more private mentoring area by clicking on a coffee shop icon 76B. Users of the system may also gain access to this private mentoring area by selecting the coffee shop 76 from the village as shown in FIG. 8.

Figure 15:
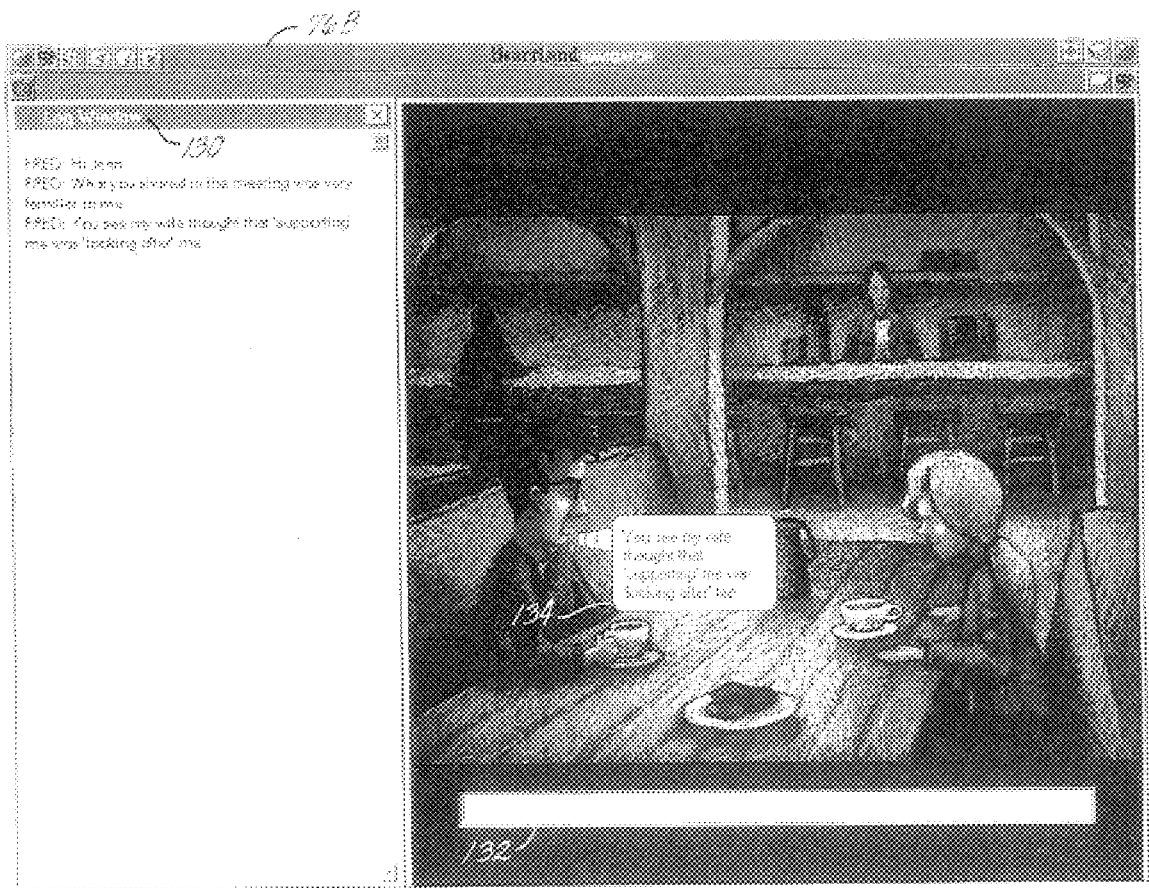
FIG. 15 is a graphical representation of the system's Coffee Shop option.

FIG. 15 is an exemplary illustration of the inside of the coffee shop 76B. Conversation here occurs much like in the meeting room 96A, except for the fact that the conversation is not monitored and structured by a chairperson. Text is inputted at 132 and appears as bubble talk at 134. A record of the conversation is also kept at the log window 130.

In the preferred embodiment, the system allows a maximum of four people into a single coffee shop at a time. Such a restriction is desirable given that the purpose of the coffee shop is for one-on-one mentoring. In the private setting of a coffee shop, more experienced individuals can pass on their experiences to less experienced ones as well as advice as to how to overcome the obstacles that they may be facing.

The group support room 96A and coffee shop 76B applications are implemented by means of third-party chat room applications such as Palace, commercially available from The Palace, Inc., Beaverton, Oreg. The chat room applications may be integrated into the system and modified to provide additional functionality. Triggering of multimedia presentations during group meetings and the monitoring of attendance are separately programmed into the system.

Through on-line group meetings and private mentoring rooms, the system allows patients to maintain contact with other people who have the same or similar problems, all in entertaining ways that encourage and assist the patient to adhere to program parameters and achieve program goals.

The communications feature of the system further allows users to keep in constant contact with their physician, case advisor, or other users of the system. Although in the presently preferred embodiment of the invention communication is done via e-mail, other methods of communication may also be used. For instance, it is envisioned that the system will allow instant messaging, conference calls, and/or video conferencing as alternate means of communication.

Referring again to FIG. 9, the mail icon 98 gives a user access to the e-mail feature. A user may also access his or her e-mail by selecting the village post office 74 shown in FIG. 8.

Figure 16:
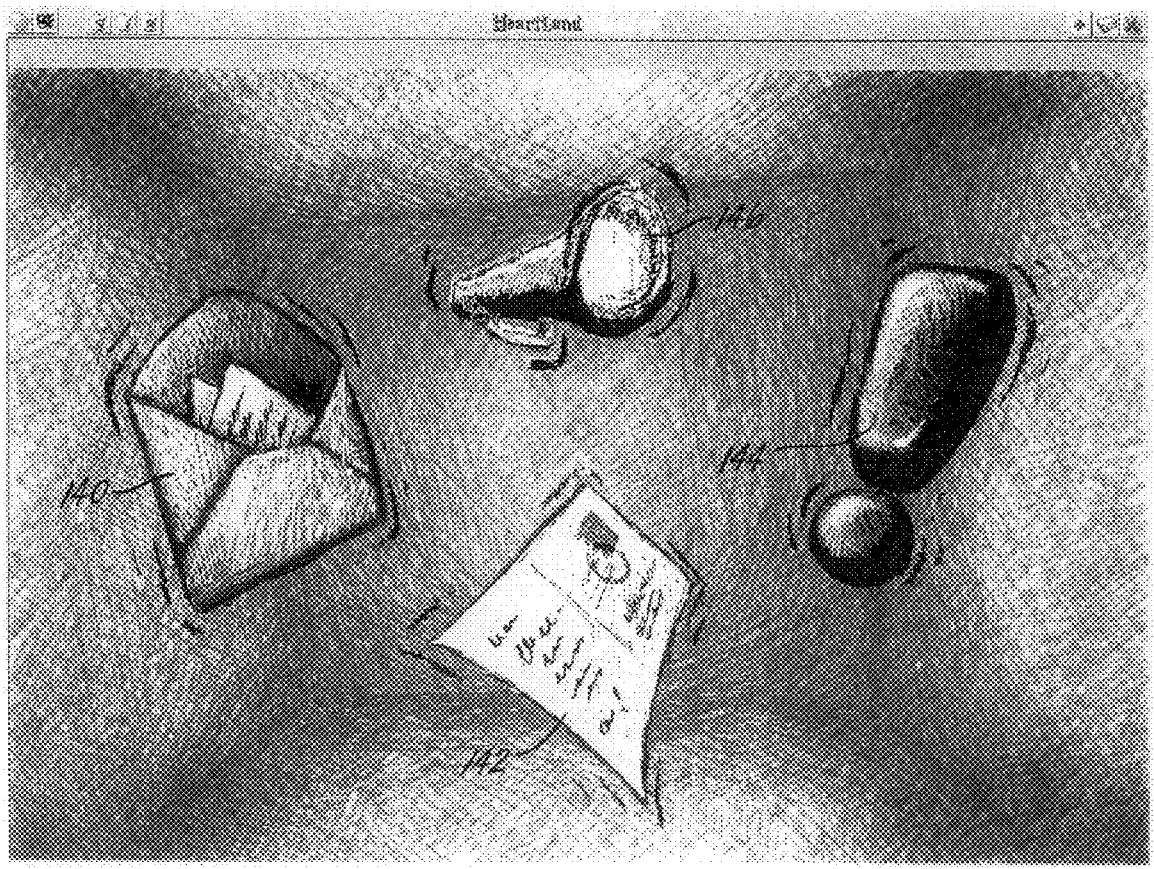
FIG. 16 is a graphical representation of the system's Post-office option.

Referring to FIG. 16, the system includes four different types of e-mail options: letters 140, postcards 142, telegrams 144, and audio e-mail 146.

Figure 17:
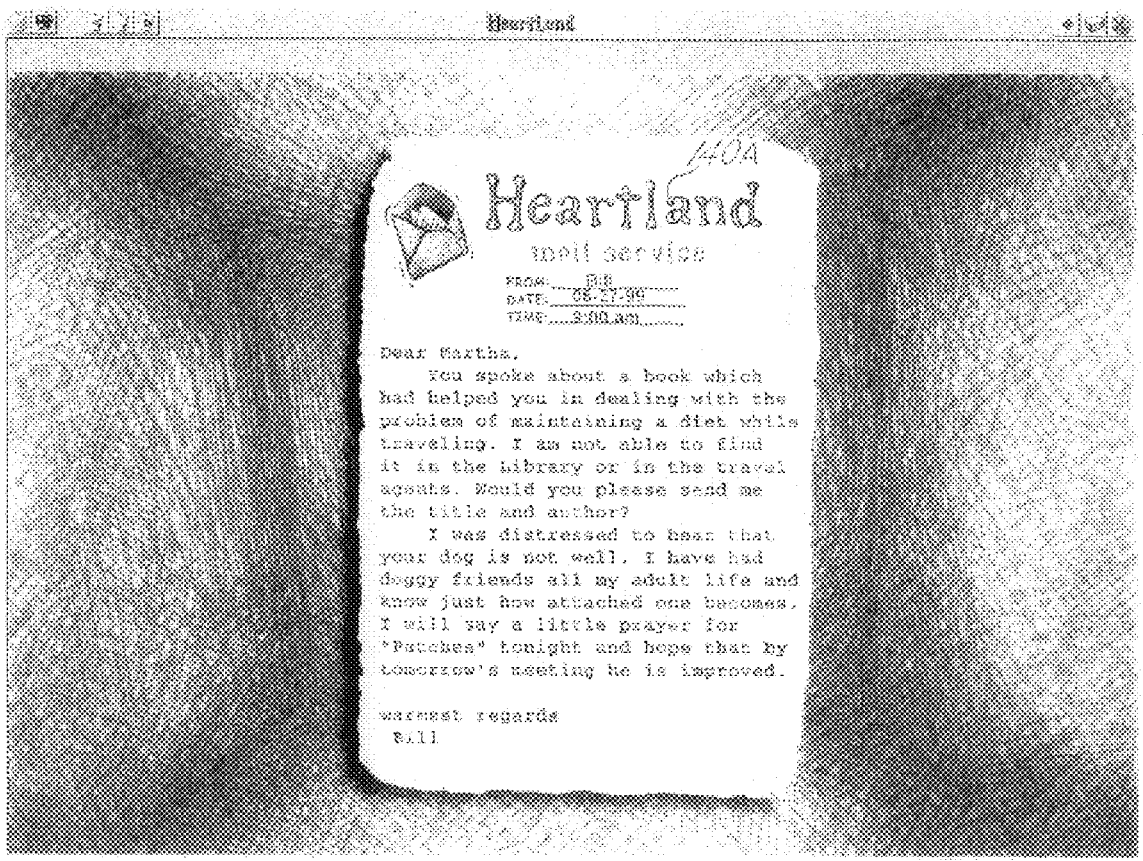
FIG. 17 is a graphical representation of the system's Note option.
Figure 1B:
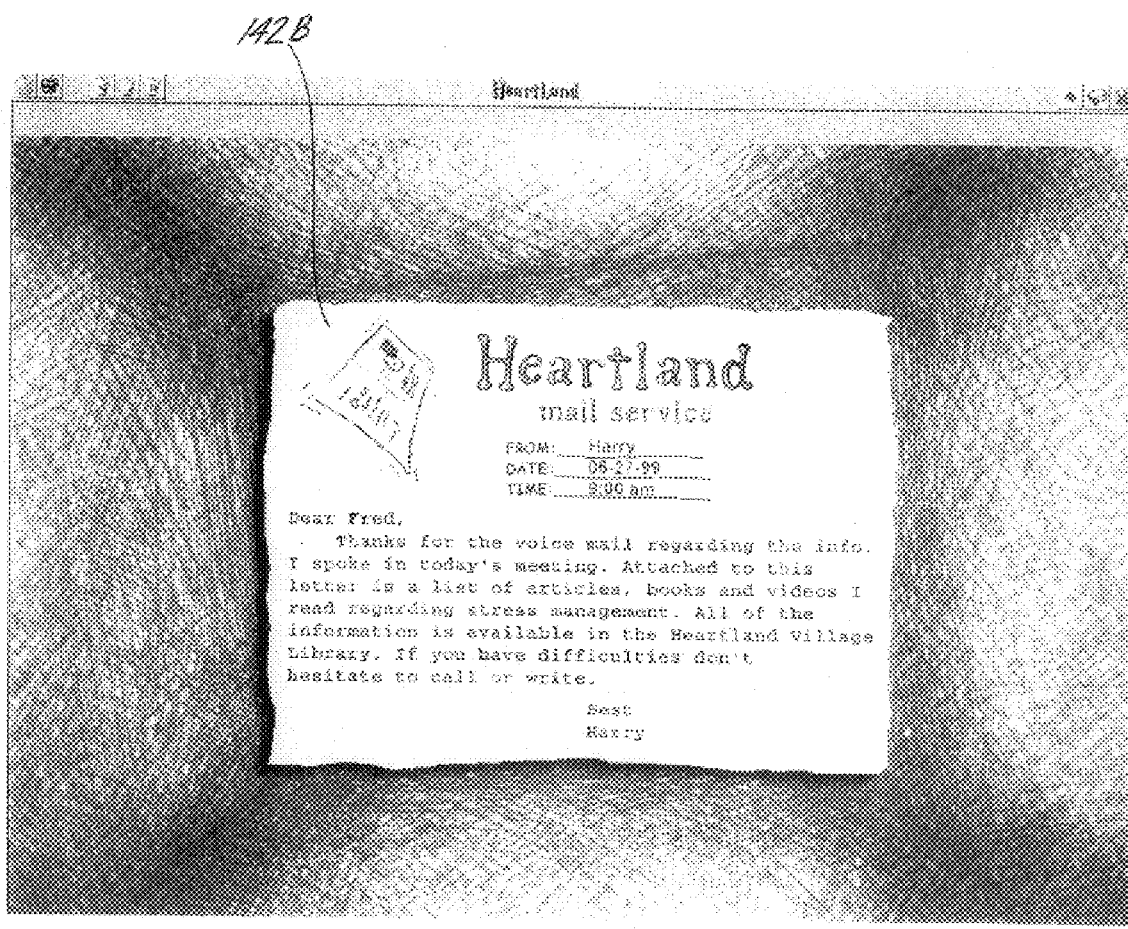

FIG. 17 is an example of a letter 140A, which functions as standard e-mail.

FIG. 18 is an example of a postcard 142B, which may be used to send short notes. For instance, postcards may be sent to users to survey the level of satisfaction with the service provided by the system. The postcard would contain questions on this issue, and users would be asked to send the postcard back after having answered the questions.

Figure 19:
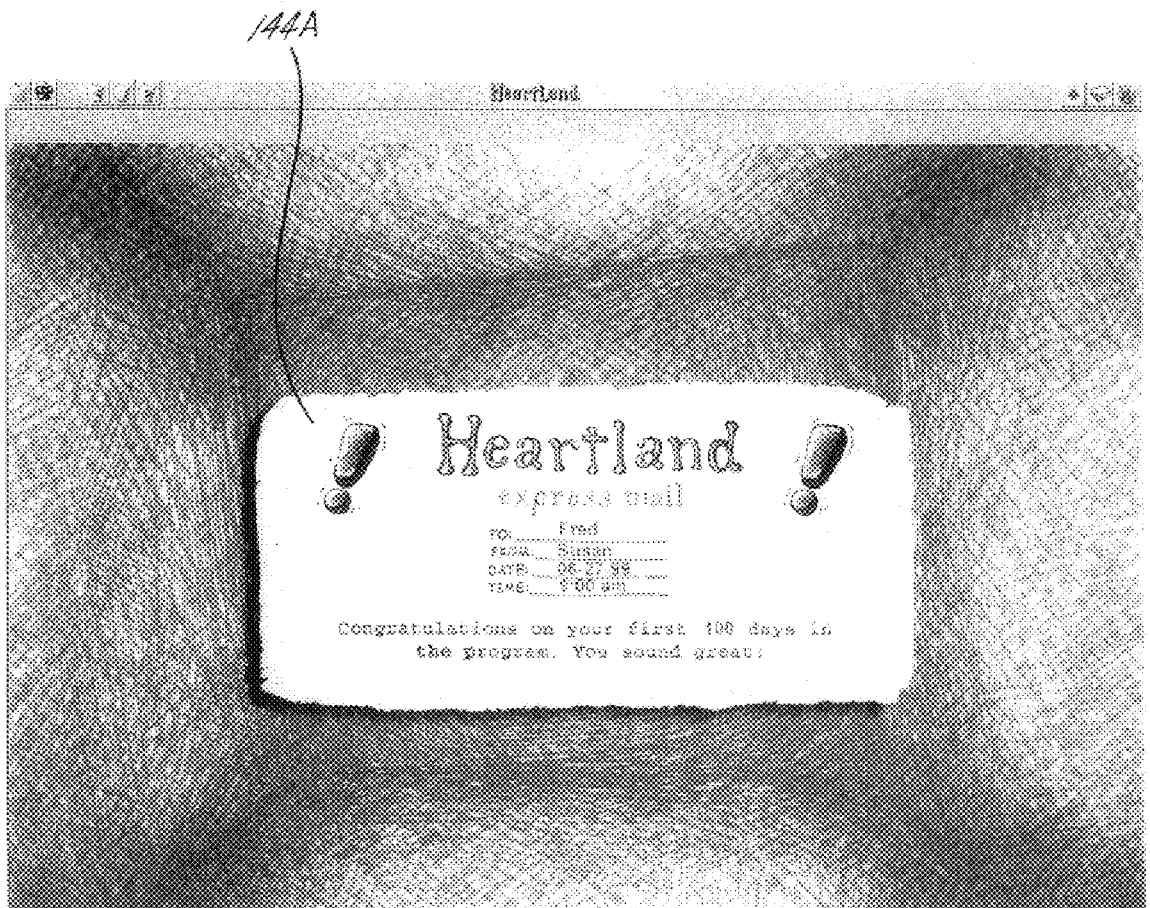
FIG. 19 is a graphical representation of the system's Telegram option.

FIG. 19 is an example of a telegram 144A, which has the highest priority among the types of e-mail provided by the system. The telegram may be used, for instance, to alert a user that he or she has missed a meeting, or just as a short note of encouragement by the case advisor or group leader to an individual user.

Figure 20:
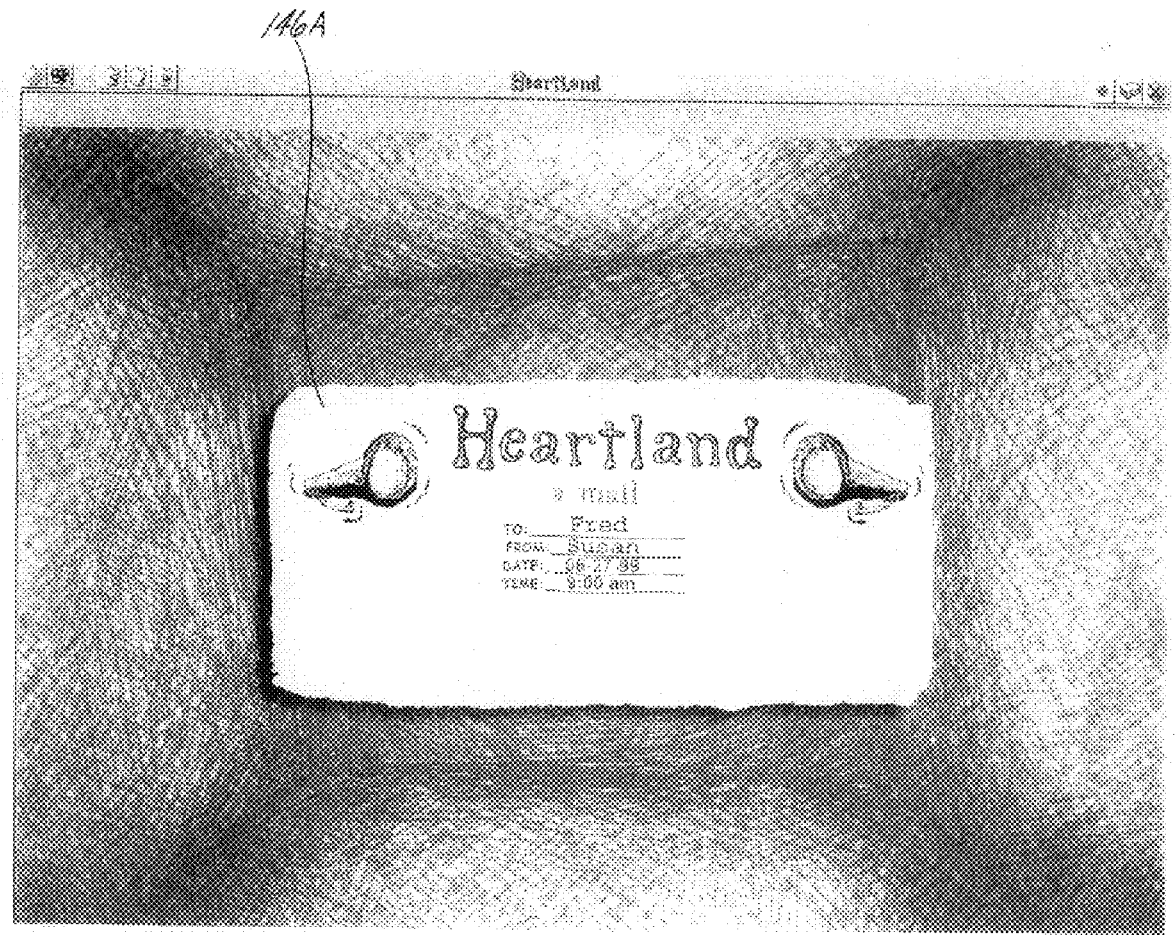
FIG. 20 is a graphical representation of the system's Audio E-mail option.

FIG. 20 is an example of an audio e-mail 146A notification. Upon clicking this icon, users can hear a recording of the message sent to them via speakers attached to their PCs.

The communications functionality may be implemented by integrating any one of a number of conventional e-mail programs with the system.

As will become more apparent from a detailed description of the system's other interfaces, the system takes a two-pronged approach to behavior modification: education and motivation. Entertainment is used as a means of both educating and motivating a user to make the sometimes difficult changes required for recovery or even for maintaining a healthy lifestyle.

Motivation is one approach to behavior modification. It is the path from education to compliance, which is a goal of the system as a whole. The support group and case advisor described above add a human element to this motivational component. Patients are more likely to respond positively to the encouraging words of others than they would be to a program which must be followed in isolation.

The system's multimedia capabilities allow it to use graphics, videos, and music to communicate and educate. These features provide a refreshing boost to the patient's endeavor to modify his or her behavior, replacing the drudgery typically associated with clinical medical rehabilitation programs. Segments featuring celebrities, medical experts, motivational speakers and successful program participants delivering motivational speeches and personal testimonials further inspire the user. Humor is integrated throughout the system, for example in the whimsical artwork. The entertainment derived from these features of the system is used to spark and maintain the patient's interest in the unfolding drama of his or her recovery and lifestyle change.

The rewards feature is yet another motivational tool provided by the system. Referring again to FIG. 9, the reward "apples" icon 92 allows a user to view information on the rewards point system and how it works, as well as the user's own personal rewards account. Users may earn points by good participation in the program and by reaching certain milestones. For instance, points may be earned for good attendance at meetings, good participation during the meetings, chairing a meeting, or losing a certain amount of weight, if this was a goal to be accomplished.

Rewards range from the symbolic kind, such as getting "gold stars" that commend a user for his or her progress, to reward points and frequent flier miles which may be exchanged for goods in the village store 78 or plane tickets in the village travel agency 82, respectively.

Education is a complementary behavior modification approach offered by the system. Education is provided through informative on-line multimedia presentations and the interactive areas of the village devoted to diet, exercise, and stress management. For example, the recipes provided in the village kitchen, discussed below in conjunction with FIGS. 21–24, are designed to improve patients' diets without forcing them to take on impossible austerities or give up their love for food.

Exercise and stress management programs, discussed below in conjunction with FIGS. 26–31, are designed both to allow for variety and to lie within the individual patient's ability range. By making exercise and a healthy diet both feasible and interesting, the system enables patients to stick with their new lifestyles.

The system also provides relevant articles and includes hyperlinks to other, reputable Internet sites devoted to providing medical and health-related information, as discussed below in conjunction with FIGS. 32–35.

Figure 21:
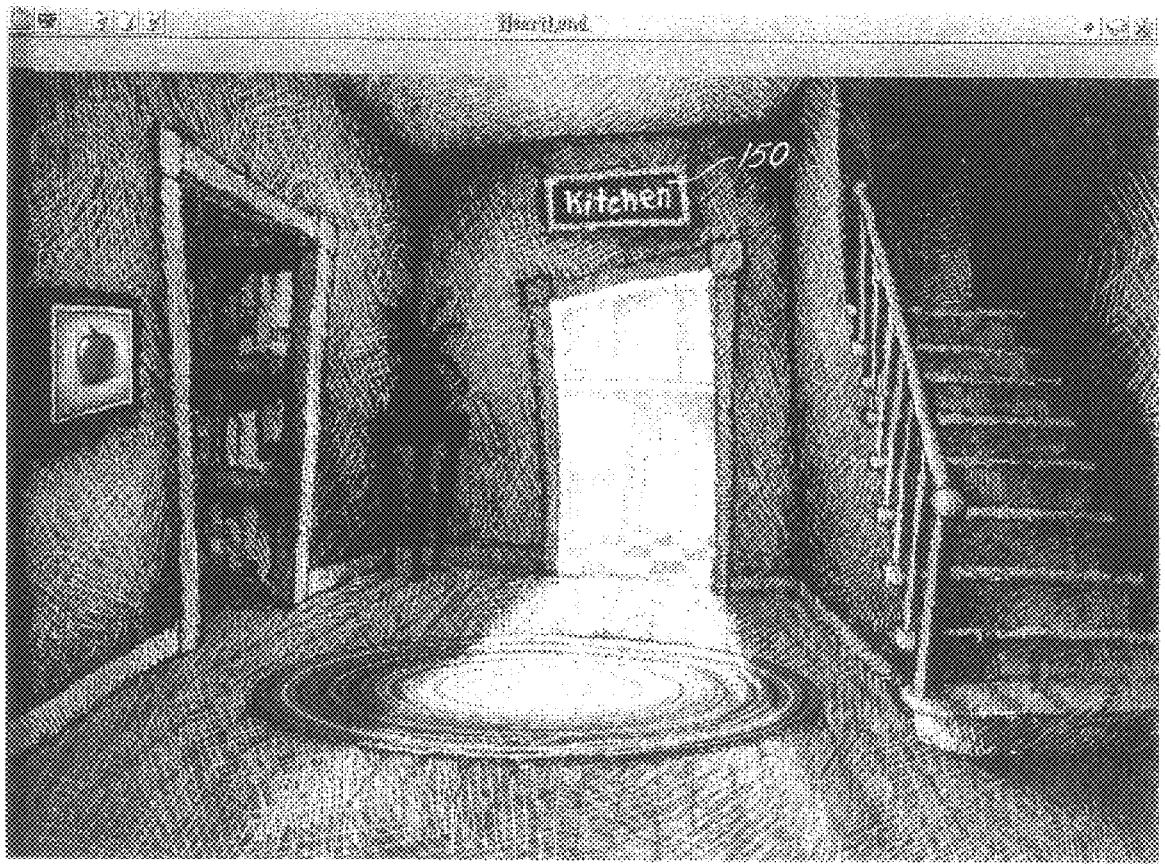
FIG. 21 is a graphical representation of the system's Kitchen option.

Referring again to FIG. 8, the system encompasses a "home" 84 interface as part of the village motif. Upon its selection, a screen showing the inside of the user's "home" 84 follows, as depicted in FIG. 21. Once inside his "home" 84, the user may access the kitchen by selecting the kitchen icon 150.

Figure 22:
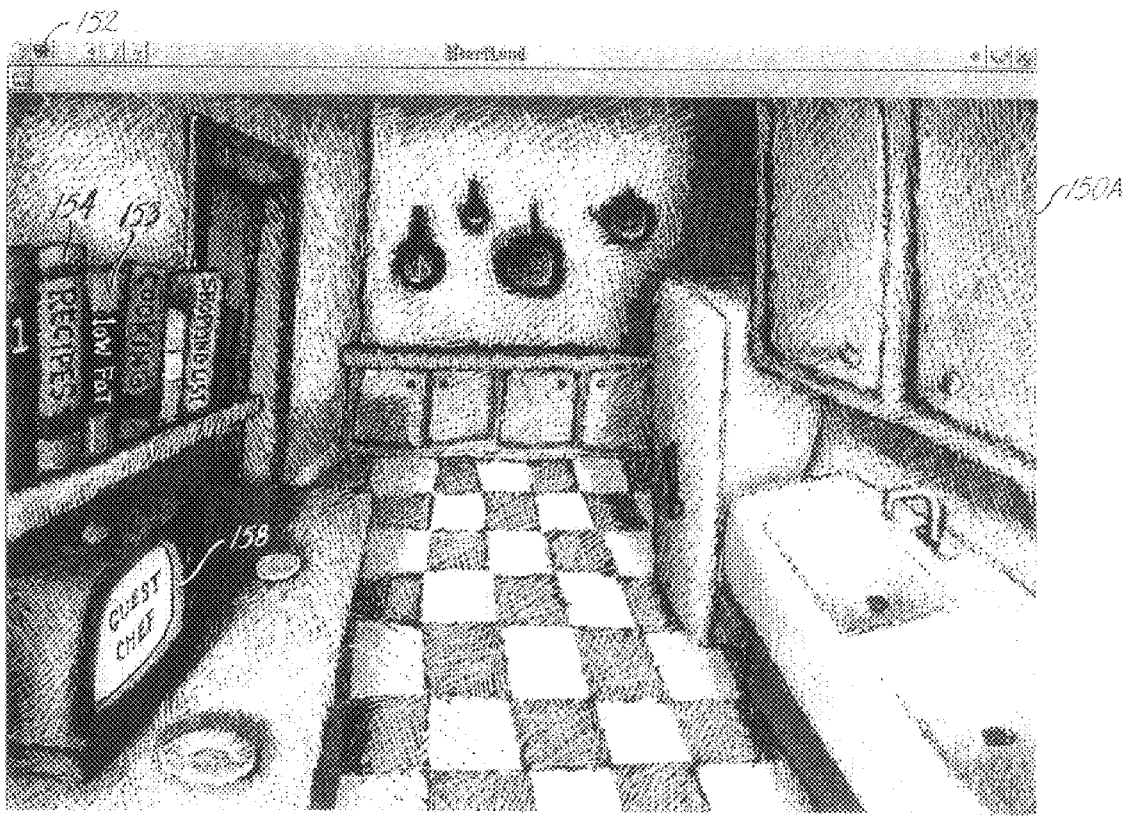
FIG. 22 is an expanded graphical representation of the Kitchen option.
Figure 23:
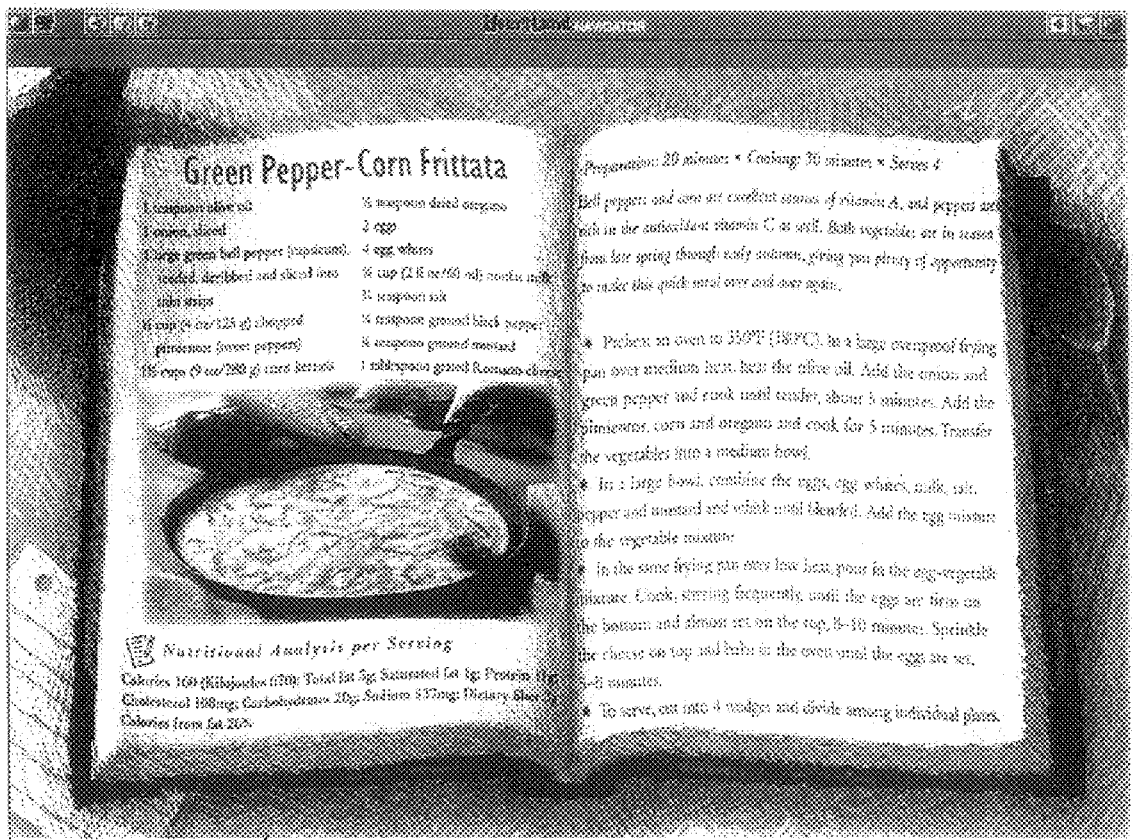
FIG. 23 is a graphical representation of the system's Recipes option.

FIG. 22 illustrates the interior of the user's kitchen 155. Once in the kitchen 150A, users have the option to get nutritional and dieting information from low-fat cookbooks 153, or view and print recipes from a recipe book 154. FIG. 23 gives an example of a recipe which may be contained in the recipe book 154.

Figure 24:
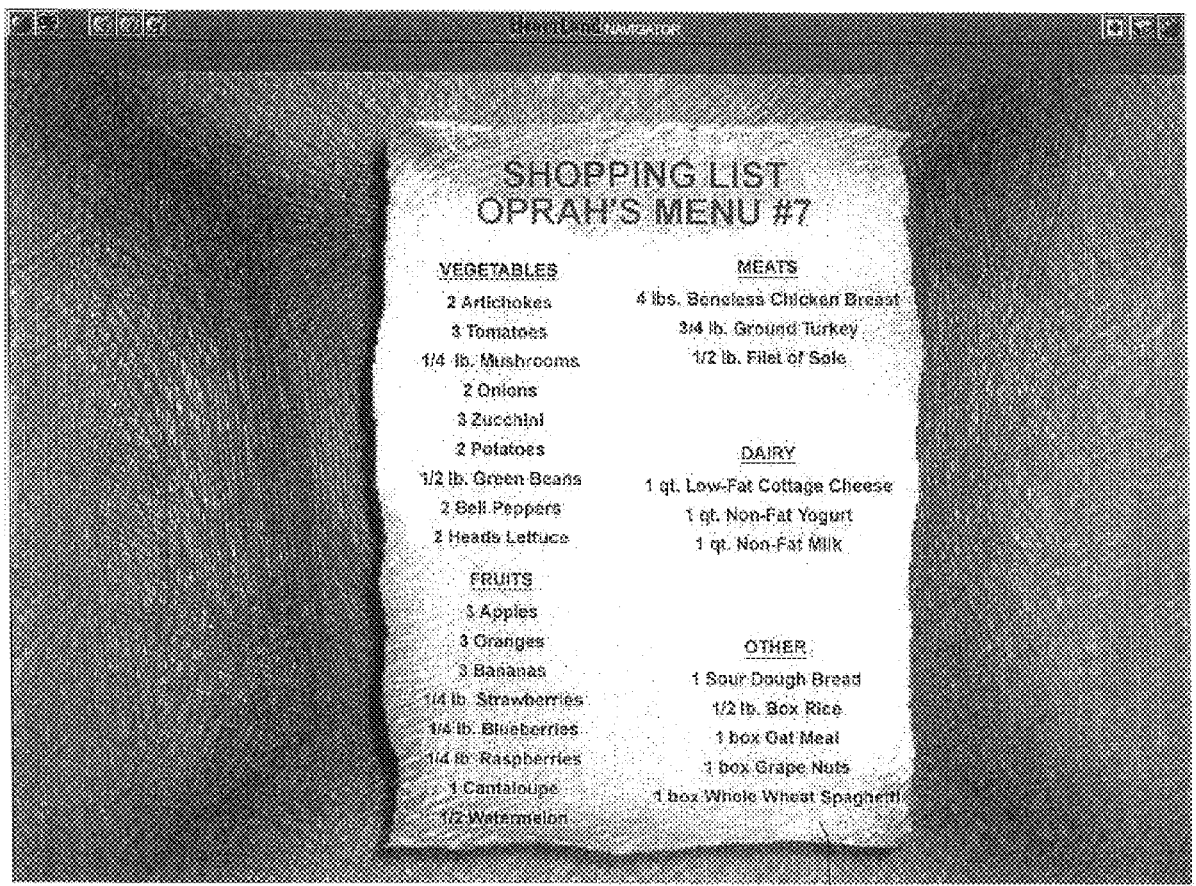
FIG. 24 is an expanded graphical representation of a Shopping List option.

Referring again to FIG. 22, users also have the option to prepare and print a shopping list 156. A user may chose several recipes from the recipe book 154, and the system can automatically enter the ingredients into the user's shopping list 156. The user can also manually enter items into the shopping list 156 via his or her PC keyboard. FIG. 24 gives an example of a user's shopping list.

The system can also indicate which recipes are allowable under the particular patient's program. For example, the system might recommend certain low-fat items that meet the criteria of a patient's program as well as suitable foods he or she might consider when eating out. The system is also capable of generating weekly shopping lists based on program parameters. According to personal preference, users may choose to substitute certain allowable foods for other.

Figure 25:
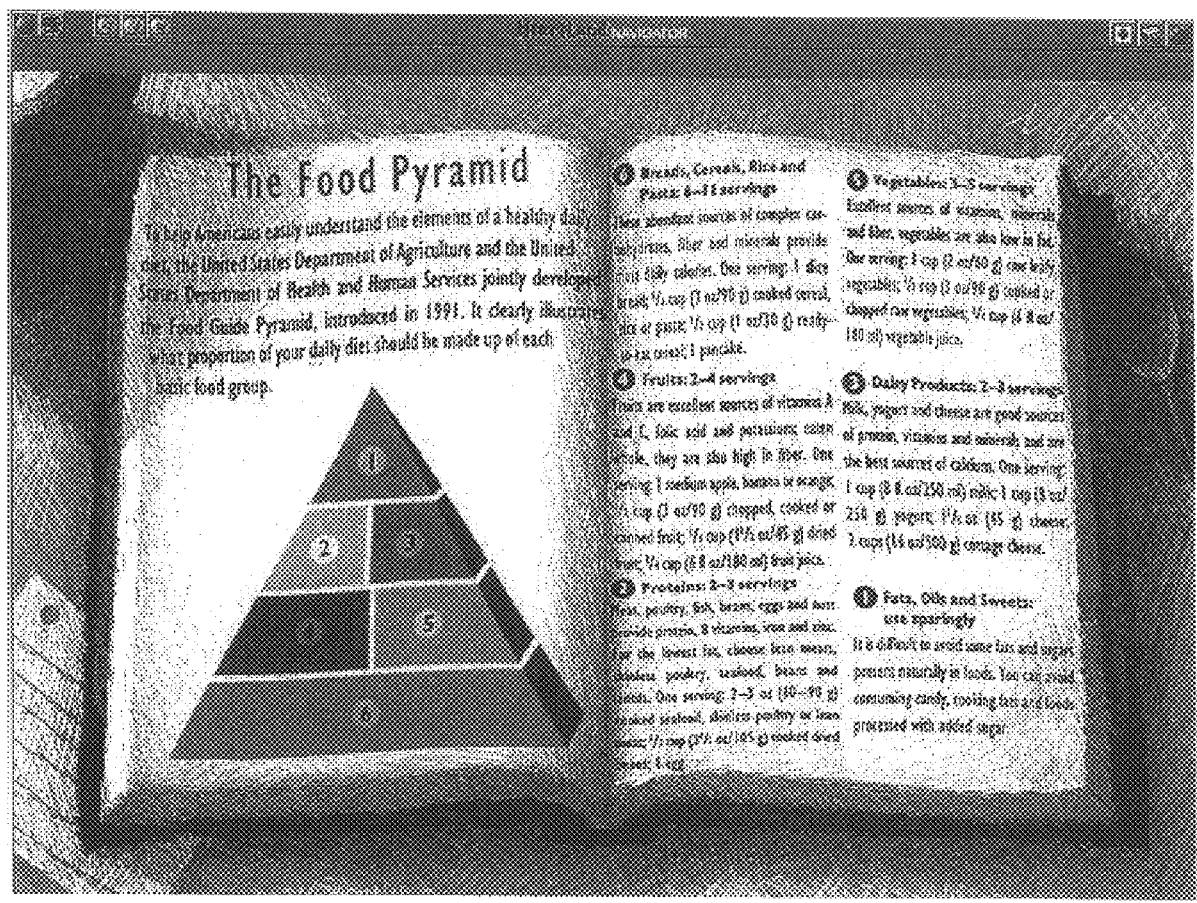
FIG. 25 is an expanded graphical representation of an educational topic available through a pull-down menu in FIG. 22.

Moreover, users have access to a pull-down computer menu by selecting the computer menu icon 152. From this computer menu, users can access various educational topics related to food, nutrition, and diet. One such topic may, for instance, relate to the basic food groups and may provide information as to the suggested amount of servings for each category of food, as shown in FIG. 25.

The guest chef 158 option shown in FIG. 21 further allows users to view audio or video clips of a chef showing how to prepare a certain recipe. In the presently preferred embodiment, these clips are contained in the user's CD-ROM or DVD, but with proper technology could be sent via streaming audio or video.

From the kitchen, a user may substitute foods (e.g., asparagus for broccoli); access and print food related articles; view new recipes or articles by selecting the "what's new" button (not shown); or join a discussion group via a bulletin board (not shown).

Figure 12:
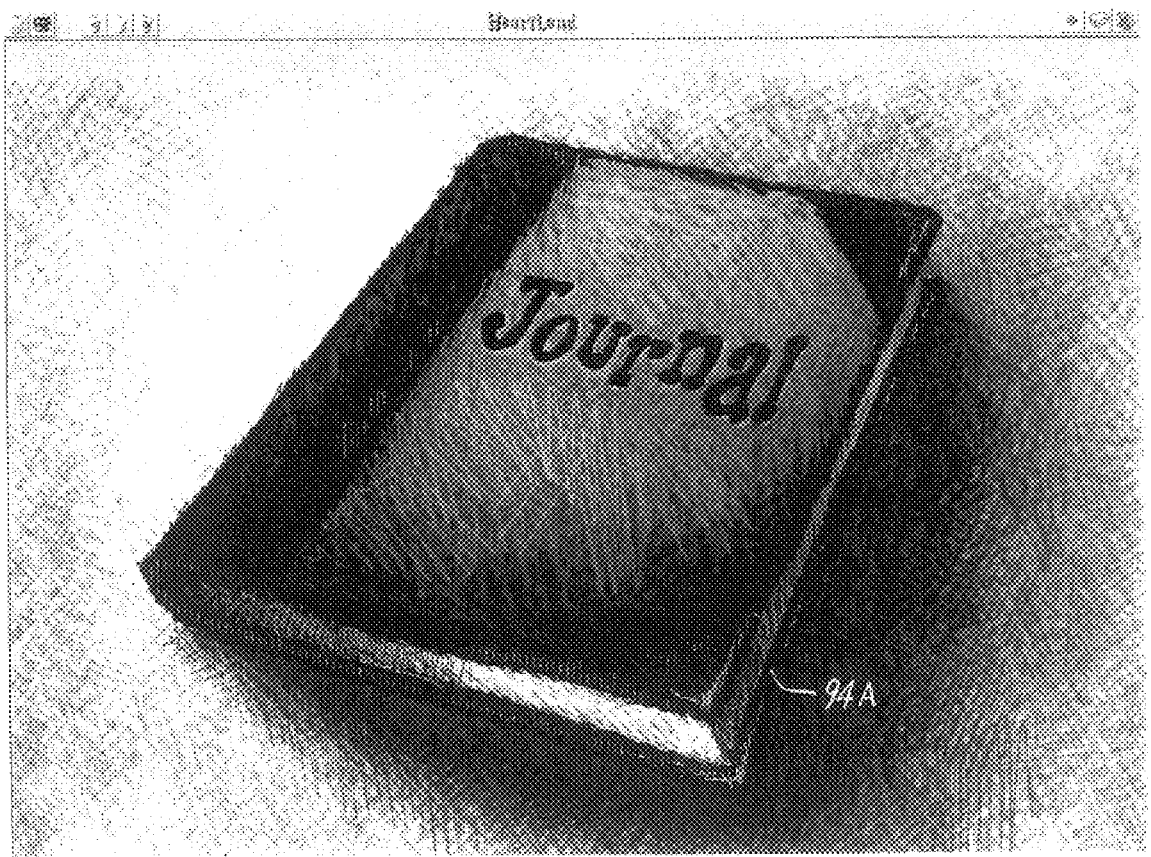
FIG. 12 is a graphical representation of the system's Journal option.

Referring again to FIG. 8, another part of the village motif is the village gymnasium 71, which is used by the system to make recommendations or supply information regarding suitable exercise routines. Each exercise program is generated according to individualized parameters and needs, with progress being regularly charted by user input via the journal 94A (FIGS. 12–13).

Upon entering the gymnasium 71, a user may view featured video clips or listen to audio clips; do key-word searches to access and print exercise related articles; read and print exercise manuals; or join a discussion group via a bulletin board.

Figure 26:
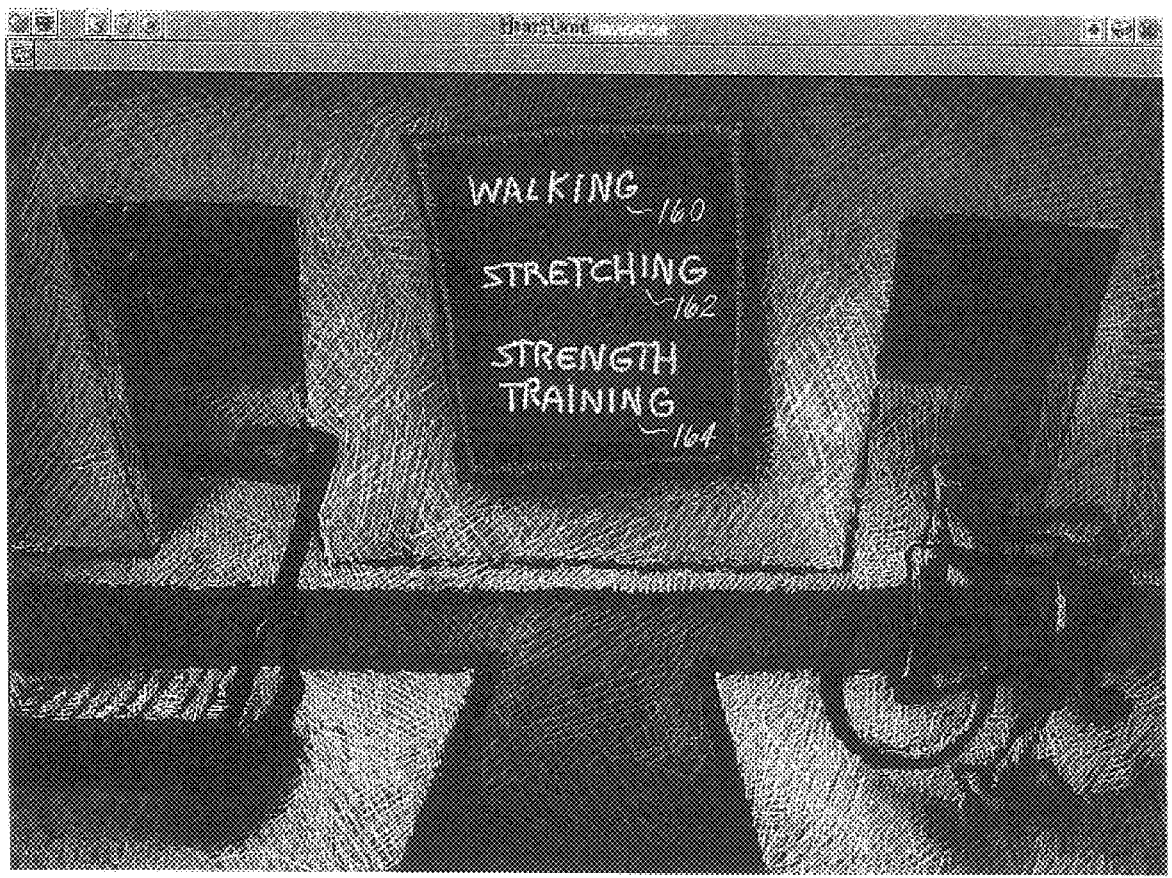
FIG. 26 is a graphical representation of the system's Gym option.
Figure 27:
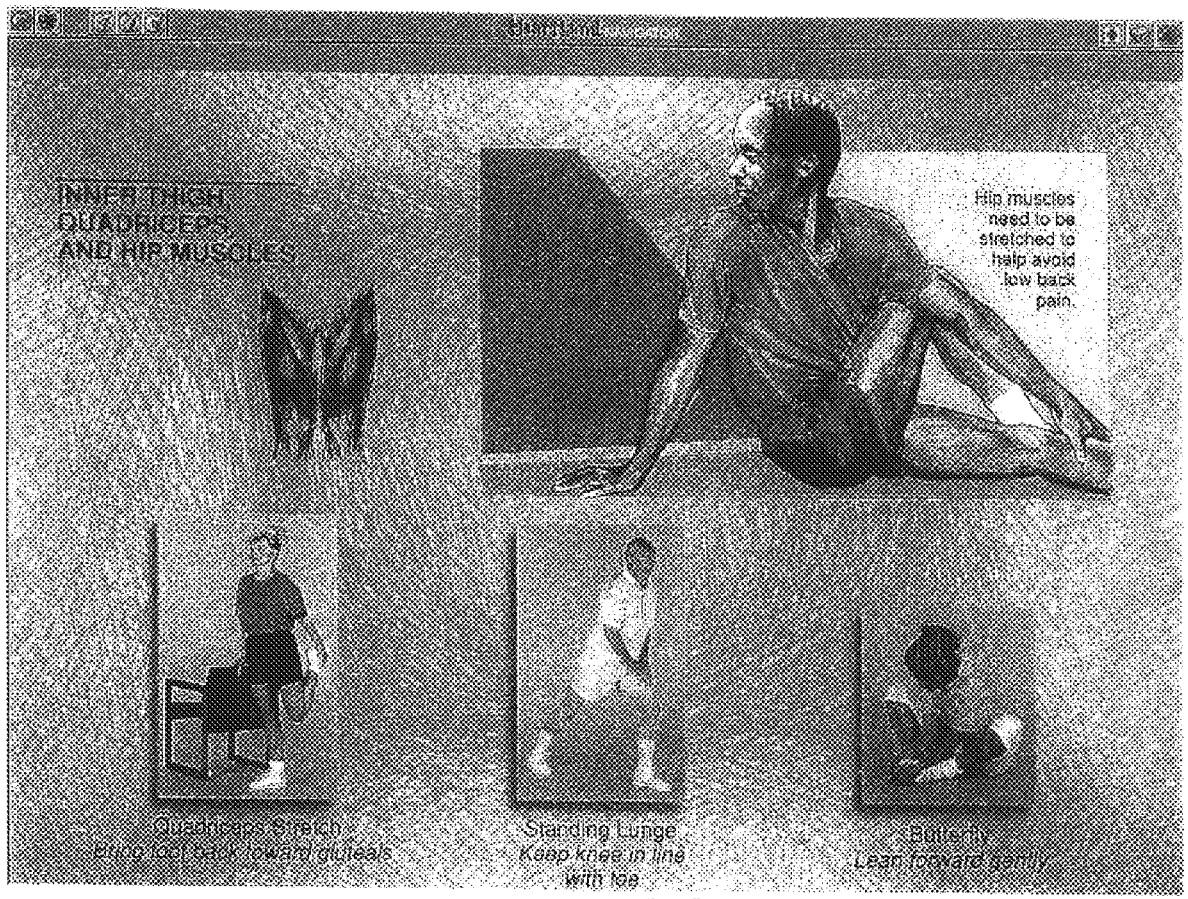
FIG. 27 is a graphical representation of a Stretching option of FIG. 26.

FIG. 26 illustrates the inside of a gymnasium 71 shown in FIG. 9. Shown here are various exercise topics 160 that a user may access. For instance, selecting the stretching topic 162 gives the user information on recommended exercises for stretching different muscle groups. FIG. 27 illustrates one such stretching exercise.

Figure 28:
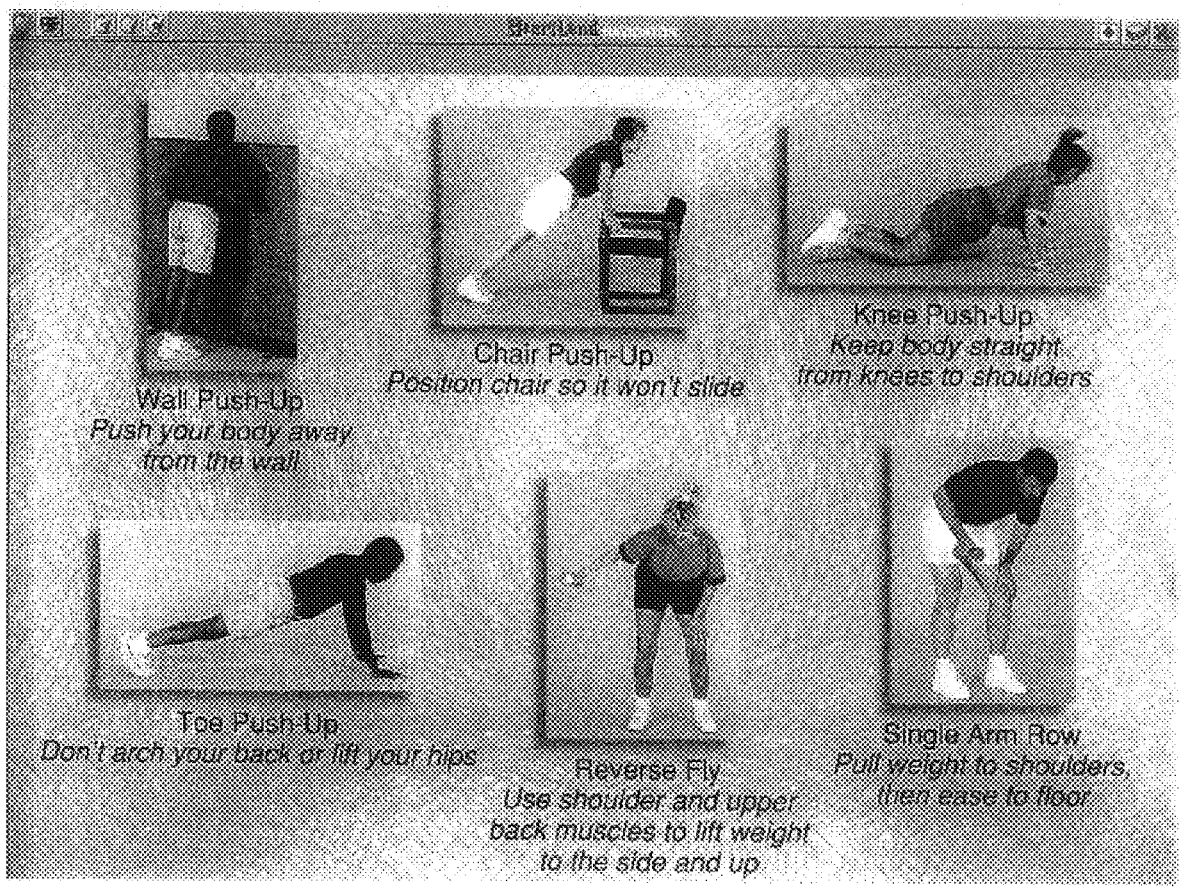
FIG. 28 is a graphical representation of a Strength Training option of FIG. 27.

Similarly, selecting the strength training topic 164 gives the user information on recommended exercises to help strengthen various muscle groups. FIG. 28 illustrates one such strength training exercise.

Referring again to FIG. 9, the village tranquility park 72 focuses on stress management strategies, including relaxation techniques, biofeedback, yoga, and meditation. Upon entering the park 72, a user may access and print articles on stress management subjects; view video clips or listen to audio clips on these subjects; and join discussion groups via a bulletin board.

Figure 29:
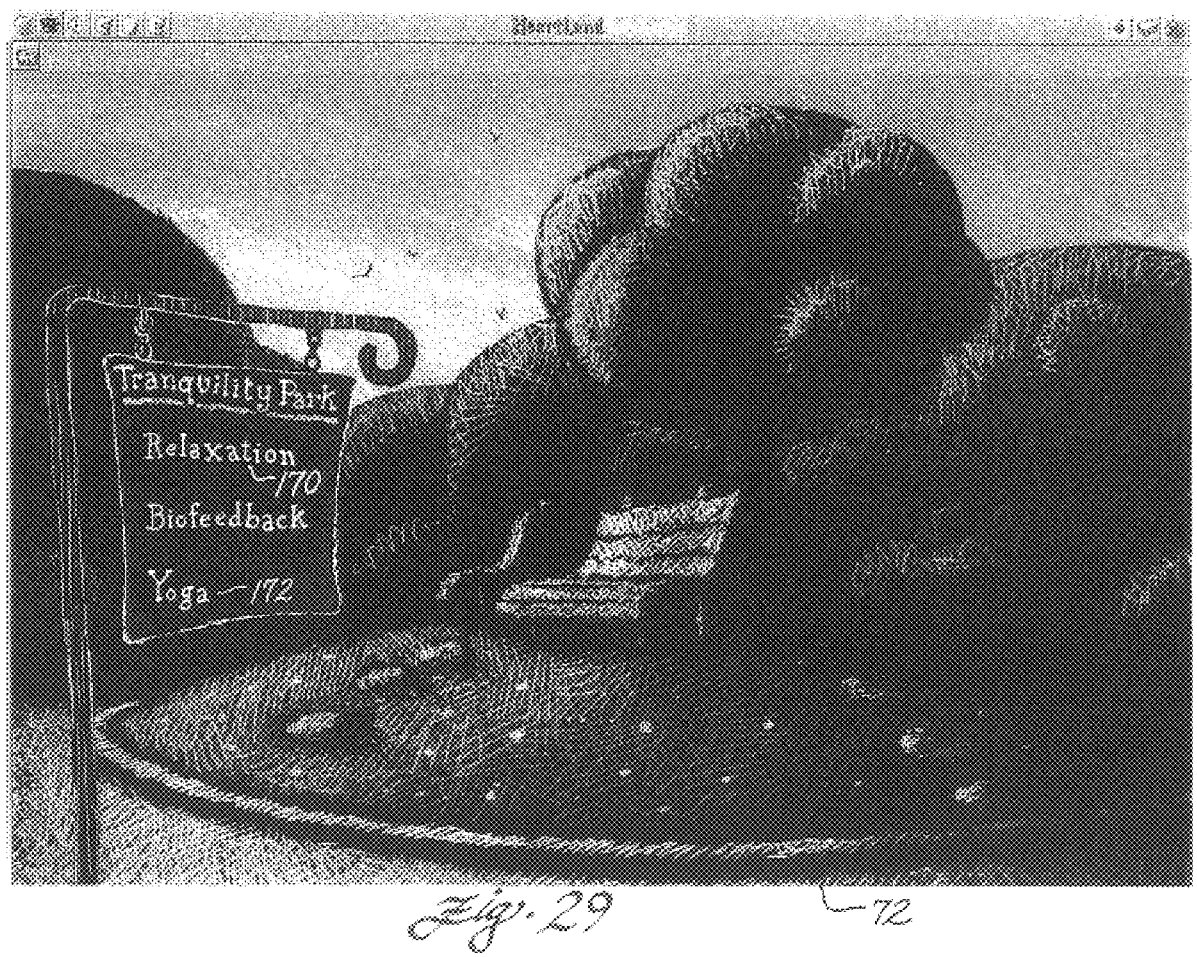
FIG. 29 is a graphical representation of the system's Tranquility Park option.
Figure 31:
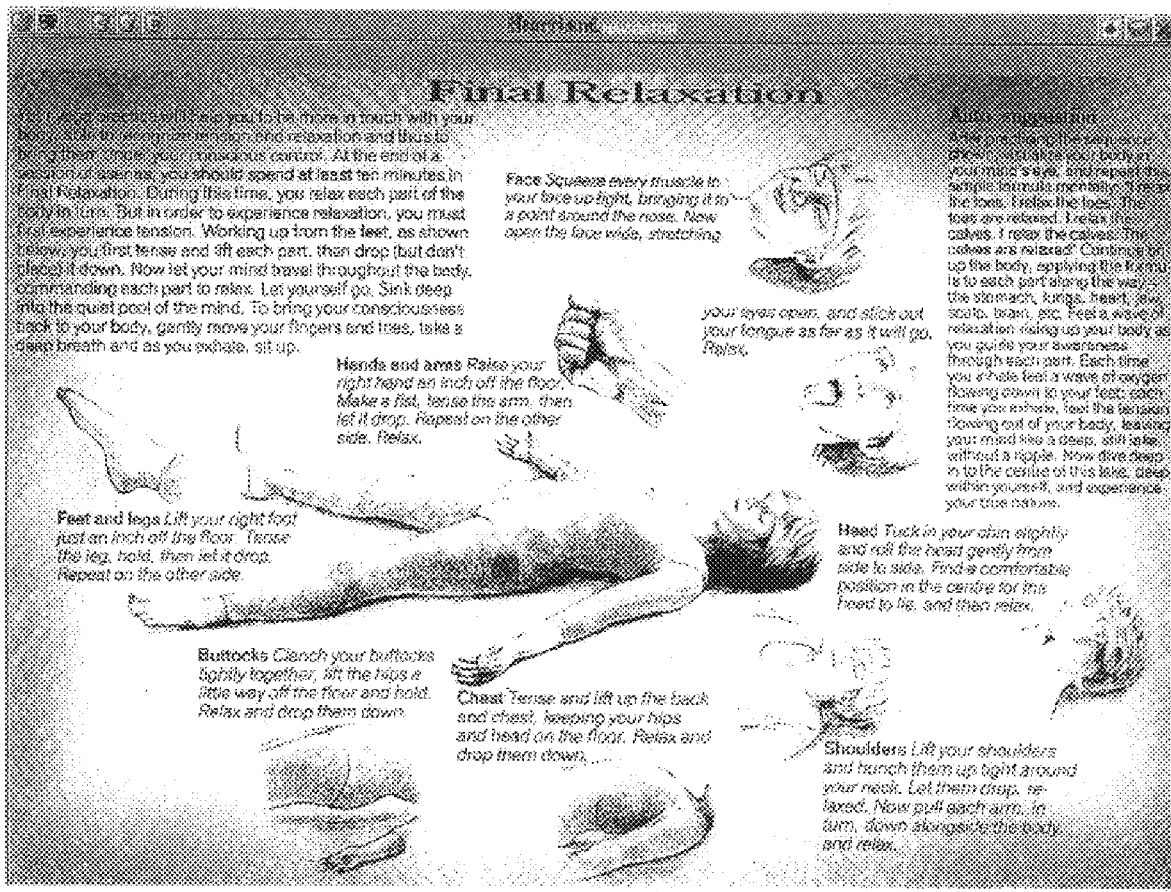
FIG. 31 is a graphical representation of the system's Yoga option.

An expanded illustration of the tranquility park 72 is shown in FIG. 29. Upon selection of the relaxation option 170, an instructional article on the subject is invoked, as shown in FIG. 30. Similarly, upon selection of the yoga option 172, an instructional article about yoga is invoked, as shown in FIG. 31.

Referring back to FIG. 8, the system also gives access to a village library 80 which allows users to do research germane topics. Thus, patients interested in learning more about their medial condition may access the library 80 in order to educate themselves on the topic.

Figure 32:
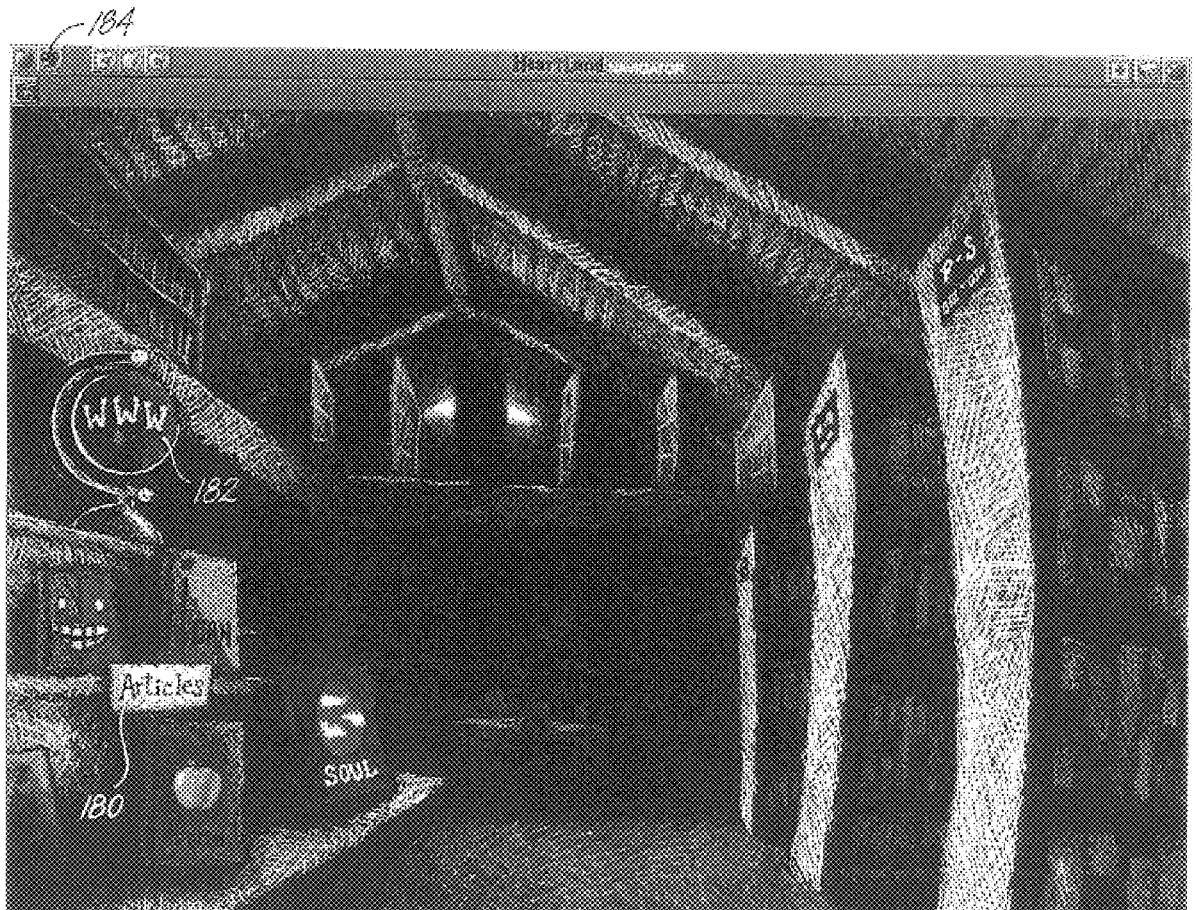
FIG. 32 is a graphical representation of the system's Library option.
Figure 33:
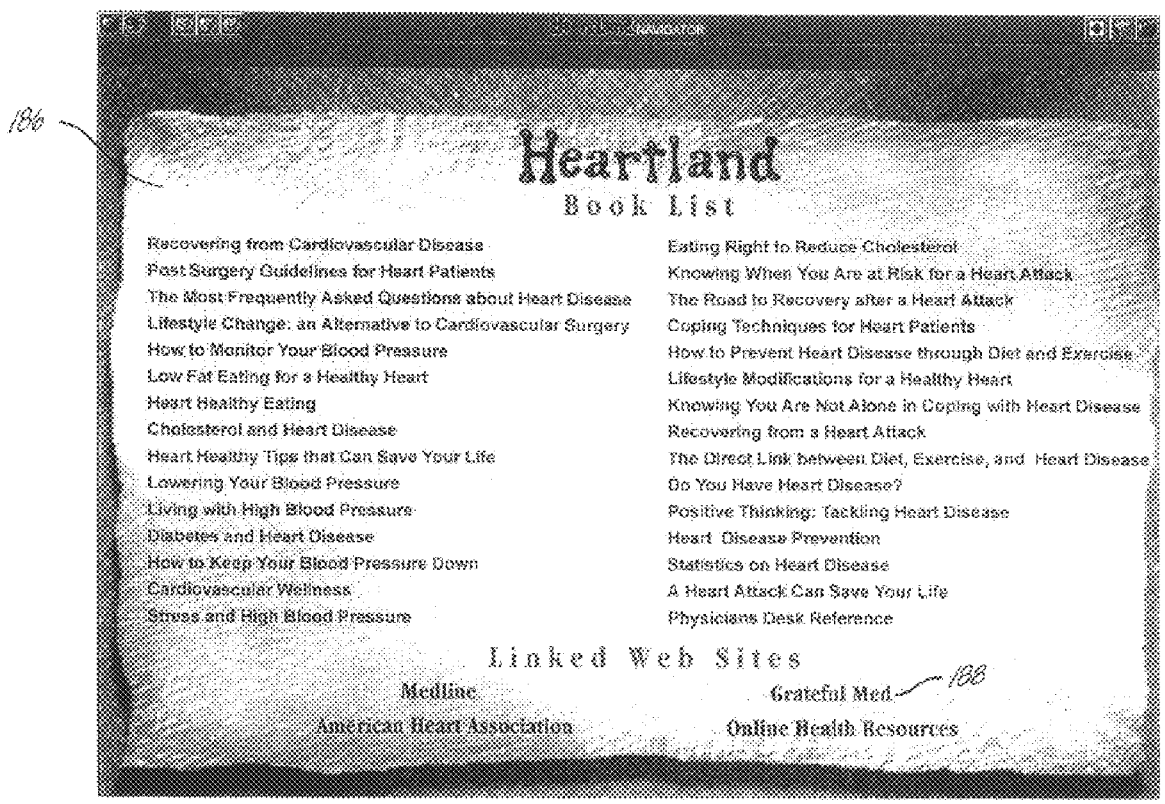
FIG. 33 is a graphical representation of the system's Articles option.

FIG. 32 illustrates the interior of the library 80. From here, a user may select an Articles option 180 to gain access to an available list of articles 186 via his or her CD-ROM, as shown in FIG. 33. The kind of articles 186 available to a user will vary depending on the type of user. For instance, if the user suffers from a chronic cardiac condition, the articles 186 will all relate to such topic. The list of articles 186 is updated on an ongoing basis to reflect new developments and research on the topic.

Users are also provided with hypertext links 188 to other reputable Internet sites devoted to providing medical and health-related information. These Internet sites may also be accessed by selecting the world wide web option 182 as shown in FIG. 32.

Figure 34:
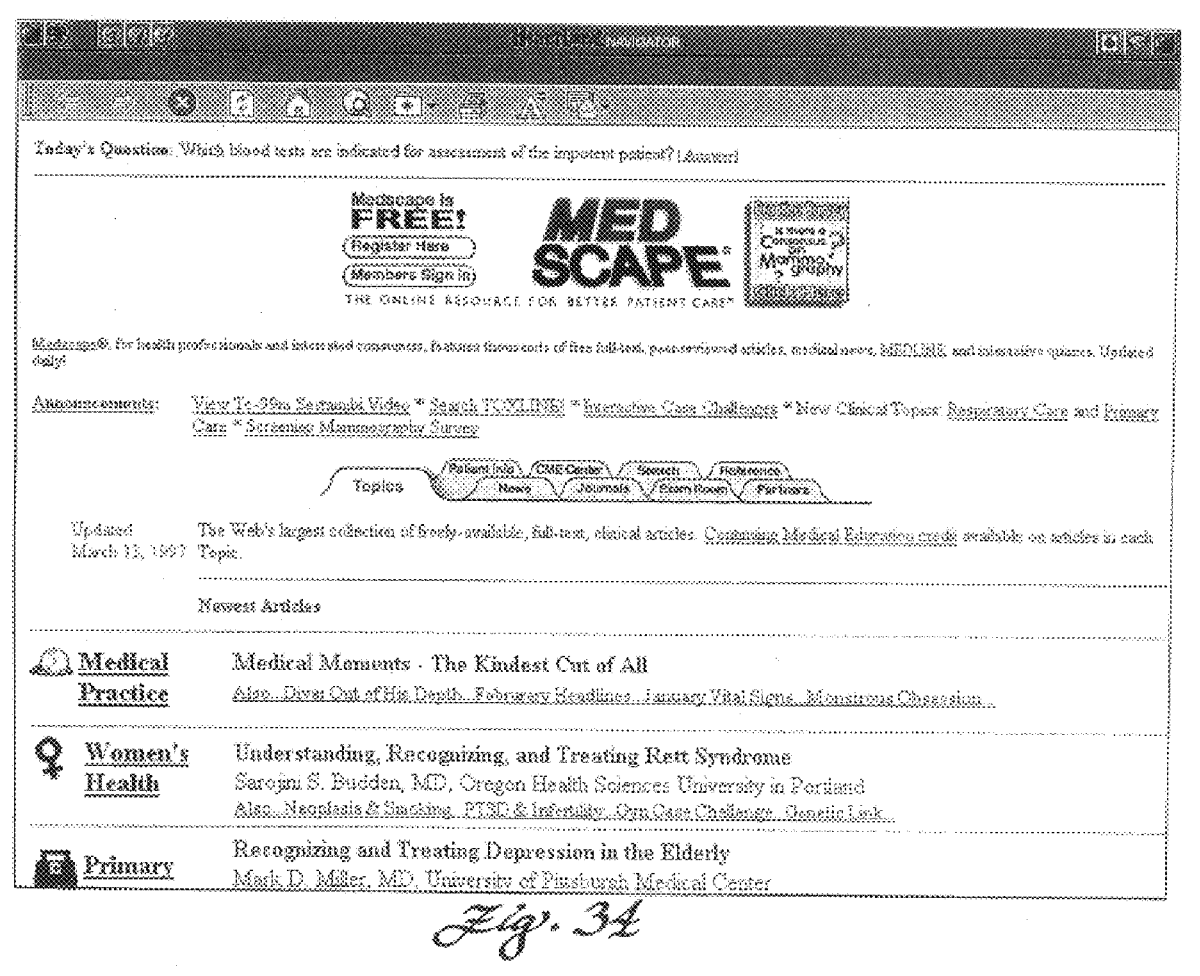

Once linked to an Internet article, a user is taken to a separate web browser from which he or she may navigate the web. FIG. 34 is an example of an Internet site to which a user might get connected upon selection of the world wide web option 182 of FIG. 32.

Furthermore, users have access to a pull-down menu by clicking the menu icon 184. From this menu, users can select various educational topics germane to the user's condition. For instance, an article available through the pull-down menu may teach a user suffering from a chronic cardiac condition how to determine his or her target heart rate zone, as shown in FIG. 35.

Users may also do key word searches to access and print articles of interest, to view featured video clips, or listen to audio clips.

Referring again to FIG. 8, the village store 78 and travel agency 82 are two additional interfaces accessible to users. Upon entering the store 78, users are taken to an in-house or third-party web site through which they may order relevant items, either on-line or by telephone.

Users may also search the store database and view product information, including pictures, descriptions, and prices of products. Moreover, users may view the status of their orders and contact customer service via e-mail or telephone.

Figure 36:
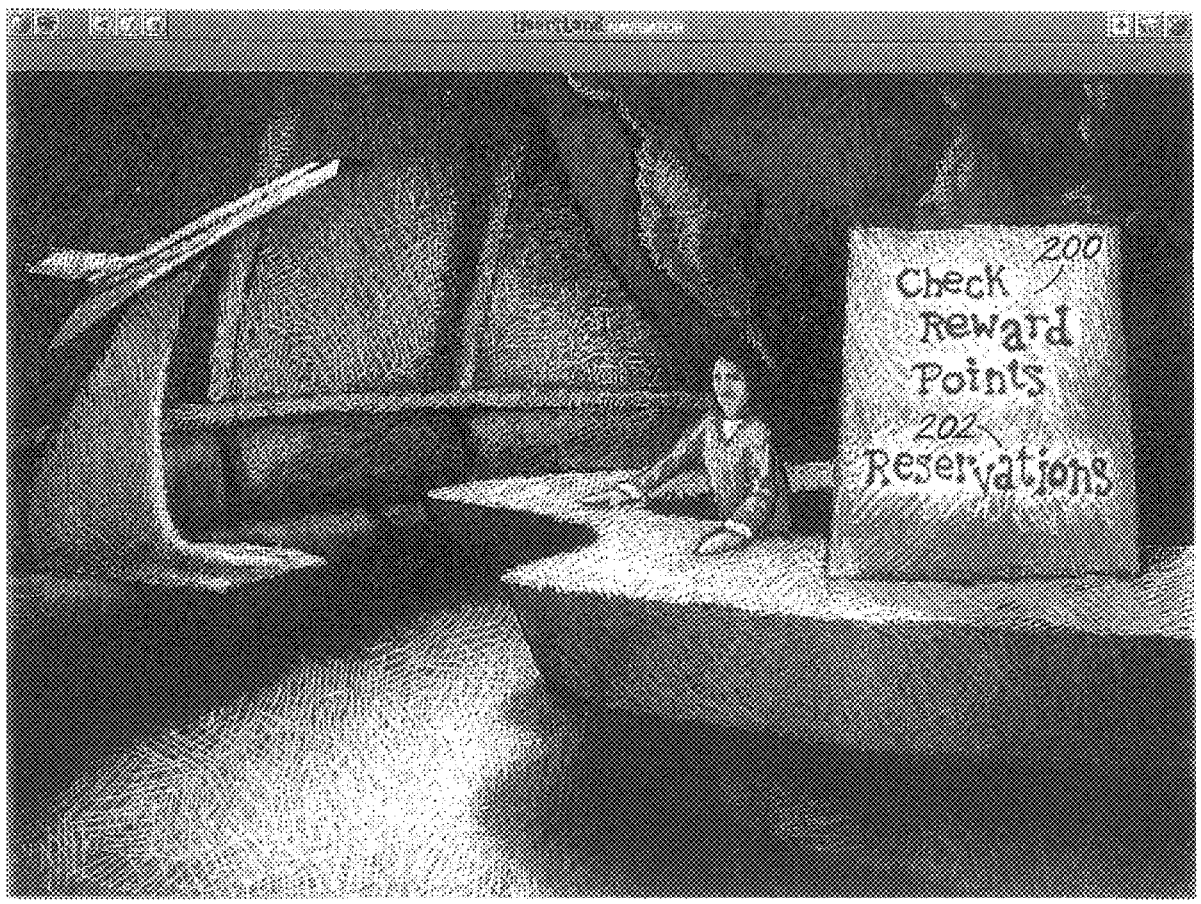
FIG. 36 is a graphical representation of the system's Travel Agency option.

Similarly, when a user enters the travel agency 82, he or she is linked to a third-party co-branded reservation system. FIG. 36 illustrates the inside of travel agency 82. From here, a user may make on-line travel reservations by selecting a Reservations option 202.

A user may also view the frequent flier miles he or she has accrued so far by selecting a Check Reward Points option 200. As discussed above, a user may gain frequent flier miles by good participation in the program and reaching certain milestones.

Although the user-interface for clinical and wellness group members has been described in terms of a village motif, an alternative user-interface could incorporate another alternate embodiment of the system interface shown in FIG. 37. A multi-frame screen is shown which includes: a main navigation area 210; content area 212; message or video screen area 214; and an instructions area 216. The message or video screen area 214 may be used to show advertisements. The instructions area 216 may be used as a "What's New" area or for the bulletin board functionality discussed above for the kitchen 150A (FIG. 22), gymnasium 71 (FIG. 26), and tranquility park 72 (FIG. 29) interfaces.

FIGS. 38–47 and 49–58 illustrate user interfaces for the case advisor and HMO, some of which are also accessible by the patient. Unlike the user interface for patients, the navigation for the physician/case advisor is generally less graphical and more chart oriented.

Figure 38:
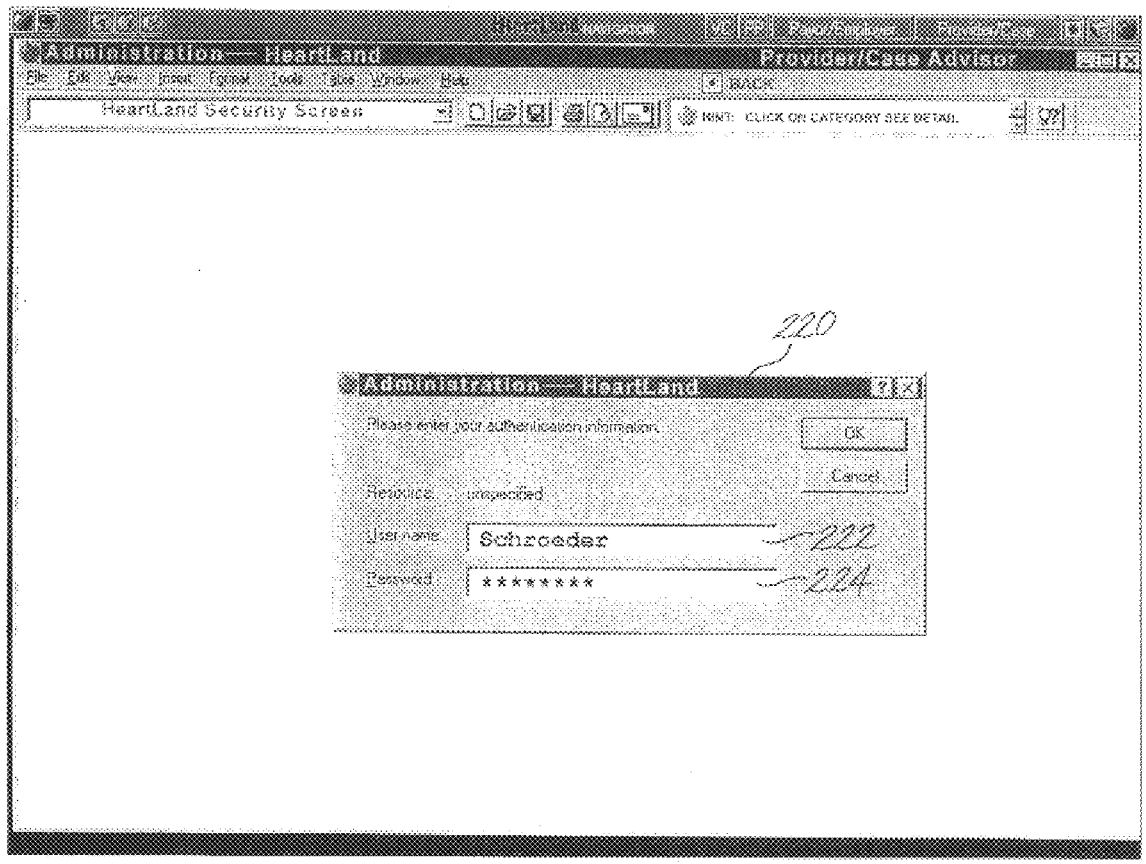
FIG. 38 is a graphical representation of a log-on screen for a physician or case manager in accordance with another aspect of the present invention.

Referring now to FIG. 38, a log-on screen 220 for the user interface for a physician/case advisor is shown. The screen 220 requires the physician or case advisor to input their name 222 and corresponding password 224. Screen 220 thus acts as a security measure by ensuring that only legitimate users are able to gain access to the system.

Figure 39:
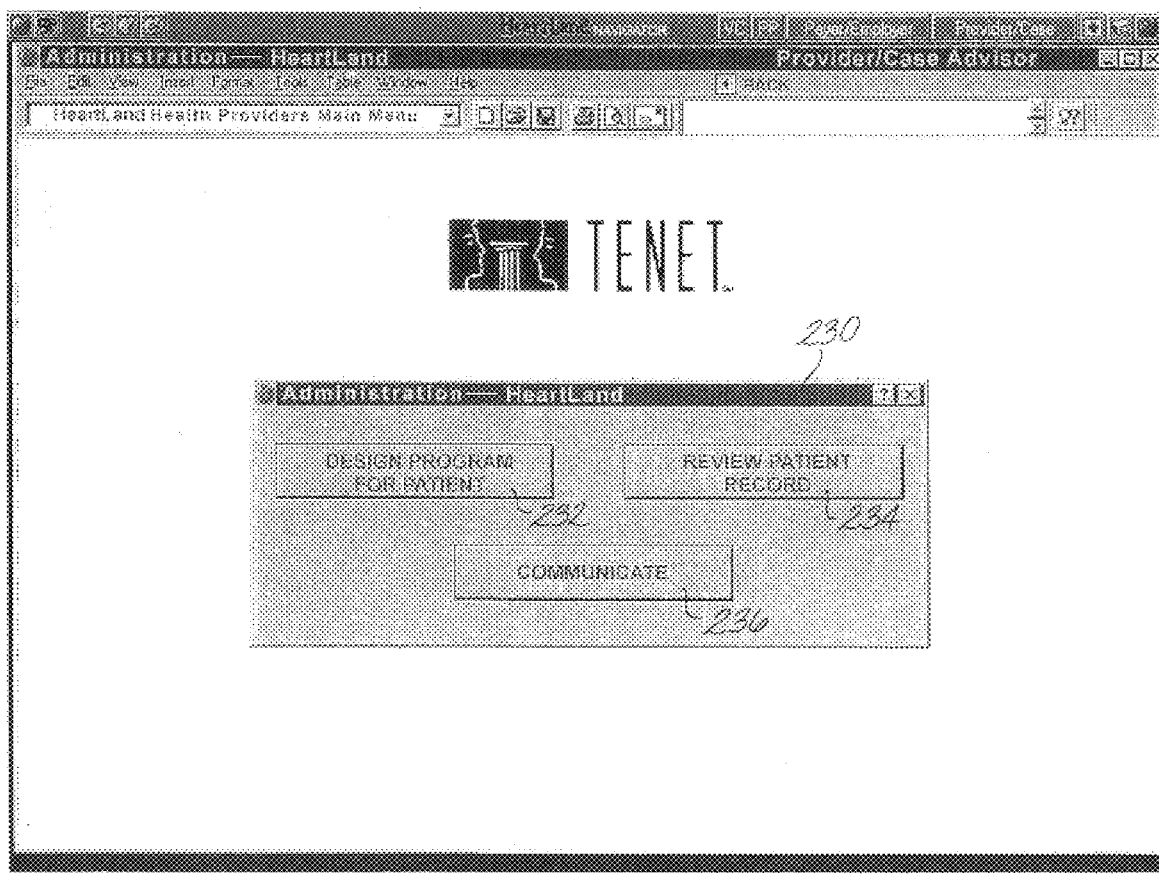
FIG. 39 is a graphical representation of a main menu available to a physician or case manager.
Figure 41:
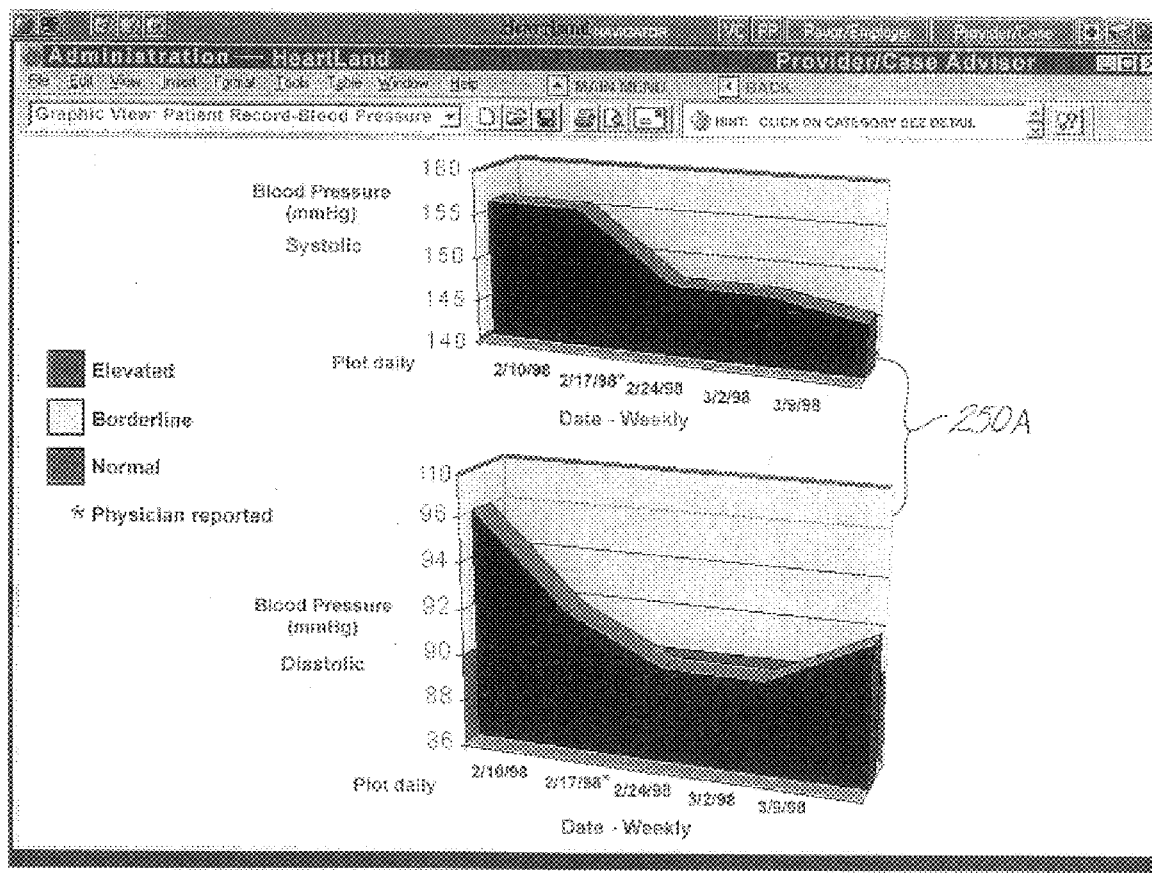
FIG. 41 is a graphical representation of a blood pressure chart for an exemplary patient.
Figure 42:
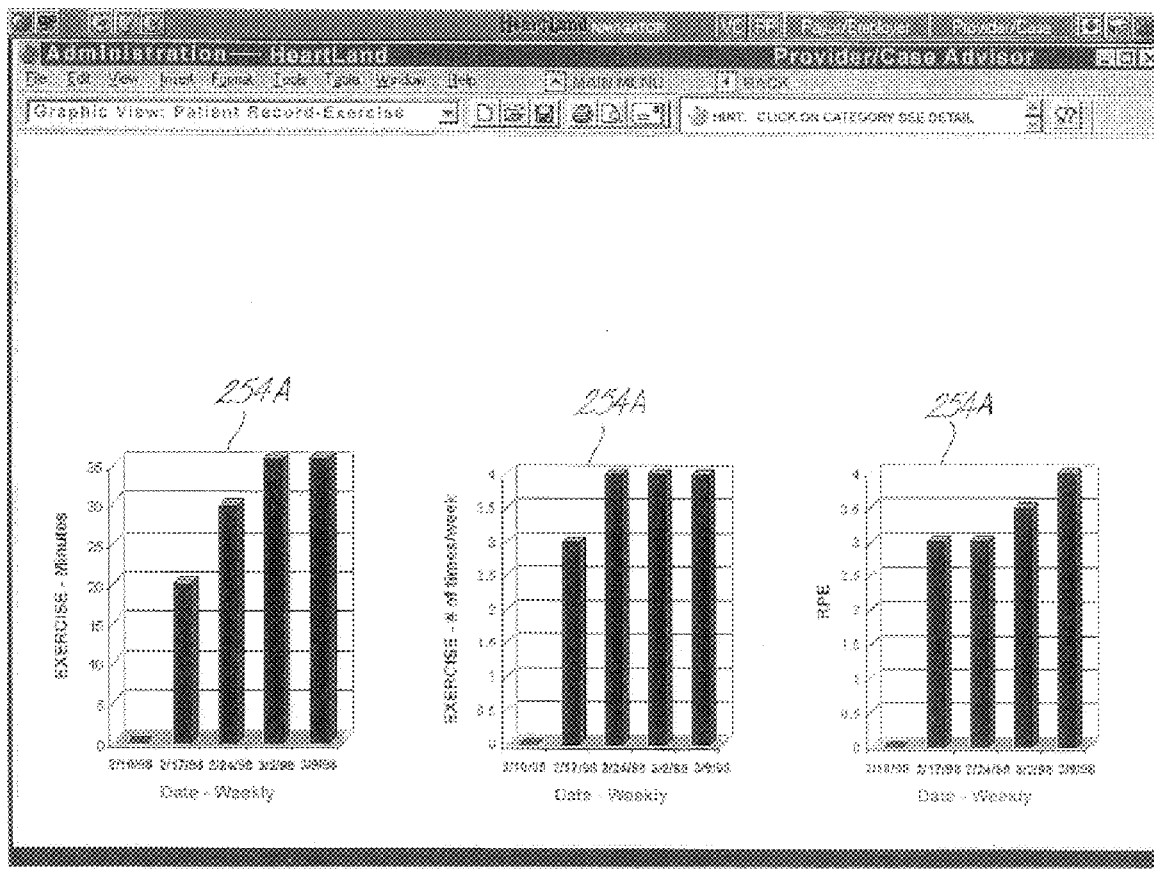
FIG. 42 is a graphical representation of a physical activity chart for an exemplary patient.
Figure 43:
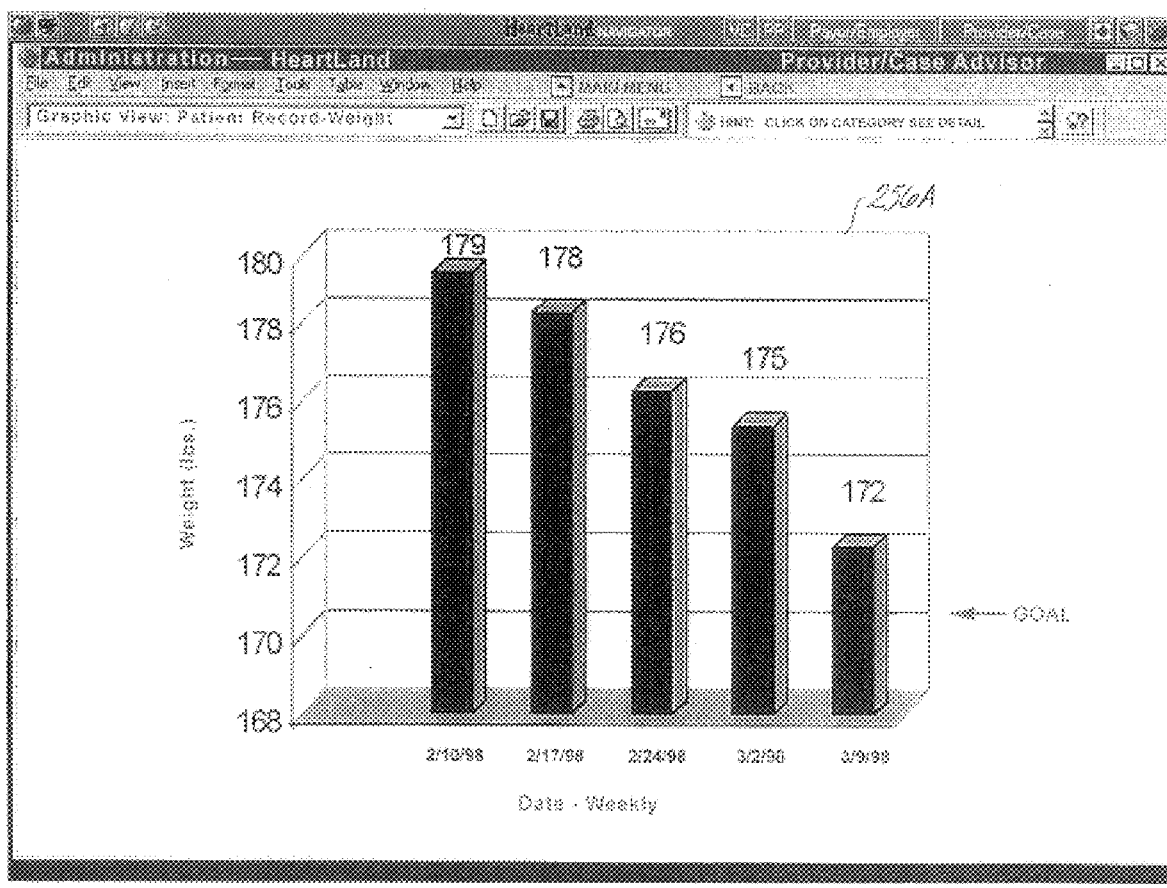
FIG. 43 is a graphical representation of a weight chart for an exemplary patient.

Referring to FIG. 39, an initial screen containing a main menu 230 of the options available to the physician/case advisor follows the log-on screen 220. A Design Program For Patient option 232 allows a physician/case advisor to create a new program or modify an existing program for a patient, as described above in conjunction with FIGS. 3–6.

A second option within the main menu 230 is a Review Patient Record option 234 which allows a physician/case advisor to review the health record of a particular patient.

A list of current patients (not shown), substantially similar to the list shown in FIG. 4 follows upon selection of a Review Patient Record option 234.

Figure 40:
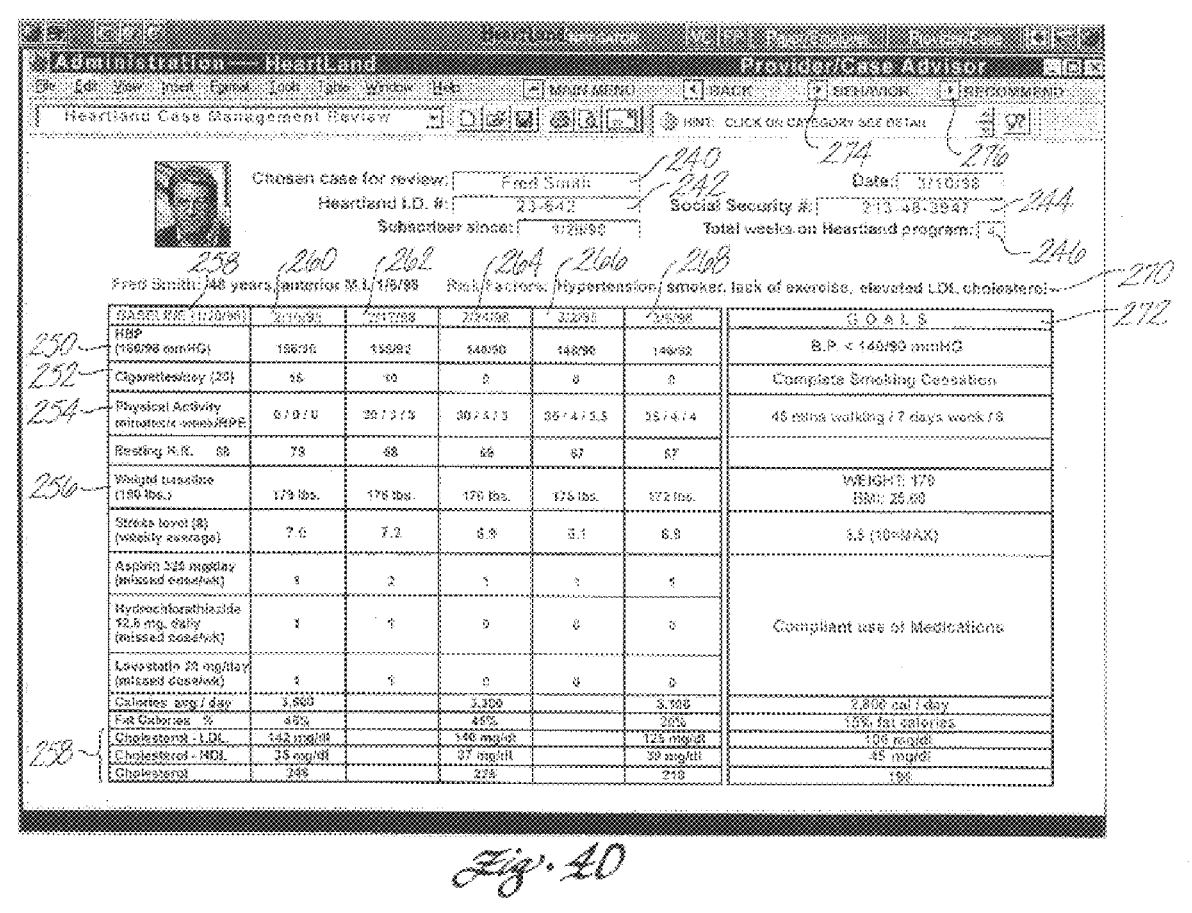

Referring now to FIG. 40, a health record of an exemplary patient is shown. The record may provide identifying information, including the patient's name 240, subscription ID 242, and social security number 244. Furthermore, information as to the total amount of time that the patient has been participating in the program may be given as shown at 246.

Column 258 shows the patient's vital signs and other health-related factors, such as blood pressure 250, number of cigarettes smoked per day 252, amount of physical activity 254, weight 256, and cholesterol level 258. Some of these factors may be monitored and reported on a weekly basis, as shown in columns 260–268. Other factors, such as the patient's cholesterol level 258, may be monitored and reported on a bi-weekly basis, as shown in columns 260, 264, and 268. The ultimate goal to be achieved in each of the specified areas is given in column 272.

A list of the risk factors which may affect the patient's recovery may further be pin-pointed as shown at 270.

Figure 44:
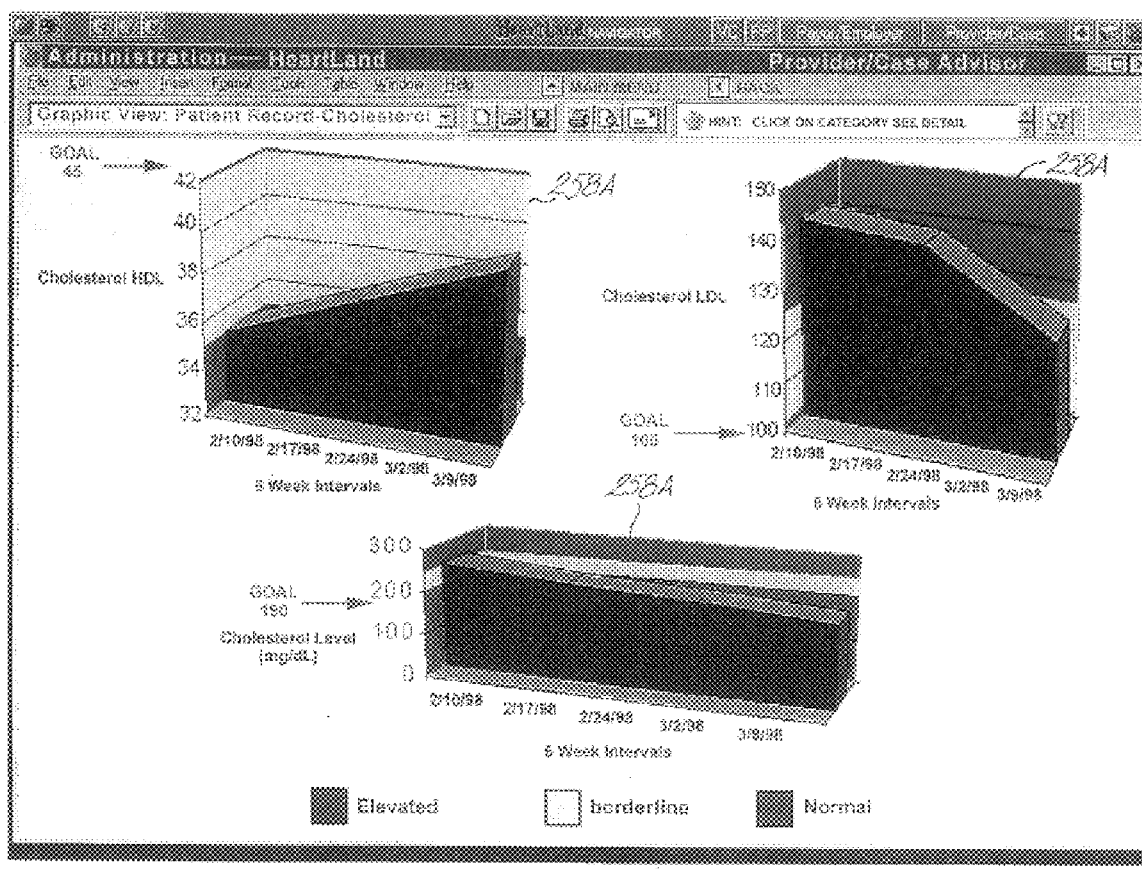
FIG. 44 is a graphical representation of a cholesterol chart for an exemplary patient.

Vital signs may be represented graphically for the patient, physician and case advisor. These may include charts or graphs of the patient's blood pressure 250A (FIG. 41), physical activity 254A (FIG. 42), weight 256A (FIG. 43), and cholesterol level 258A (FIG. 44). These graphs allow the physician/case advisor to review and grasp the patient's progress visually over a period of time, and help him or her determine how the patient is doing in relation to the ultimate goals that are to be achieved in the charted areas.

Referring again to FIG. 40, a physician/case advisor is also given an option 274 to assess the patient's behavior. Upon selection of this option, the system provides a behavioral change assessment form 305 like the one shown in FIG. 45. This form 305 is used to determine how inclined the selected patient is toward complying with the recommended program. In the preferred embodiment, on-line questionnaires are submitted to the patients, asking them to rate their behavioral intention 300, self-efficacy 302, and social support 304. Alternate forms of evaluation may also be used to assess the likelihood of a patient's compliance with the program.

The system periodically assesses and reports the patient's behavioral change as shown in columns 306 and 308. The desired goals 310 are also listed to monitor whether the patient is making progress towards them. If a patient continues to score low on the behavioral change assessment form 305, this may indicate that he or she is unable to change his or her lifestyle, and lead to the conclusion that the patient should be taken off the system.

The system generates reports on patient progress based on the data shown in FIGS. 40–45, as frequently as the physician desires. These reports can be received via either e-mail or facsimile. The frequency of reports will depend on the needs of the particular patient, and may be triggered by the achievement of goals or the setting off of alarm signals as described above.

The system can also generate regularly scheduled reports for a physician's review on a default basis, depending on a patient's needs. For example, patients who are relatively ill can be reviewed twice a week or more, even if no warning signals occur.

Figure 46:
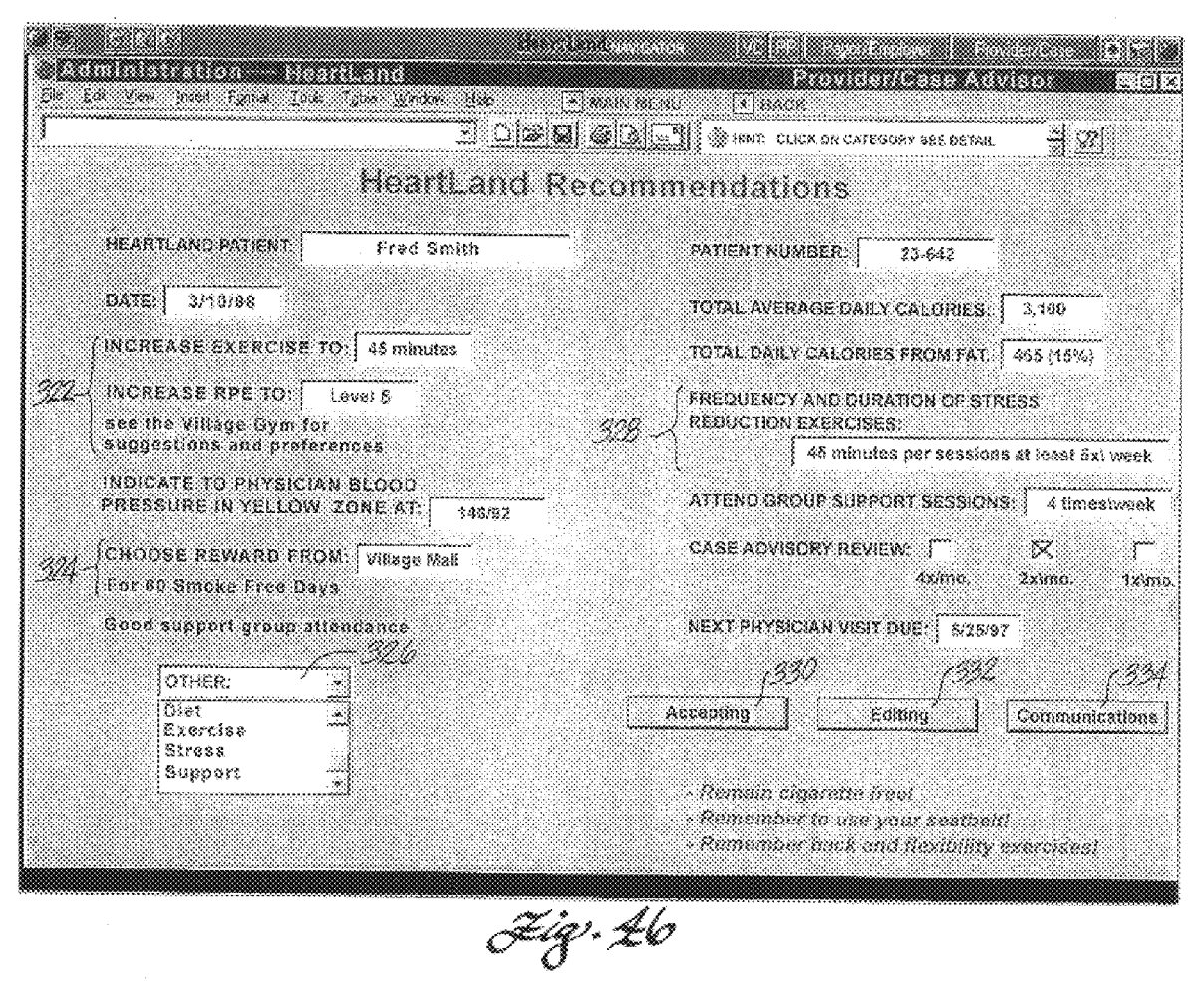

Upon receiving feedback from the system regarding changes to a patient's behavior modification program, a physician or case adviser may want to make recommendations about the program. FIG. 46 shows an exemplary recommendation screen which follows the selection of a Recommend 276 option of FIG. 40. If, for example, a patient initially placed on a program of walking 15 minutes three times a week loses 5 pounds and lowers his or her blood pressure, the system might generate a report to the physician recommending an increase in the patient's walking time to 45 minutes per session as shown at 322. The system may further make recommendations as to the frequency and duration of stress reduction exercises 328 as well as on other areas of the program as shown at 326. The physician reading the report can accept 330 or modify 332 the recommendations.

The system's reporting features enable a physician to handle more patients in the same amount of time without decreasing the quality of care. The system also allows for a patient feedback loop independent of this self-monitoring capability. If the patient has a difficult night, for example, he or she can send an e-mail through the system directly to the case advisor or the physician via the mail 98 (FIGS. 9, 16–20) or post office 74 (FIG. 8) interfaces.

Once the physician/case advisor is satisfied with the recommendations, he or she may electronically communicate 334 program changes to the subscriber.

FIG. 46 also shows an example of a patient who has earned reward points 324 for not having smoked for 60 days.

The reward points shown here are to be cashed in at the village store 78 shown in FIG. 8.

Figure 47:
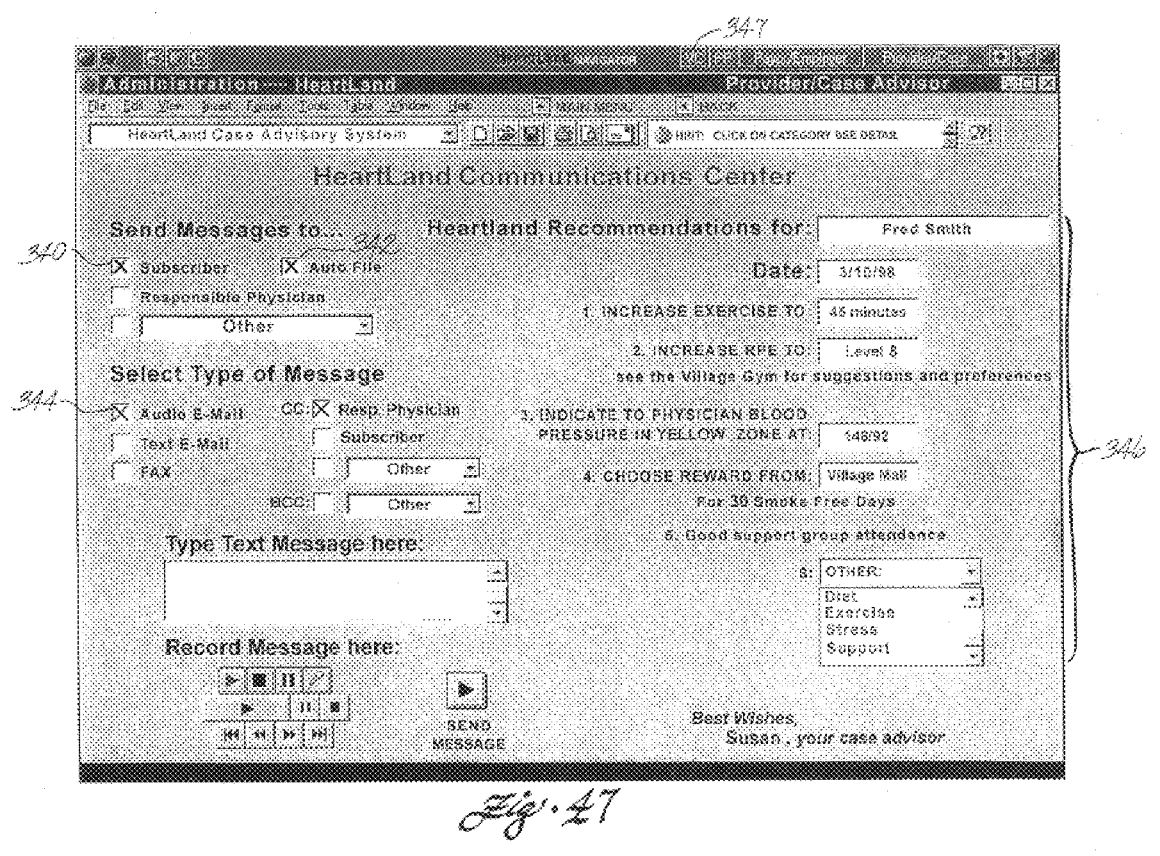

Referring to FIG. 47, the system presents a message screen upon the selection of a communications 334 option of FIG. 46. The case advisor may send the recommendation 346 made by the system and reviewed and/or modified by the physician, to the subscriber 340 with an attached audio e-mail message 344, or alternately via text e-mail or facsimile. A copy of the recommendation 346 and message 344 may also be stored in the system's database 342.

Physicians/case advisors may further communicate with patients by video conferencing. An existing third-party video conferencing package may be integrated to the system to allow the video conferencing feature. The minimal requirements for a PC to support the video conferencing capability is a clock cycle of 90 megahertz, 24 megabytes of random access memory, a color camera, a video capture board, an audio board, a video input capture board, and an ISDN line. The technical specification may change as technology affecting bandwidth and/or data compression changes.

Figure 48:
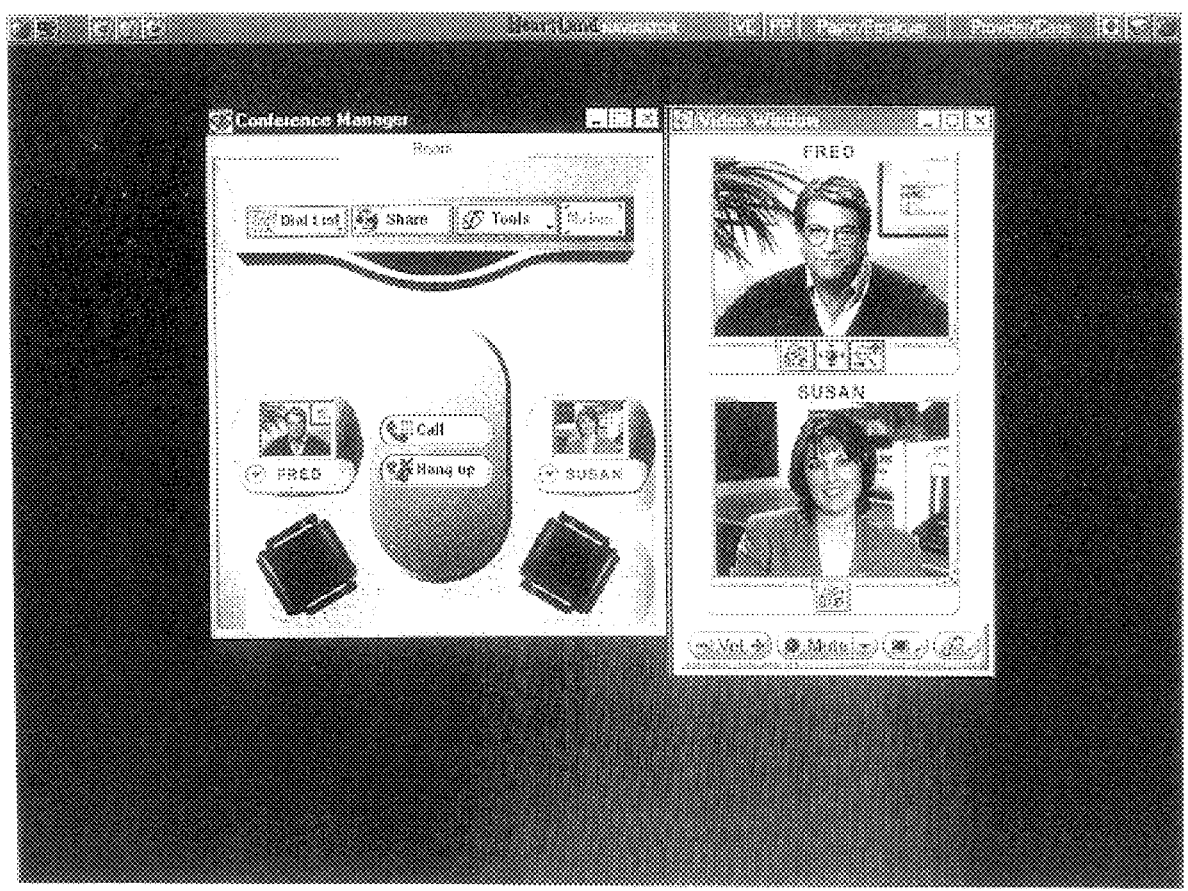
FIG. 48 is a graphical representation of the system's Video Conferencing option.

As shown in FIG. 47, the video conferencing feature may be accessed upon selection of a video conferencing option 347. A video conferencing manager, like one illustrated in FIG. 48 may then be used to conduct the video conference.

A health plan payor, such as an HMO, insurance company, or self-insured employer, may also access the system. Information that is released by a patient may also be sent electronically to the health plan payor. The information can then be combined with the provider's information to analyze individual patients or aggregate results of all people on the program. The analysis may include, for example, cost per patient, cost for patients in each category or group, and physician utilization. The system's relational database that allows for the custom gathering of data, depending upon the requirements of the health plan. The system may also provide aggregate reports to the health plan payor for management review and cost control purposes. A health plan payor may be less interested in looking at individual patient files and more interested in looking at information as to the number of subscribers on the system, the cost of keeping the subscribers on the system, and how this cost compares to that incurred by patients who are not on the system. At the same time, several layers of electronic security measures insure the individual patient's privacy by strictly segregating the type of information available to the various parties who have access to the system.

Figure 49:
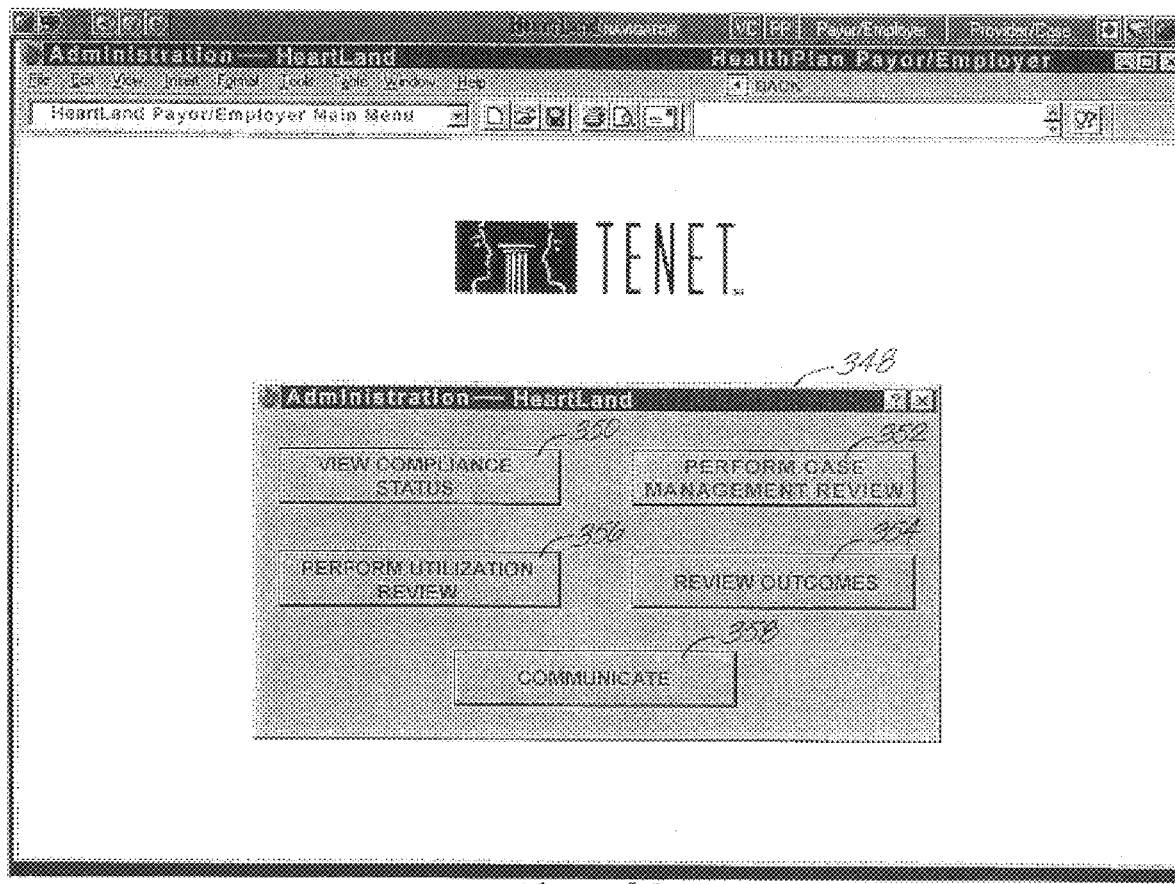
FIG. 49 is a graphical representation of a main menu available to a health plan payor or employer.

The user interface for the health plan payor is similar to the user interface used by a physician/case advisor. When the health plan payor signs onto the system, a main menu screen with a list of options available is provided, as shown in FIG. 49. From here, the payor may choose to view overall compliance status 350, perform case management review 352, perform an utilization review 356, review outcomes 354, or communicate 358, each of which options is described in further detail below.

Upon selection of a view compliance status 350 option, the health payor views current compliance status based on pre-determined categories 360, as shown in FIG. 50. For each category, information as to the total number of eligible patients 364, number of participating patients 366, participating patients complying with the program 368, participating patients put on probation due to lack of compliance 372, and patients terminated 376, may be displayed.

A comparative cost analysis screen is also invoked via a view comparative costs option 362. FIG. 51 shows an example of the cost of maintaining patients on the system. The total cost 380 may be compared against costs incurred by a control group of patients who have not subscribed to the system 382. Comparative savings achieved by use of the system are shown in column 384.

Referring back to FIG. 49, the main menu 348 also includes a perform a case management review 352 option. A list of current patients (not shown), substantially similar to the list shown in FIG. 4, follows selection of this option.

Figure 52:
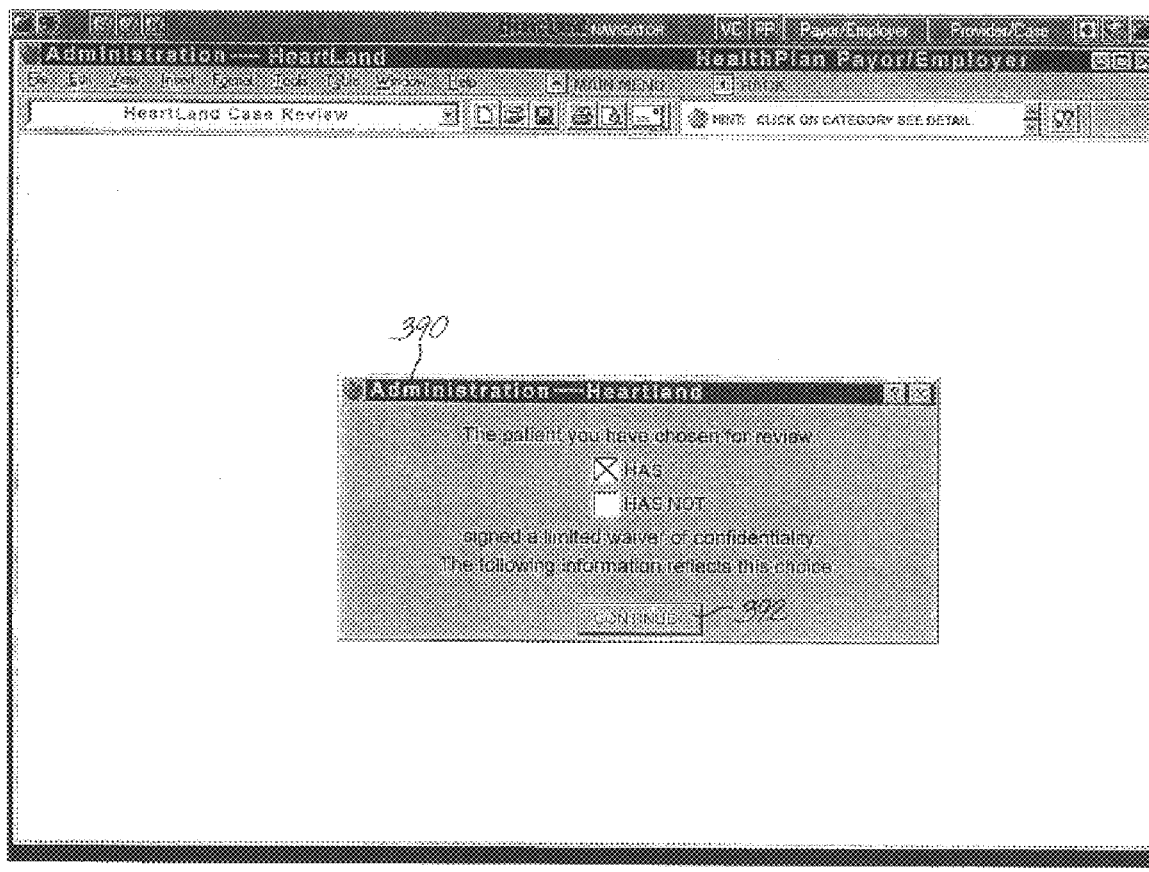
FIG. 52 is a graphical representation through which the system indicates whether the patient has executed a limited waiver of confidentiality.

Once a patient file has been selected, a confidentiality waiver information 390 is displayed, as shown in FIG. 52. A patient will be assured confidentiality and privacy in the areas where waiver has not been given. For instance, portions of the patient's journal will be kept confidential and unavailable to the health plan payor, ensuring that patients remain open and honest in making daily journal entries.

Figure 53:
FIG. 53 is another graphical representation of an exemplary patient record.

Upon selection of a continue option 392, a screen similar in content to the screen shown in FIG. 40 is shown in FIG. 53. As with the user interface for physicians/case advisors, indications of the patient's blood pressure level 404, physical activity 406, weight 408, and cholesterol levels 410 over time, are given. These may also be represented graphically to the health plan payor in a form substantially similar to FIGS. 41, 42, 43, and 44 respectively.

A health plan payor, however, has a review costs option 400 which is not available to a physician/case advisor.

Figure 54:
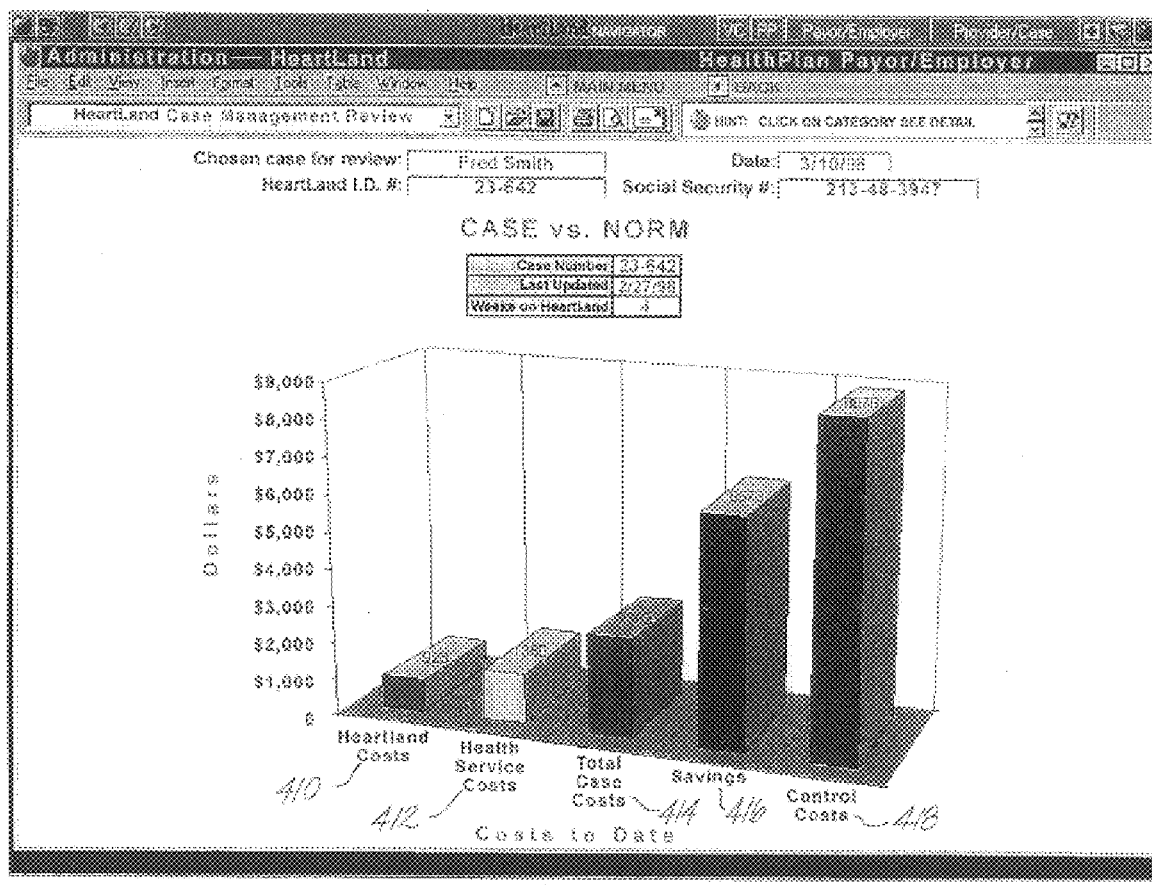
FIG. 54 is a graphical representation of the system's Review Costs option.

FIG. 54 illustrates an exemplary screen viewable upon selection of the review costs option 400 of FIG. 53. Shown here is information as to the costs incurred to date in maintaining the selected patient on the system. The system costs 410, health service costs 412, and total costs 414 are represented in a bar graph format in this particular example. The cost incurred by a control group patient who is not on the system is also shown 418. This cost is compared to the total costs 414 and the amount of savings 416 thus achieved, and is also displayed in a bar graph format.

Figure 55:
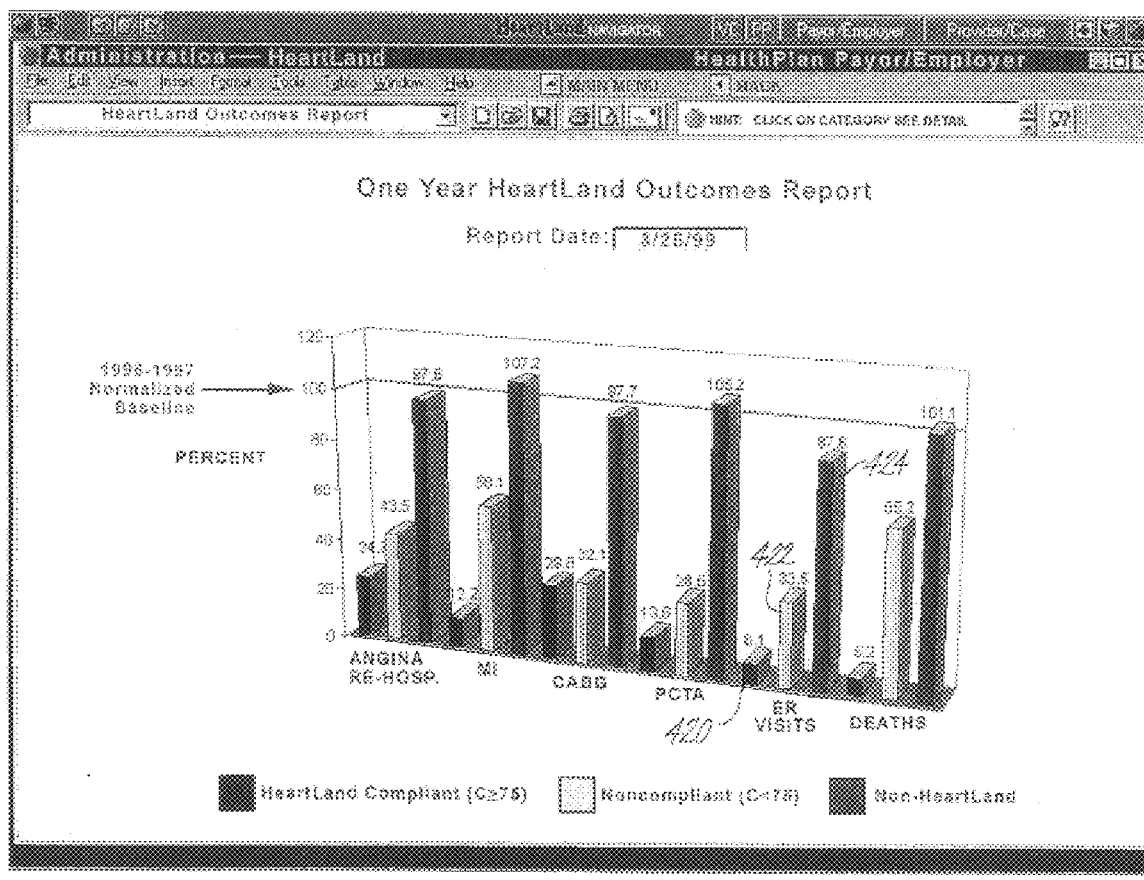
FIG. 55 is a graphical representation of the system's Review Outcomes option.

Referring back to FIG. 49, another option provided by the main menu 348 is a review outcomes 354 option, which provides a screen like the one shown in FIG. 55 with information as to the various patient outcomes, based on various pre-determined categories. For instance, information as to the percent of compliant subscribers who had an emergency room ("ER") visit 420 is shown. This information may be compared against ER visits made by non-compliant subscribers 422 and control group patients who have not subscribed to the system 424.

Figure 56:
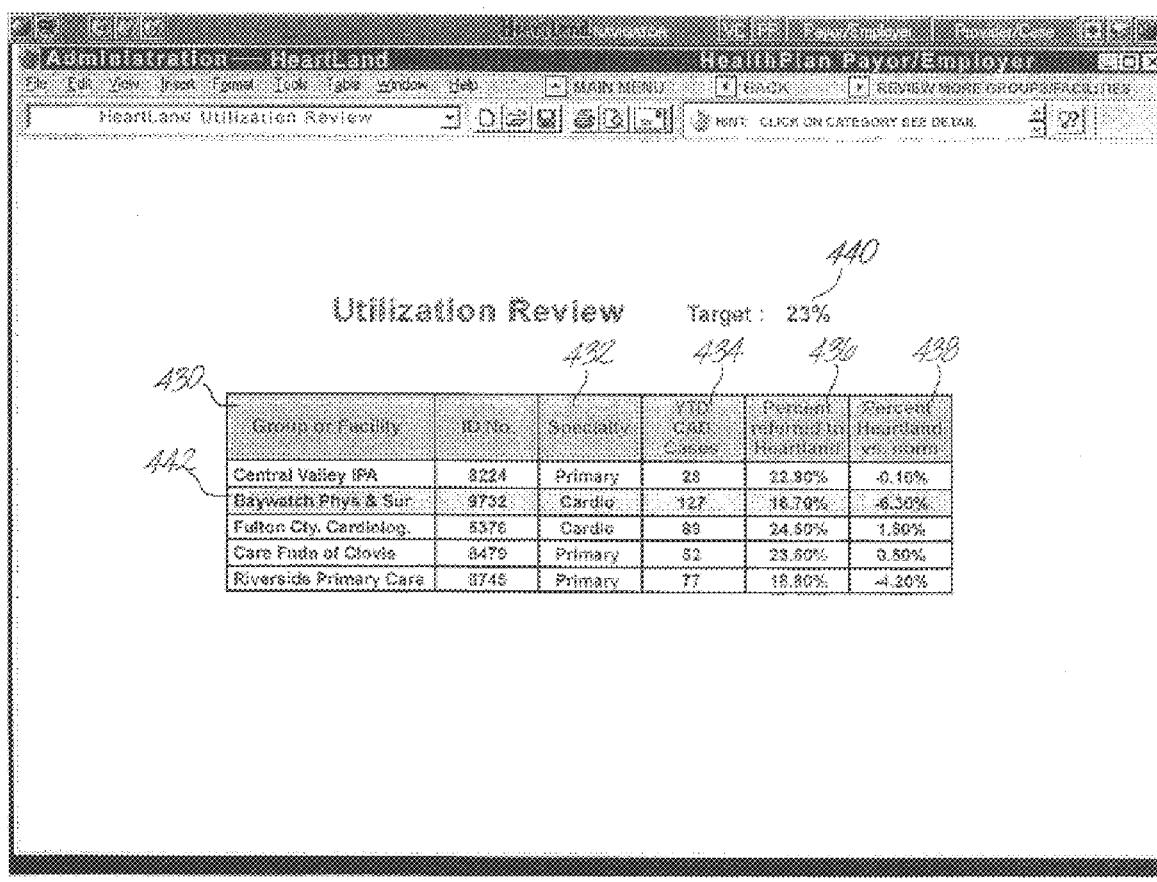
FIG. 56 is a graphical representation of the system's Perform Utilization Review option.

Referring back to FIG. 49, the main menu 348 also provides for a utilization review 356 option. As shown in FIG. 56, upon making this selection, a screen appears with information including the name of the group or facility using the system, this group or facility's specialty 432, the number of cases to date 434, the percentage of cases referred to the system 436, and how this percentage compares 438 to the targeted utilization percentage 440.

Figure 57:
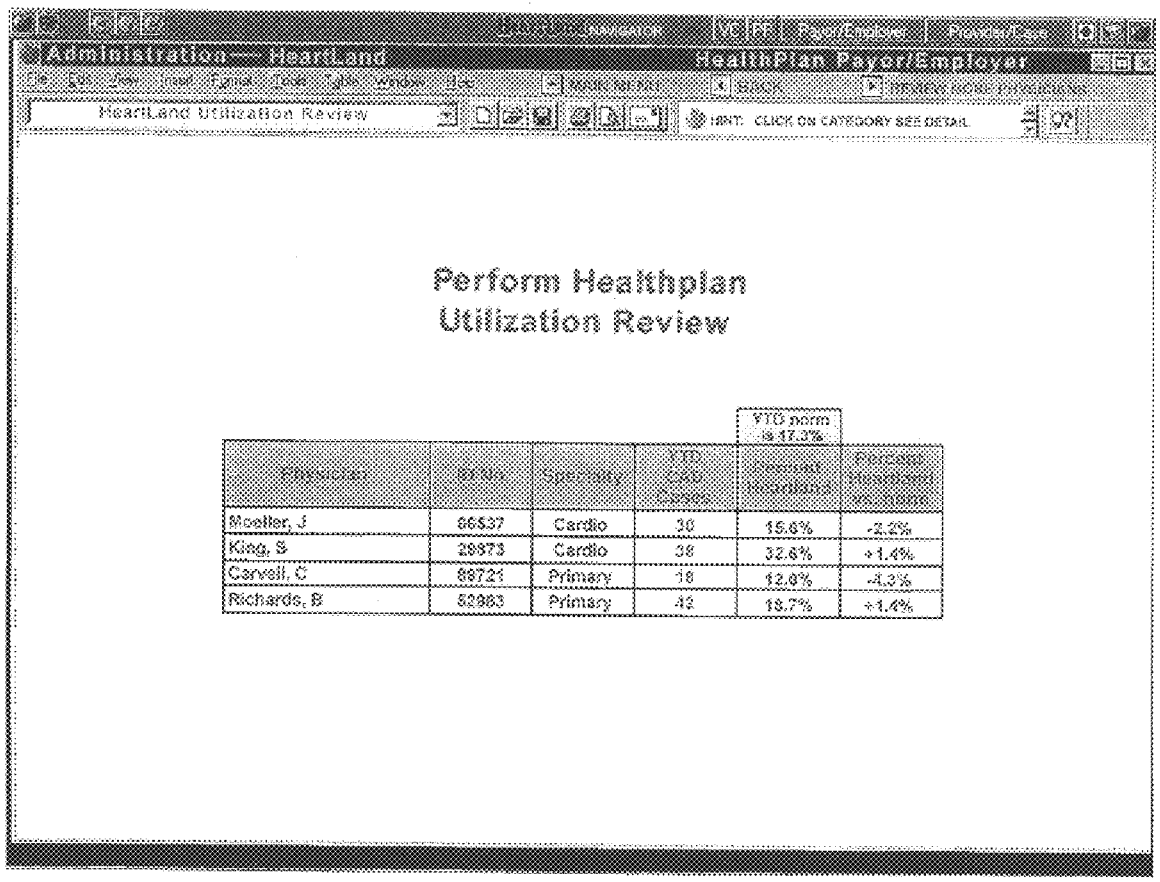
FIG. 57 is a graphical representation upon selection of an exemplary physician group of FIG. 55.

Upon selection of a particular group or facility 442, the same type of information for the doctors within the selected group or facility 442 may be obtained, as shown in FIG. 57.

Figure 58:
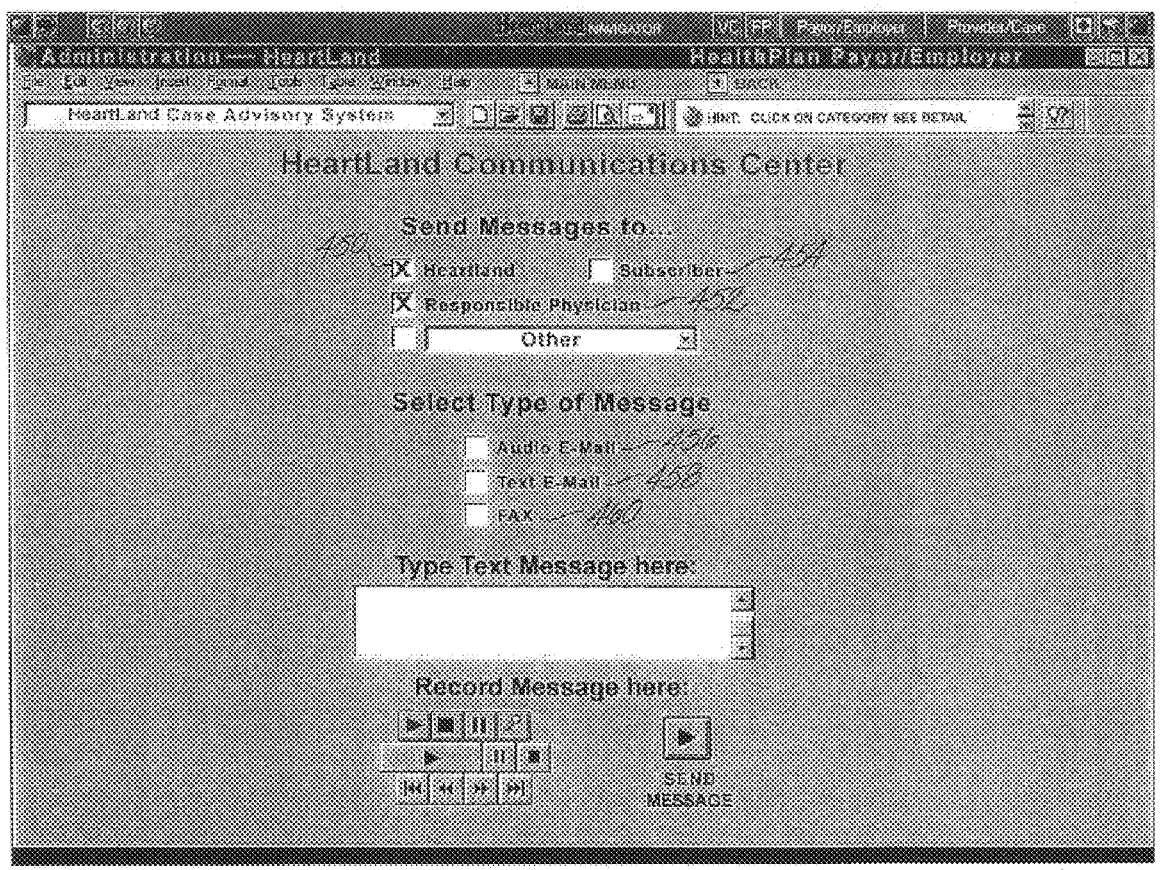
FIG. 58 is an expanded graphical representation of a Communicate option of FIG. 48.

The main menu 348 in FIG. 49 further provides a communicate 358 option leading to FIG. 58. The health plan payor may send an audio e-mail 456, text e-mail 458, or fax 460 to the case advisor 450, responsible physician 452, or subscriber 454 as shown here.

In this way, the system provides an on-going loop of compliance monitoring and feedback to help the patient make difficult lifestyle changes. Once the patient has achieved the desired goals, he or she can continue to use the system as a health maintenance or wellness program. An aim of the system is to educate and motivate patients to take control of their lives and improve their health by modifying their behavior and changing their lifestyles.

Figure 59:
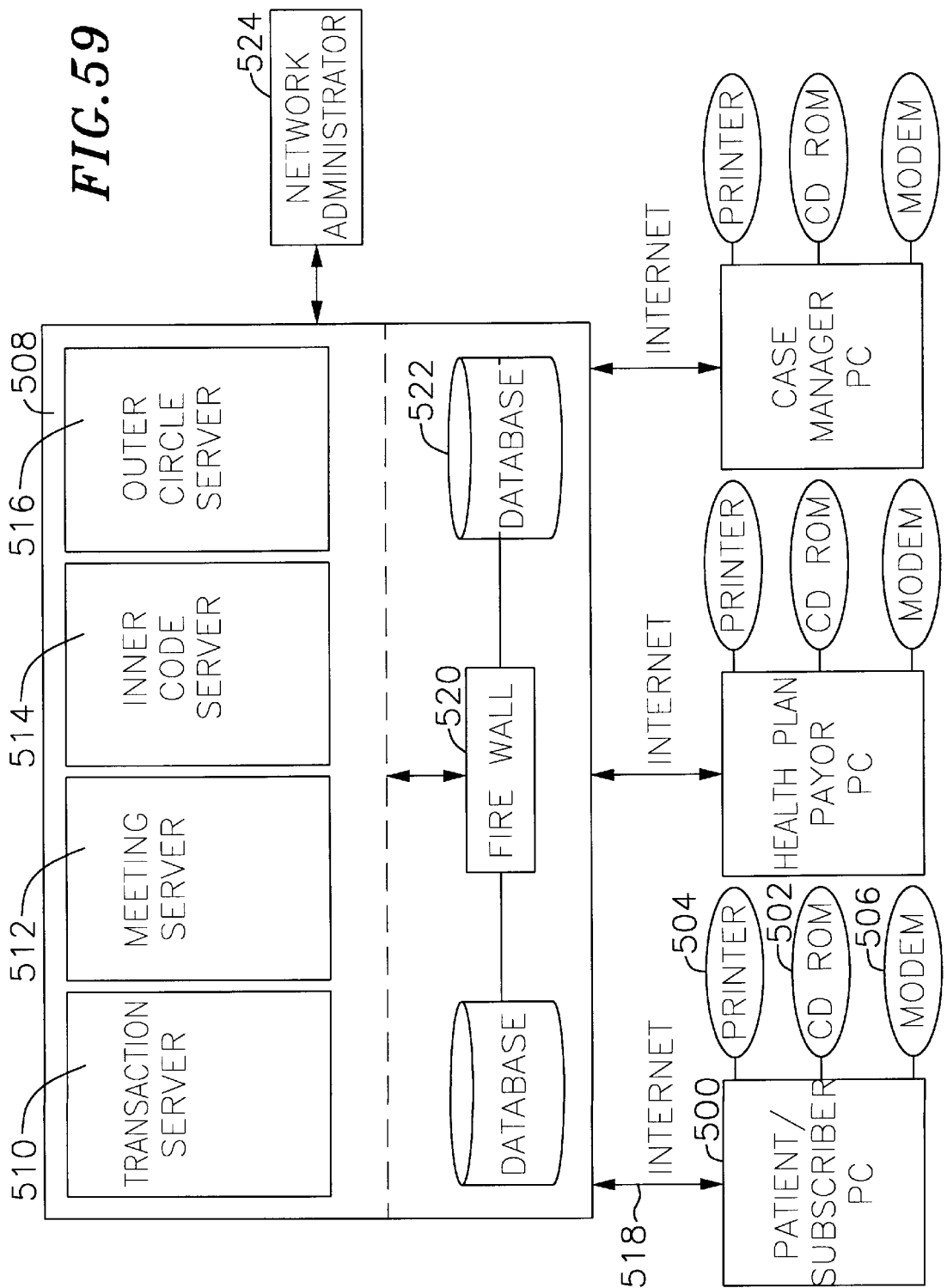
FIG. 59 is a block diagram of the therapeutic behavior modification program's compliance monitoring and feedback system.

FIG. 59 is a block diagram of the present system. It will be apparent to those skilled in the art that the invention described herein may be implemented on various platforms. In a preferred embodiment, however, patients, physicians, case advisors, and health plan payors have access to a PC 500 with a Pentium microprocessor. The PC 500 contains audio and CD-ROM 502 capabilities. However, a PC 500 may have other multimedia capabilities including video display and capture capabilities, microphones, etc. The PC 500 is further connected to a printer 504 for generating hard copies of any data accessible by the computer.

In a preferred embodiment, the operating system utilized by the PC 500 is a windows-based operating system, preferably Windows 95.

In the preferred embodiment of the invention, each PC 500 is electronically linked to network server 508 via the Internet 518. Contained in each server 508 is a transaction server 510, meeting server 512, "inner circle" server 514, and "outer circle" server 516. The transaction server 510 is utilized to handle secure purchases via the store 78 (FIG. 9) or travel agency (FIG. 36) interfaces.

The secure meeting server 512 is dedicated to implementing the meeting room 96 and coffee shop functionalities discussed in reference to FIGS. 9, 14, and 15. The secure "inner circle" server 514 is dedicated to handle sensitive data, such as medical records.

Other servers may be added as needed. For instance, there may be a separate media server to handle the audio and video functionalities of the system.

Communication via the Internet 518 is achieved in the preferred embodiment of the invention through telephone lines by means of a high-speed modem 506 connected to the PC 500. Alternatively, satellites, television cable systems, and ISDN lines may be utilized to access the Internet 518. Standard TCP/IP is utilized as the protocol to communicate between the servers 508 and a PC 500 via the Internet 518.

The network server 508 may be located at a health plan payor facility with an independent third party that acts as an Internet Service Provider or elsewhere. The servers 510–516 have access to one or more relational databases 522 (such as SQL) that contain all the health plan data, including information input to the journal and schedule book information. For example, pertinent information from a patient's journal will be uploaded to the server and downloaded to the physician and case advisor. Information provided by the physician will also be uploaded to the same server. System data will be downloaded to the case advisor on a periodic basis for review.

All the information needed by a user of the system is located in the databases 522 or on CD-ROM and/or DVD distributed to the users on a periodic basis, or, as technology permits, via streaming audio and video. For instance, in the presently preferred embodiment, the video and audio clips available to a chairperson 114 for conducting meetings (FIG. 14), or via the kitchen (FIGS. 21, 22), gym (FIG. 26), tranquility park (FIG. 29), and library (FIG. 32) interfaces is located on CD-ROM or DVD. However, with the emergence of ISDN, cable modem, XDSL, and direct satellite delivery, it is anticipated that the system will be capable of sending streaming video and audio over the network.

There are three levels of security implementation to help achieve secure transmission of data to and from the servers 510–516, as well as to ensure that only authorized users may access the databases 522. User security for patients, physicians/case advisors, and health plan payors is assured by a two tier (user id and password) system. An example of such log-on screen is shown in FIG. 36.

Furthermore, a "cookie"-based code is used to monitor when users log in and out, and to keep track of how each user uses the system. This will, for example, allow the system to keep attendance at group meetings. If a user has missed a group meeting, the case advisor would then be able to follow up with him or her about the absence.

Referring back to FIG. 59, a firewall 520 is also provided at the server level to protect confidentiality of health plan data. Furthermore, encryption is furnished to ensure that communication between servers 510–516 and PCs 500 is secure.

A network administrator 524, who may be the case administrator or an independent third party, is also attached to the server 508. The network administrator subscribes all users to the system except for clinical or wellness group participants. Physicians or case advisors are responsible for subscribing clinical or wellness members. The network administrator is also in charge of maintaining the system's databases 522.

In the preferred embodiment, the system is constructed using the C++ programming language in conjunction with SQL 6.5, Cold Fusion, commercially available from Alaire Company, Visual Basic, commercially available from Microsoft Corporation), and HTML. Active X and Java components may also be invoked to handle the multimedia functions of the system.

It will be understood that the foregoing is merely illustrative of the principles of the invention, and that various modifications can be made by those skilled in the art without departing from the spirit and scope of the invention as defined by the following claims. For example, the system can be programmed in any number of programming languages besides C++ code to achieve the underlying principles of the present invention. The screens can be reformatted to change their appearance, and many different data sets can be used for various patients with different chronic diseases.

We claim:

1. A method for monitoring compliance with a therapeutic behavior modification program, the method comprising the steps of:

providing a therapeutic behavior modification program having a series of milestones for a patient;

inputting patient data at prescribed times;

correlating the patient's data using a microprocessor with the milestones in the therapeutic behavior modification program to determine whether the patient is complying with the program; and grouping particular data using the microprocessor and linking the data to a remote computer.

2. The method of claim 1 further comprising the step of using the microprocessor to provide graphical screens for encouraging the patient to comply with the therapeutic behavior modification program.

3. A therapeutic behavior modification program, compliance monitoring and feedback system comprising:

means, comprising a relational database and a microprocessor coupled to the database, for developing a therapeutic behavior modification program having a series of milestones for an individual;

means for monitoring the individual's compliance with the program including:
  means for prompting the individual to enter health-related data;
  means for correlating the individual's entered data with the milestones in the behavior modification program and generating compliance data indicative of the individual's progress toward achievement of the program milestones;
means, accessible to the relational database and microprocessor, for motivating the individual to comply with the program comprising an integrated system of graphical system interfaces, the motivating means including:
  means for enabling the individual to review the compliance data;
  means for providing health information to the individual from a remote source;
  an electronic calendar integrated with the behavior modification program for signaling the individual to take action pursuant to the behavior modification program wherein the calendar accesses the relational database and integrates requirements of the program with the individual's daily schedule;
  an electronic journal for enabling the individual to enter personal health-related information;
  an electronic meeting room for linking the individual to a plurality of other individuals having related behavior modification programs for facilitating group peer support sessions for compliance with the program; and
  means for providing motivational media presentations to the individual for encouraging the individual to comply with the program; and
a graphical electronic navigator operable by the individual to control the microprocessor for accessing different parts of the system.

4. The system of claim 3 wherein the means for developing the therapeutic behavior modification program comprises:
  means for inputting preliminary health information relating to the individual;
  means for presenting a plurality of suggested behavior modification programs containing suggested milestones generated as a function of the preliminary health information;
  means for selecting one of the suggested behavior modification programs and altering the milestones to generate the individual's behavior modification program; and
  means for loading the behavior modification program into the relational database.

5. The system of claim 3 further comprising means for providing the motivational media presentations to the individuals in the electronic meeting room as part of the group support sessions, thereby facilitating interactive group discussion about the presentations.

6. The system of claim 3 further comprising means for enabling the individual to select an avatar to represent himself or herself in the electronic meeting room.

7. A method for assisting an individual to comply with a therapeutic behavior modification program, the method comprising the steps of:
  providing the therapeutic behavior modification program having a series of milestones for the individual;
  inputting health data relating to the individual at prescribed times;
  correlating the individual's health data with the milestones in the behavior modification program using a relational database and generating compliance data indicative of whether the individual is complying with the program;
  grouping particular compliance data using a microprocessor and linking the data to a remote computer; and
  motivating the individual to comply with the behavior modification program by:
    providing medical information to the individual relating to the program;
    presenting the individual with the compliance data to allow the individual to personally monitor compliance with the program;
    signaling the individual to take action according to the program through an electronic interface integrated with the individual's daily schedule;
    providing remotely accessible group support sessions and motivational media directed toward encouraging the individual to achieve the program milestones; and
    enabling the individual to retrieve the medical information, compliance data, and scheduling signals, and participate in the group support sessions and view the motivational media through a graphical electronic interface.

8. The method of claim 7 wherein the step of providing remotely accessible group support sessions and motivational media comprises presenting the motivational media during the group support sessions to facilitate interactive group discussion about the presentations.

9. The method of claim 7 further comprising the step of selecting an avatar to represent the individual during the group support sessions.

10. A method for assisting an individual to comply with a computer implemented behavior modification program, the method comprising the steps of:
  providing milestones in the behavior modification program to be achieved by the individual;
  monitoring the individual's compliance with the program by:
    obtaining health-related data of the individual at prescribed times;
    comparing the health-related data with the milestones for generating compliance data indicative of whether the individual is complying with the program, and encouraging the individual to comply with the program if the compliance data indicates lack of compliance; and
  comparing the health-related data against accepted medical protocols and alerting the individual's physician or case advisor when a health-risk is present;
  educating the individual electronically on health topics germane to the individual's condition and behavior modification program; and
  motivating the individual to comply with the behavior modification program by:
    providing group support for the individual by electronically linking the individual to a plurality of other individuals having related behavior modification programs;
    providing a reward to the individual when certain of the milestones are reached;
    presenting the individual with the compliance data for enabling the individual to personally monitor compliance with the program;

enabling the individual to enter comments germaine to the behavior modification program in a computer-implemented journal; and providing motivational multi-media presentations for encouraging the individual to comply with the program.

11. The method of claim 10 wherein the step of obtaining the health-related data comprises the user providing the data through a computer-implemented journal.

12. The method of claim 11 wherein portions of the data in the journal are accessible to a physician.

13. The method of claim 10 wherein the step of obtaining the health-related data comprises a physician obtaining the data from office visits by the individual to the physician.

14. The method of claim 10 wherein the step of educating comprises providing recipes, stress management strategies, and nutritional, dieting, and exercise information to the individual.

15. The method of claim 14 wherein ingredients appearing on the recipes are downloaded automatically to an on-line shopping list.

16. The method of claim 10 wherein the group support is provided by a computer-implemented meeting room wherein the individual and the plurality of other individuals participate in on-line group meetings, the meetings comprising:

a chairperson for monitoring discussions and triggering multimedia presentations; and a means of representing the individual and the plurality of other individuals in the group meetings.

17. The method of claim 16 wherein a computer-implemented schedule book enables the individual to:

view a list of on-line group meetings;

sign-up for a particular group meeting from the list of group meetings; and request automated reminders for reminding the individual of group meetings for which the individual has signed-up.

18. The method of claim 16 wherein the meetings further comprise a means for the individual for contacting the plurality of other individuals via telephone directly from the computer-implemented meeting room.

19. The method of claim 10 wherein the group support is provided by a computer-implemented mentoring area for mentoring and giving support to the individual by other more experienced individuals.

20. The method of claim 19 wherein no more than a predetermined number of the more experienced individuals may be present in the mentoring area at a single time with the individual.

21. The method of claim 10 wherein the group support is provided through electronic mail for facilitating communication with the physician, case advisor, or the plurality of other individuals having related behavior modification programs.

22. The method of claim 10 wherein the group support is provided through an electronic bulletin board wherein the individual posts messages and read messages posted by the other individuals having related behavior modification programs.

23. The method of claim 10 wherein the reward is rewards points for being redeemed for goods, frequent flier miles, or a symbolic reward commending the individual for good work.

24. A therapeutic behavior modification program, compliance monitoring and feedback system comprising:

means, comprising a relational database and a microprocessor coupled to the database, for developing a therapeutic behavior modification program having a series of milestones for an individual;

means for subscribing an individual to the behavior modification program;

means for monitoring the individual's compliance with the program including:

means for obtaining health-related data of the individual at prescribed times for input into a relational database;

means for comparing the health-related data with the milestones in the behavior modification program for generating compliance data indicative of whether the individual is complying with the program, and encouraging the individual to comply with the program if the compliance data indicates lack of compliance; and means for comparing the health-related data against accepted medical protocols and alerting the individual's physician or case advisor when a health-risk is present;

means for educating the individual electronically on health and medical topics germane to the individual's condition and behavior modification program;

means, accessible to the relational database and microprocessor, for motivating the individual to comply with the program including:

means for providing group support for the individual by electronically linking the individual to a plurality of other individuals having related behavior modification programs;

means for providing a reward to the individual when certain of the milestones are reached;

means for presenting the individual with the compliance data for enabling the individual to personally monitor compliance with the program;

means for enabling the individual to enter personal feelings and comments germaine to the behavior modification program into a computer-implemented journal; and means for providing motivational multi-media presentations for encouraging the individual to comply with the program;

means for modifying the program based on the individual's progress; and a graphical user interface for controlling the microprocessor for accessing different parts of the system.

25. The system of claim 24 wherein the means for developing the therapeutic behavior modification program comprises:

means for inputting preliminary health information relating to the individual;

means for presenting a suggested behavior modification program containing suggested milestones generated as a function of the preliminary health information and accepted medical protocols;

means for modifying the suggested behavior modification program to generate the individual's behavior modification program;

means for loading the behavior modification program into the relational database; and means for giving access to the individual to the graphical user interface for controlling the microprocessor for accessing different parts of the system.

26. The system of claim 24 wherein the means for obtaining the health-related data comprises means of prompting the individual to input health-related information into a computer-implemented journal.

27. The system of claim 24 wherein the means of educating comprises means for providing recipes, stress management strategies, and nutritional, dieting, and exercise information to the individual.

28. The system of claim 27 wherein the means for providing recipes includes means for downloading recipe ingredients to a computer-implemented shopping list.

29. The system of claim 24 wherein the means for providing group support comprises means for providing on-line group meetings comprising:

means for electronically viewing a list of group meetings available for participation;

means for electronically registering for a particular group meeting;

means for sending automated reminders for reminding the individual about the particular group meeting for which the individual is registered;

means for providing an electronic meeting room for the group meetings;

means for monitoring discussion during the group meetings; means for triggering multi-media presentations during the group meetings;

means for electronically representing the individual and the plurality of other individuals in the group meetings; and means for contacting the plurality of other individuals via a telephone directly from the computer-implemented meeting room.

30. The system of claim 24 wherein the means for providing group support comprises a means for providing a computer-implemented mentoring area for mentoring and giving support to the individual by other more experienced individuals.

31. The system of claim 24 wherein the means for providing group support comprises electronic mail means for facilitating communication with the plurality of other individuals.

32. The system of claim 24 wherein the means for providing group support comprises electronic bulletin board means for posting messages and reading messages posted by the other individuals having related behavior modification programs.

33. The system of claim 24 further comprising a means for providing security from unauthorized access to the system.

34. The system of claim 24 further comprising a means for health plan payors for monitoring usage of the system.

* * * * *